United States Patent
Donofrio et al.

(10) Patent No.: US 9,192,769 B2
(45) Date of Patent: Nov. 24, 2015

(54) SHUNT-CURRENT REDUCTION TECHNIQUES FOR AN IMPLANTABLE THERAPY SYSTEM

(75) Inventors: William T. Donofrio, Andover, MN (US); John E. Burnes, Coon Rapids, MN (US); Paul G. Krause, Shoreview, MN (US); Gerald P. Arne, Long Lake, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1082 days.

(21) Appl. No.: 12/551,331

(22) Filed: Aug. 31, 2009

(65) Prior Publication Data

US 2010/0114211 A1 May 6, 2010

Related U.S. Application Data

(60) Provisional application No. 61/110,275, filed on Oct. 31, 2008, provisional application No. 61/148,852, filed on Jan. 30, 2009.

(51) Int. Cl.
*A61N 1/08* (2006.01)
*A61N 1/37* (2006.01)
(Continued)

(52) U.S. Cl.
CPC ............... *A61N 1/3718* (2013.01); *A61N 1/08* (2013.01); *A61N 1/36114* (2013.01); *A61N 1/37288* (2013.01); *A61N 2001/086* (2013.01)

(58) Field of Classification Search
CPC ... A61N 1/08; A61N 1/3718; A61N 2001/08; A61N 2001/086
USPC ......................................................... 607/9, 63
See application file for complete search history.

(56) References Cited

U.S. PATENT DOCUMENTS

| 3,421,511 A | 1/1969 | Schwartz et al. |
| 3,522,811 A | 8/1970 | Seymour et al. |
| 3,593,718 A | 7/1971 | Krasner et al. |

(Continued)

FOREIGN PATENT DOCUMENTS

| EP | 0228539 B1 | 11/1990 |
| EP | 0688577 A1 | 12/1995 |

(Continued)

OTHER PUBLICATIONS

International Search Report and Written Opinion from International application No. PCT/US2009/058775, mailed Jan. 27, 2010, 17 pp.

(Continued)

*Primary Examiner* — Tammie K Heller
(74) *Attorney, Agent, or Firm* — Carol F. Barry

(57) ABSTRACT

Techniques for minimizing interference between the first and second medical devices or between the different therapy modules of a common medical device are described herein. In some examples, a medical device may include shunt-current mitigation circuitry and/or at least one clamping structure that helps minimize or even eliminate shunt-current that feeds into a first therapy module of the medical device via one or more electrodes electrically connected to the first therapy module. The shunt-current may be generated by the delivery of electrical stimulation by a second therapy module. The second therapy module may be enclosed in a common housing with the first therapy module or may be separate, e.g., a part of a separate medical device.

41 Claims, 21 Drawing Sheets

(51) Int. Cl.
*A61N 1/36* (2006.01)
*A61N 1/372* (2006.01)

(56) References Cited

U.S. PATENT DOCUMENTS

| | | | |
|---|---|---|---|
| 3,645,267 A | 2/1972 | Hagfors | |
| 3,650,277 A | 3/1972 | Sjostrand et al. | |
| 3,796,221 A | 3/1974 | Hagfors | |
| 3,878,564 A | 4/1975 | Yao et al. | |
| 3,888,260 A | 6/1975 | Fischell | |
| 4,044,774 A | 8/1977 | Corbin et al. | |
| 4,146,029 A | 3/1979 | Ellinwood, Jr. | |
| 4,340,063 A | 7/1982 | Maurer | |
| 4,374,382 A | 2/1983 | Markowitz | |
| 4,428,378 A | 1/1984 | Anderson et al. | |
| 4,458,696 A | 7/1984 | Larimore | |
| 4,485,813 A | 12/1984 | Anderson et al. | |
| 4,535,774 A | 8/1985 | Olson | |
| 4,549,556 A | 10/1985 | Tarjan et al. | |
| 4,686,988 A | 8/1987 | Sholder | |
| 4,694,835 A | 9/1987 | Strand | |
| 4,745,923 A * | 5/1988 | Winstrom | 607/9 |
| 4,750,495 A | 6/1988 | Moore et al. | |
| 4,787,389 A | 11/1988 | Tarjan | |
| 4,827,936 A | 5/1989 | Pless et al. | |
| 4,830,006 A | 5/1989 | Haluska et al. | |
| 4,880,005 A | 11/1989 | Pless et al. | |
| 4,903,701 A | 2/1990 | Moore et al. | |
| 4,998,974 A | 3/1991 | Aker | |
| 5,031,618 A | 7/1991 | Mullett | |
| 5,058,584 A | 10/1991 | Bourgeois | |
| 5,111,816 A | 5/1992 | Pless et al. | |
| 5,117,824 A | 6/1992 | Keimel et al. | |
| 5,135,004 A | 8/1992 | Adams et al. | |
| 5,149,713 A | 9/1992 | Bousquet | |
| 5,199,428 A | 4/1993 | Obel et al. | |
| 5,203,326 A | 4/1993 | Collins | |
| 5,213,098 A | 5/1993 | Bennett et al. | |
| 5,220,917 A | 6/1993 | Cammilli et al. | |
| 5,220,929 A | 6/1993 | Marquit | |
| 5,243,980 A | 9/1993 | Mehra | |
| 5,251,621 A | 10/1993 | Collins | |
| 5,255,691 A | 10/1993 | Otten | |
| 5,261,400 A | 11/1993 | Bardy | |
| 5,292,336 A | 3/1994 | Spence, Jr. et al. | |
| 5,292,338 A | 3/1994 | Bardy | |
| 5,330,505 A | 7/1994 | Cohen | |
| 5,330,507 A | 7/1994 | Schwartz | |
| 5,330,515 A | 7/1994 | Rutecki et al. | |
| 5,331,966 A | 7/1994 | Bennett et al. | |
| 5,334,221 A | 8/1994 | Bardy | |
| 5,342,409 A | 8/1994 | Mullett | |
| 5,345,376 A | 9/1994 | Nourbakhsh | |
| 5,360,441 A | 11/1994 | Otten | |
| 5,464,434 A | 11/1995 | Alt | |
| 5,496,363 A | 3/1996 | Burgio et al. | |
| 5,545,186 A | 8/1996 | Olson et al. | |
| 5,564,434 A | 10/1996 | Halperin et al. | |
| 5,607,418 A | 3/1997 | Arzbaecher | |
| 5,638,832 A | 6/1997 | Singer et al. | |
| 5,651,378 A | 7/1997 | Matheny et al. | |
| 5,690,681 A | 11/1997 | Geddes et al. | |
| 5,700,282 A | 12/1997 | Zabara | |
| 5,702,429 A | 12/1997 | King | |
| 5,755,736 A | 5/1998 | Gillberg et al. | |
| 5,776,170 A | 7/1998 | MacDonald et al. | |
| 5,792,187 A | 8/1998 | Adams | |
| 5,807,234 A | 9/1998 | Bui et al. | |
| 5,817,131 A | 10/1998 | Elsberry et al. | |
| 5,824,021 A | 10/1998 | Rise | |
| 5,859,578 A | 1/1999 | Arnold | |
| 5,913,876 A | 6/1999 | Taylor et al. | |
| 6,006,134 A | 12/1999 | Hill et al. | |
| 6,058,331 A | 5/2000 | King | |
| 6,073,048 A | 6/2000 | Kieval et al. | |
| 6,134,470 A | 10/2000 | Hartlaub | |
| 6,141,586 A | 10/2000 | Mower | |
| 6,178,349 B1 | 1/2001 | Kieval | |
| 6,198,972 B1 | 3/2001 | Hartlaub et al. | |
| 6,272,377 B1 | 8/2001 | Sweeney et al. | |
| 6,308,101 B1 | 10/2001 | Faltys et al. | |
| 6,358,281 B1 | 3/2002 | Berrang et al. | |
| 6,438,420 B1 | 8/2002 | Thompson | |
| 6,473,644 B1 | 10/2002 | Terry, Jr. et al. | |
| 6,587,726 B2 | 7/2003 | Lurie et al. | |
| 6,713,671 B1 | 3/2004 | Wang et al. | |
| 6,788,974 B2 | 9/2004 | Bardy et al. | |
| 6,885,888 B2 | 4/2005 | Rezai | |
| 6,901,292 B2 | 5/2005 | Hrdlicka et al. | |
| 6,944,489 B2 * | 9/2005 | Zeijlemaker et al. | 600/373 |
| 7,010,345 B2 | 3/2006 | Hill et al. | |
| 7,212,864 B2 | 5/2007 | Wahlstrand et al. | |
| 7,218,964 B2 | 5/2007 | Hill et al. | |
| 7,242,982 B2 | 7/2007 | Singhal et al. | |
| 7,305,266 B1 | 12/2007 | Kroll | |
| 7,369,898 B1 | 5/2008 | Kroll et al. | |
| 2001/0001126 A1 | 5/2001 | Cammilli et al. | |
| 2002/0042634 A1 | 4/2002 | Bardy et al. | |
| 2002/0068958 A1 | 6/2002 | Bardy et al. | |
| 2002/0107546 A1 | 8/2002 | Ostroff et al. | |
| 2002/0107553 A1 | 8/2002 | Hill et al. | |
| 2002/0161402 A1 * | 10/2002 | Vogel et al. | 607/1 |
| 2003/0120320 A1 | 6/2003 | Solom | |
| 2005/0017054 A1 | 1/2005 | Iverson et al. | |
| 2005/0267543 A1 | 12/2005 | Heruth et al. | |
| 2005/0288743 A1 | 12/2005 | Ahn et al. | |
| 2006/0217792 A1 | 9/2006 | Hussein et al. | |
| 2007/0055308 A1 | 3/2007 | Haller et al. | |
| 2007/0255332 A1 | 11/2007 | Cabelka et al. | |
| 2008/0015659 A1 | 1/2008 | Zhang et al. | |
| 2009/0281623 A1 | 11/2009 | Kast et al. | |

FOREIGN PATENT DOCUMENTS

| | | |
|---|---|---|
| WO | 02083236 A2 | 10/2002 |
| WO | 03063946 A2 | 8/2003 |
| WO | 2004047295 A1 | 6/2004 |
| WO | 2007/127705 A1 | 11/2007 |
| WO | 2007/149757 A2 | 12/2007 |
| WO | 2008/111986 A1 | 9/2008 |

OTHER PUBLICATIONS

"Common-mode interference" Wikipedia reference retrieved on Aug. 25, 2008, 1 pg.
U.S. Appl. No. 12/609,901, filed Oct. 30, 2009.
U.S. Appl. No. 12/551,409, filed Aug. 31, 2009.
U.S. Appl. No. 12/551,377, filed Aug. 31, 2009.
Bilgutay et al, "Vagal Tuning-A New Concept in the Treatment of Supraventricular Arrhythmias, Angina Pectoris, and Heart Failure," *Journal of Thoracic Cardiovascular Surgery* 56(1): 71-82, Jul. 1968.
Braunwald et al., "Carotid Sinus Nerve Stimulation in the Treatment of Angina Pectoris and Supraventricular Tachycardia," *California Medicine* 112(3): 41-50, Mar. 1970.
Armour, "Instant to Instant Reflex Cardiac Regulation," Cardiology 61: 309-328, 1976.
Schwartz et al., "Effect of dorsal root section on the arrhythmias associated with coronary occlusion," *American Journal of Physiology* 231(3): 923-928, Sep. 1976.
Blair et al., "Responses of Thoracic Spinothalamic Neurons to Intracardiac Injection of Bradykinin in the Monkey," *Circulation Research* 51(1): 83-94, Jul. 1982.
Ammons et al., "Vagal Afferent Inhibition of Spinothalamic Cell Responses to Sympathetic Afferents and Bradykinin in the Monkey," *Circulation Research* 53(5): 603-612, Nov. 1983.
Blair et al., "Responses of Thoracic Spinothalamic and Spinoreticular Cells to Coronary Artery Occlusion," *Journal of Neurophysiology* 51(4): 636-648, Apr. 1984.
Ammons et al., "Effects of intracardiac bradykinin on $T_2$-$T_5$ medial spinothalamic cells," *American Journal of Physiology* 249: R147-R152, 1985.

(56) References Cited

OTHER PUBLICATIONS

Blair et al., "Activation of Feline Spinal Neurones by Potentiated Ventricular Contractions and Other Mechanical Cardiac Stimuli," *Journal of Physiology* 404: 649-667, 1988.
Schwartz et al., "Autonomic Mechanisms and Sudden Death-New Insights From Analysis of Baroreceptor Reflexes in Conscious Dogs With and Without a Myocardial Infarction," *Circulation* 78(4): 969-979, Oct. 1988.
Hobbs et al., "Cardiac and Abdominal Vagal Afferent Inhibition of Primate $T_9$-$S_1$ Spinothalamic Cells," *The American Physiological Society* 257: R889-R895, 1989.
Butler et al., "Cardiac Responses to Electrical Stimulation of Discrete Loci in Canine Atrial and Ventricular Ganglionated Plexi," *The American Physiological Society* 259: H1365-H1373, 1990.
Hull et al., "Heart Rate Variability Before and After Myocardial Infarction in Conscious Dogs at High and Low Risk of Sudden Death," *The American College of Cardiology* 16(4): 978-985, Oct. 1990.
Armour, "Intrinsic Cardiac Neurons," *Journal of Cardiovascular Electrophysiology* 2(4): 331-341, Aug. 1991.
Chandler et al., "Effects of Vagal Afferent Stimulation on Cervical Spinothalamic Tract Neurons in Monkeys," *Pain* 44: 81-87, 1991.
Linderoth et al., "Effects of Sympathectomy on Skin and Muscle Microcirculation During Dorsal Column Stimulation: Animal Studies," *Neurosurgery* 29(6): 874-879, 1991.
Vanoli et al., "Vagal Stimulation and Prevention of Sudden Death in Conscious Dogs With a Healed Myocardial Infarction," *Circulation Research* 68(5): 1471-1481, May 1991.
Cardinal et al., "Distinct Activation Patterns of Idioventricular Rhythms and Sympathetically-Induced Ventricular Tachycardias in Dogs With Atrioventricular Block," *Pace* 15: 1300-1316, Sep. 1992.
Fu et al., "Vagal Afferent Fibers Excite Upper Cervical Neurons and Inhibit Activity of Lumbar Spinal Cord Neurons in the Rat," *Pain* 51: 91-100, 1992.
Hobbs et al., "Evidence That $C_1$ and $C_2$ Propriospinal Neurons Meditate the Inhibitory Effects of Viscerosomatic Spinal Afferent Input on Primate Spinothalamic Tract Neurons," *Journal of Neurophysiology* 67(4): 852-860, Apr. 1992.
Hobbs et al., "Segmental Organization of Visceral and Somatic Input Onto $C_3$-$T_6$ Spinothalamic Tract Cells of the Monkey," *Journal of Neurophysiology* 68(5): 1575-1588, Nov. 1992.
Chandler et al., "A Mechanism of Cardiac Pain Suppression by Spinal Cord Stimulation: Implications for Patients With Angina Pectoris," *European Heart Journal* 14: 96-105, 1993.
Huang et al., "Effects of Transient Coronary Artery Occlusion on Canine Intrinsic Cardiac Neuronal Activity," *Integrative Physiological and Behavioral Science* 28(1): 5-21, Jan.-Mar. 1993.
Adamson et al., "Unexpected Interaction Between β-Adrenergic Blockade and Heart Rate Variability Before and After Myocardial Infarction—A Longitudinal Study in Dogs At High and Low Risk for Sudden Death," *Circulation* 90(2): 976-982, Aug. 1994.
Ardell, "Structure and Function of Mammalian Intrinsic Cardiac Neurons," *Neurocardiology*: 95-114, 1994.
Armour, "Peripheral Autonomic Neuronal Interactions in Cardiac Regulation," *Neurocardiology*: 219-244, 1994.
Foreman, "Spinal Cord Neuronal Regulation of the Cardiovascular System," *Neurocardiology*: 245-276, 1994.
Hull et al., "Exercise Training Confers Anticipatory Protection From Sudden Death During Acute Myocardial Ischemia," *Circulation* 89(2): 548-552, Feb. 1994.
Linderoth et al., "Sympathetic Mediation of Peripheral Vasodilation Induced by Spinal Cord Stimulation: Animal Studies of the Role of Cholinergic and Adrenergic Receptor Subtypes," *Neurosurgery* 35(4): 711-719, Oct. 1994.
Yuan et al., "Gross and Microscopic Anatomy of the Canine Intrinsic Cardiac Nervous System," *The Anatomical Record* 239: 75-87, 1994.
Armour, "Intrinsic Cardiac Neurons Involved in Cardiac Regulation Possess $alpha_1$, $alpha_2$, $beta_1$ and $beta_2$-Adrenoreceptors," *Can. J. Cardiol.* 13(3): 277-284, Mar. 1997.

Cardinal et al., "Reduced Capacity of Cardiac Efferent Sympathetic Neurons to Release Noradrenaline and Modify Cardiac Function in Tachycardia-Induced Canine Heart Failure," *Can. J. Physiol. Pharmacol.* 74: 1070-1078, 1996.
Chandler et al., "Vagal, Sympathetic and Somatic Sensory Inputs to Upper Cervical ($C_1$-$C_3$) Spinothalamic Tract Neurons in Monkeys," *Journal of Neurophysiology* 76(4): 2555-2567, 1996.
Zhang et al., "Thoracic Visceral Inputs Use Upper Cervical Segments to Inhibit Lumbar Spinal Neurons in Rats" *Brain Research* 709: 337-342, 1996.
Armour et al., "Gross and Microscopic Anatomy of the Human Intrinsic Cardiac Nervous System," *The Anatomical Record* 247: 289-298, 1997.
Croom et al., "Cutaneous Vasodilation During Dorsal column Stimulation Is Mediated by Dorsal Roots and CGRP," *Am. J. Physiol.* 272 (*Heart Circ. Physiol.* 41): H950-H957, 1997.
Hautvast et al., "Spinal Cord Stimulation in Chronic Intractable Angina Pectoris: A Randomized, Controlled Efficacy Study," *American Heart Journal*, 136(6): 1114-1120, 1998.
Barron et al., "Spinal Integration of Antidromic Mediated Cutaneous Vasodilation During Dorsal Spinal Cord Stimulation in the Rat," *Neuroscience Letters* 260: 173-176, 1999.
Foreman, "Mechanisms of Cardiac Pain," *Annu. Rev. Physiol.* 61: 143-167, 1999.
Linderoth et al., "Physiology of Spinal Cord Stimulation: Review and Update," *Neuromodulation* 2(3):150-164, 1999.
Qin et al., "Chemical Activation of Cervical Cell Bodies: Effects on Responses to Colorectal Distension in Lumbosacral Spinal Cord of Rats," *J Neurophysiol* 82: 3423-3433, 1999.
Chandler et al., "Intrapericardiac Injections of Algogenic Chemicals Excite Primate $C_1$-$C_2$ Spinothalamic Tract Neurons," *Am J. Physiol. Regulatory Integrative Comp. Physiol.* 279: R560-568, 2000.
Foreman et al., "Modulation of Intrinsic Cardiac Neurons by Spinal Cord Stimulation: Implications for Its Therapeutic Use in Angina Pectoris," *Cardiovascular Research* 47: 367-375, 2000.
Hopkins et al., "Pathology of Intrinsic Cardiac Neurons From Ischemic Human Hearts," *The Anatomical Record* 259: 424-436, 2000.
Kember et al., "Aperiodic Stochastic Resonance in a Hysteretic Population of Cardiac Neurons," *The American Physical Society Physical Review E* 61(2): 1816-1824, Feb. 2000.
Meyerson et al., "Spinal Cord Stimulation," *Bonica's Management of Pain*: 1857-1876, 2001.
Ardell, "Neurohumoral Control of Cardiac Function," *Heart Physiology and Pathophysiology, Fourth Edition*: 45-49, 2001.
Farrell et al., "Angiotensin II Modulates Catecholamine Release Into Interstitial Fluid of Canine Myocardium In Vivo," *Am J. Physiol. Heart Cir. Physiol.* 281: H813-H822, 2001.
Kingma, Jr. et al., "Neuromodulation Therapy Does Not Influence Blood Flow Distribution or Left-Ventricular Dynamics During Acute Myocardial Ischemia," *Autonomic Neuroscience: Basic & Clinical* 91: 47-54, 2001.
Tanaka et al., "Low Intensity Spinal Cord Stimulation May Induce Cutaneous Vasodilation Via CGRP Release," *Brain Research* 896: 183-187, 2001.
Qin et al., "Responses and Afferent Pathways of Superficial and Deeper $C_1$-$C_2$ Spinal Cells to Intrapericardial Algogenic Chemicals in Rats," *J. Neurophysiol* 85:1522-1532, 2001.
Armour et al., "Long-Term Modulation of the Intrinsic Cardiac Nervous System by Spinal Cord Neurons in Normal and Ischaemic Hearts," *Autonomic Neuroscience: Basic & Clinical* 95: 71-79, 2002.
Chandler et al., "Spinal Inhibitory Effects of Cardiopulmonary Afferent Inputs in Monkeys: Neuronal Processing in High Cervical Segments," *J. Neurophysiol* 87: 1290-1302, 2002.
Cardinal et al., "Spinal Cord Activation Differentially Modulates Ischaemic Electrical Responses to Different Stressors in Canine Ventricles," *Autonomic Neuroscience: Basic & Clinical* 111: 37-47, 2004.
Ardell, "Intrathoracic Neuronal Regulation of Cardiac Function," *Basic and Clinical Neurocardiology* 118-152, 2004.
Siddons et al., "Special Considerations: Pacing in Acute Myocardial Infarction," *Cardiac Pacemakers* Chapter 11: 200-217, 1967.

(56) References Cited

OTHER PUBLICATIONS

Bluemel et al., "Parasympathetic Postganglionic Pathways to the Sinoatrial Node," *American Journal of Physiology* 259 (*Heart Circ. Physiol.* 28): H1504-HI510, 1990.

Cooper et al, "Neural Effects on Sinus Rate and Atrioventricular Conduction Produced by Electrical Stimulation from a Transvenous Electrode Catheter in the Canine Right Pulmonary Artery," *Circulation Research* 46(1): 48-57, Jan. 1980.

Randall et al, "Functional Anatomy of the Cardiac Efferent Innervation," *Neurocardiology* Chapter 1: 3-24, 1988.

International Preliminary Report on Patentability from international application No. PCT/US2009/058775, mailed May 12, 2011, 9 pp.

Office Action from U.S. Appl. No. 12/551,409, dated Apr. 23, 2012, 7 pp.

Office Action from U.S. Appl. No. 12/551,377, dated Apr. 23, 2012, 8 pp.

Office Action from U.S. Appl. No. 12/609,901, dated Jul. 13, 2012, 11 pp.

Response to Office Action dated Oct. 2, 2012, from U.S. Appl. No. 12/551,409, and Terminal Disclaimer filed Feb. 1, 2013, 23 pp.

Response to Office Action dated Nov. 7, 2012, from U.S. Appl. No. 12/609,901, filed Jan. 9, 2013, 11 pp.

Response to Office Action dated Oct. 11, 2012, from U.S. Appl. No. 12/551,377, and Terminal Disclaimer filed Jan. 11, 2013, 3 pp.

Office Action from U.S. Appl. No. 12/551,409, dated Oct. 2, 2012, 5 pp.

Response to Office Action dated Jul. 13, 2012, from U.S. Appl. No. 12/609,901, filed Oct. 15, 2012, 13 pp.

Response to Office Action dated Apr. 23, 2012, from U.S. Appl. No. 12/551,377, filed Sep. 21, 2012, 13 pp.

Response to Office Action dated Apr. 23, 2012, from U.S. Appl. No. 12/551,409, filed Sep. 21, 2012, 22 pp.

Office Action from U.S. Appl. No. 12/551,377, dated Oct. 11, 2012, 5 pp.

Final Office Action from U.S. Appl. No. 12/609,901, dated Nov. 7, 2012, 7 pp.

\* cited by examiner

SHUNT-CURRENT REDUCTION TECHNIQUES FOR AN IMPLANTABLE THERAPY SYSTEM

This application claims the benefit of U.S. Provisional Application No. 61/110,275, entitled, "SHUNT-CURRENT REDUCTION TECHNIQUES FOR AN IMPLANTABLE THERAPY SYSTEM," and filed on Oct. 31, 2008, and U.S. Provisional Application No. 61/148,852, entitled, "ISOLATION OF SENSING AND STIMULATION CIRCUITRY," and filed on Jan. 30, 2009, the entire contents of each are incorporated herein by reference.

TECHNICAL FIELD

The disclosure relates to therapy systems, and, more particularly, therapy systems including at least two therapy delivery modules.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry.

For example, implantable cardiac devices, such as cardiac pacemakers, implantable cardioverter defibrillators, or intravenous defibrillators, provide therapeutic stimulation to the heart by delivering electrical therapy signals such as pulses or shocks for pacing, cardioversion or defibrillation pulses via electrodes of one or more implantable leads. In some cases, an implantable cardiac device senses intrinsic depolarizations of the heart and controls the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device delivers pacing, cardioversion or defibrillation signals to the heart of the patient upon detecting ventricular tachycardia, and delivers cardioversion or defibrillation therapy to a patient's heart upon detecting ventricular fibrillation. Some proposed medical device systems include a neurostimulator in addition to the implantable cardiac device.

SUMMARY

In general, the disclosure is directed toward therapy systems that deliver electrical stimulation therapy to a tissue site within a patient and also cardiac rhythm management therapy to a heart of the patient. In some examples, the therapy system includes a first medical device that delivers electrical stimulation to a tissue site within a patient, such as proximate a nonmyocardial tissue site or a nonvascular cardiac tissue site, and a second medical device that delivers cardiac rhythm management therapy, such as at least one of pacing, cardioversion or defibrillation therapy to a heart of the patient. In some examples, the first medical device may be referred to as an implantable neurostimulator (INS) or an electrical stimulator, and the second medical device may be referred to as an implantable cardiac device (ICD), an external cardioverter-defibrillator, or an intravenous defibrillator.

In other examples, the therapy system includes an implantable medical device that includes a first therapy module that delivers stimulation therapy to a tissue site within a patient and a second therapy module that delivers cardiac rhythm management therapy to the heart of the patient, where the first and second therapy modules are disposed in a common housing.

Techniques for minimizing interference between the first and second medical devices or between the different therapy modules of a common medical device are described herein. In some examples, the delivery of electrical stimulation by the second medical device or second therapy module may cause electrical current generated by the electrical stimulation to pass through a conductive pathway including electrodes connected to the first medical device or first therapy module. The current flow through the conductive pathway including the electrodes connected to the first medical device (or first therapy module) may be referred to as "shunt-current." In some examples, the first medical device or the implantable medical device including the first and second therapy modules comprise shunt-current mitigation circuitry that reduces or eliminates the shunt-current. Reducing the shunt-current may help reduce the current density at an interface between the electrodes connected to the first medical device (or first therapy module) and tissue of the patient. In addition, reducing the shunt-current may help limit the passage of currents to therapy components within a housing of the first medical device or the first therapy module.

In another aspect, the disclosure is directed to a system comprising a first therapy module comprising a housing and a signal generator enclosed within the housing, wherein the signal generator generates and delivers electrical stimulation to a first tissue site within a patient via a first electrode electrically connected to the signal generator, a second therapy module that delivers electrical stimulation to a second tissue site within the patient, a second electrode, and a clamping structure that electrically connects the second electrode to the housing of the first therapy module, wherein the clamping structure reduces a shunt-current introduced into the first therapy module via the first electrode, and wherein the shunt-current is generated by the delivery of electrical stimulation by the second therapy module.

In another aspect, the disclosure is directed to a method comprising sensing a voltage gradient via a first electrode coupled to a housing of a first therapy module via a clamping structure, wherein the voltage gradient is generated by delivery of electrical stimulation by a second therapy module, activating the clamping structure when the sensed voltage gradient is greater than a threshold voltage value, and reducing a shunt-current introduced into the first therapy module via a second electrode coupled to a signal generator of the first therapy module, wherein the shunt-current is generated by the delivery of electrical stimulation by the second therapy module.

In another aspect, the disclosure is directed to a system comprising means for sensing a voltage gradient via a first electrode coupled to a housing of a first therapy module via a clamping structure, wherein the voltage gradient is generated by delivery of electrical stimulation by a second therapy module, means for activating the clamping structure when the sensed voltage gradient is greater than a threshold voltage value, and means for reducing a shunt-current introduced into the first therapy module via a second electrode coupled to a signal generator of the first therapy module, wherein the shunt-current is generated by the delivery of electrical stimulation by the second therapy module.

In one aspect, the disclosure is directed to a system comprising a first therapy module that delivers electrical stimulation to a first tissue site within a patient via an electrode, a second therapy module that delivers electrical stimulation to a second tissue site within the patient, a shunt-current mitigation circuitry coupled to the electrode, and a processor. The shunt-current mitigation circuitry reduces a shunt-current that is introduced into the first therapy module via the electrode. The shunt-current mitigation circuitry comprises a monitor electrically coupled to the electrode via a wire, where the monitor monitors an electrical parameter value at the electrode and a switch coupled to the monitor. The processor that opens the switch when the electrical parameter value is greater than or equal to a threshold value.

In another aspect, the disclosure is directed to a method comprising receiving a communication signal from a first therapy module that indicates prospective therapy delivery to a patient by the first therapy module, and, in response to receiving the communication signal, opening a switch located between an electrode and a second therapy module electrically connected to the electrode, where opening the switch limits a shunt-current introduced to the second therapy module via the electrode from the therapy delivery by the first therapy module.

In another aspect, the disclosure is directed to a method comprising monitoring an electrical parameter value at an electrode electrically connected to a therapy module that delivers electrical stimulation therapy to a patient, determining whether the electrical parameter value is greater than or equal to a threshold value, and opening a switch that electrically connects the electrode and the therapy module if the electrical parameter value is greater than or equal to the threshold value.

In another aspect, the disclosure is directed to a system comprising means for delivering electrical stimulation therapy to a first tissue site within the patient, means for receiving a communication signal from a therapy module that indicates prospective therapy delivery to a patient by the therapy module, wherein the therapy module delivers electrical stimulation therapy to a second tissue site within the patient that is different than the first tissue site, and means for opening a switch located between an electrode and the means for delivering electrical stimulation therapy in response to receiving the communication signal. Opening the switch limits a shunt-current introduced to the second therapy module electrically connected to the electrode via the electrode from the delivery of electrical stimulation by the therapy module.

In another aspect, the disclosure is directed to a system comprising means for monitoring an electrical parameter value at an electrode electrically connected to a therapy module that delivers electrical stimulation therapy to a patient, means for determining whether the electrical parameter value is greater than or equal to a threshold value, and means for opening a switch that electrically connects the electrode and the therapy module if the electrical parameter value is greater than or equal to the threshold value.

In another aspect, the disclosure is directed to a computer-readable medium comprising computer-executable instructions. The instructions cause a programmable processor to perform any part of the techniques described herein.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
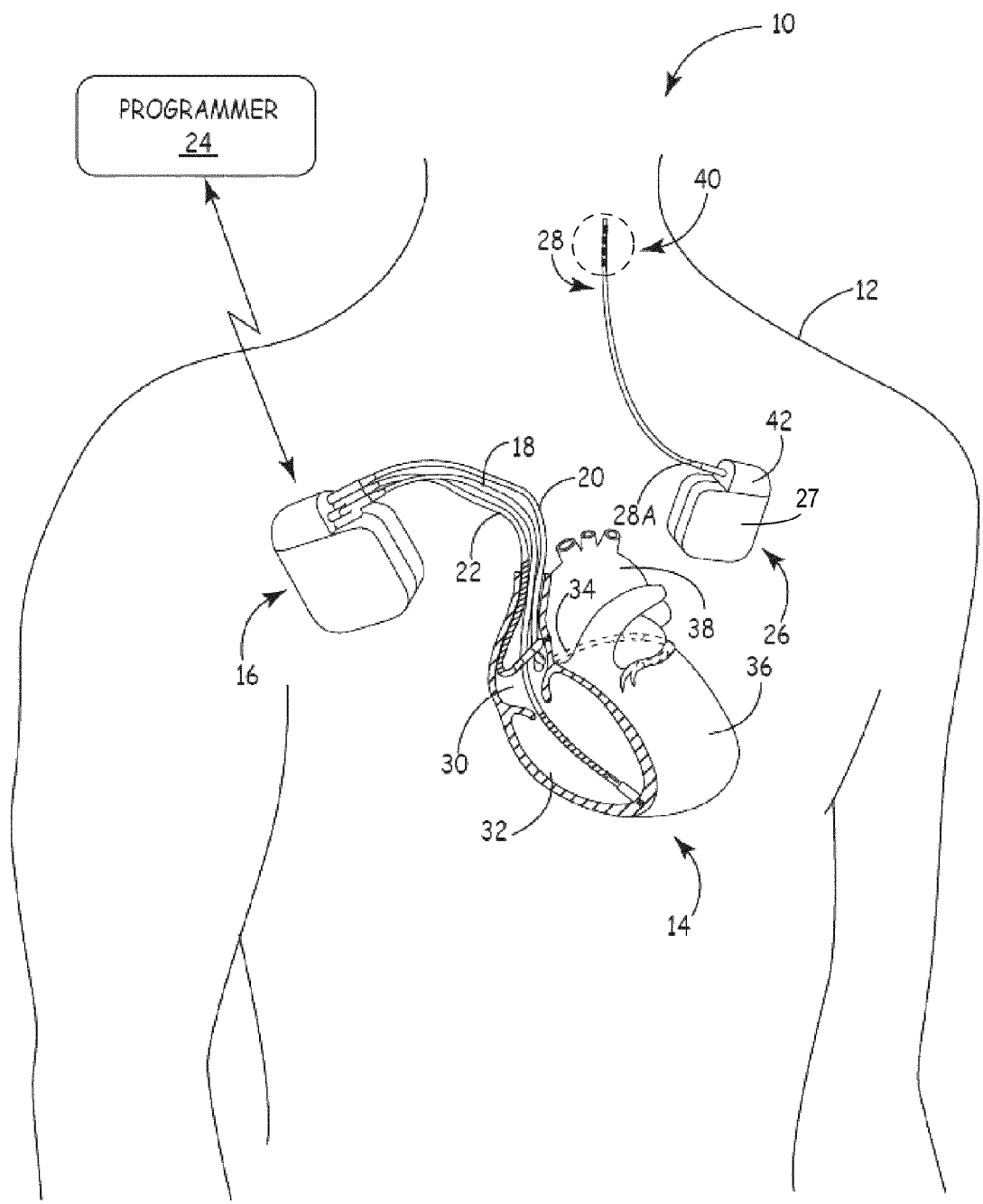
FIG. 1 is a conceptual diagram illustrating an example therapy system including an implantable cardiac device (ICD) and an implantable neurostimulator (INS).

Techniques for minimizing interference between first and second therapy modules are described herein. The first and second therapy modules may be enclosed in physically separate housings (e.g., as part of different medical devices) or in a common medical device housing. As described with respect to FIG. 1, in some examples, the first therapy module may comprise an implantable electrical stimulator that provides electrical stimulation therapy to a tissue site, which may be a nonmyocardial tissue site (e.g., a tissue site proximate a nerve) or a nonvascular cardiac tissue site (e.g., a cardiac fat pad). The second therapy module may comprise a cardiac rhythm therapy module including a stimulation generator that provides at least one of pacing, cardioversion or defibrillation therapy to the heart of the patient. In some examples, the second therapy module may be a part of an implantable device (referred to herein as an implantable cardiac device (ICD)) or an external device that delivers at least one of pacing, cardioversion or defibrillation therapy to the heart of the patient via one or more external electrodes (e.g., electrodes located on the outer surface of the patient's skin). For example, the second therapy module may comprise an automated external defibrillator (AED) or an intravenous defibrillator. In some examples, the second therapy module may also sense electrical cardiac signals of the heart of the patient.

The second therapy module may generate and deliver a stimulation signal to tissue of the patient as part of the pacing, cardioversion or defibrillation therapy. The delivery of the stimulation signal by the second therapy module to tissue may cause an electrical current to flow through implanted electrodes that are electrically connected to the first therapy module. An electrical path including the electrodes may have a relatively lower impedance compared to other electrical paths within the patient's body. The electrical current from the delivery of electrical stimulation by the second therapy module may flow through an electrical path including the electrodes connected to the first therapy module and into the components of the first therapy module. The current that flows into the first therapy module as a result of the delivery of stimulation by the second therapy module, or vice-versa, may be referred to as "shunt-current." Shunt-current may have adverse affects on the components of the current-receiving therapy module. For example, the shunt-current may stress components within the first therapy module housing, such as stimulation generation circuitry or sensing circuitry.

In some examples, the therapy delivery by the second therapy module may be efficacious, despite the flow of shunt-current to the first therapy module. However, reducing the amount of shunt-current at the first therapy module may increase the therapeutic efficacy of therapy delivery by the second therapy module by increasing the intensity of stimulation delivered to patient 12. The intensity of stimulation may be a function of one or more parameters of the electrical stimulation signal, such as the current or voltage amplitude, stimulation signal frequency, and stimulation signal duration.

In addition, the shunt-current may have undesirable physiological effects on tissue of the patient through which the shunt-current flows. For example, the current that flows from the stimulation electrodes connected to the second therapy module and into the first therapy module through tissue of the patient may stress tissue adjacent to the electrodes connected to the first therapy module. In some cases, the flow of the shunt-current through the electrodes connected to the first therapy module may result in a concentration of the current in a relatively small area, which may unintentionally stimulate or stress the tissue adjacent to the electrodes.

Various techniques are described herein to reduce or eliminate a shunt-current that is introduced into a first therapy module, where the shunt-current is at least partially attributable to the delivery of stimulation by a second therapy module that is different than the first therapy module. In accordance with the devices, systems, and techniques described herein, the shunt-current may be minimized without adversely affecting the intensity of stimulation delivered by the second therapy module. Some examples described herein utilize components (e.g., circuit components or nontherapeutic electrodes) to limit the passage of currents through the electrical path including the electrodes connected to the first therapy module.

While techniques for reducing the shunt-current in therapy systems including physically separate medical devices are primarily described herein, the techniques described herein are also applicable to a medical device that comprises separate therapy modules in a common housing, where the therapy modules provide the functions attributed to the separate medical devices here (e.g., the ICD and implantable neurostimulator (INS) described with respect to FIG. 1). In addition, while implanted medical devices are primarily described herein, the systems, devices, and techniques described herein are also applicable to a therapy system comprising at least one external medical device, such as an AED. The AED may be an energy source for an electric field created in the patient. The INS may be located within a portion of the AED electric field, resulting in shunt-current in the INS.

FIG. 1 is a conceptual diagram illustrating an example therapy system 10 that may be used to provide therapy to patient 12. Therapy system 10 includes ICD 16, which is connected to leads 18, 20, and 22, and programmer 24. ICD 16 may be, for example, a device that provides cardiac rhythm management therapy to heart 14, and may include, for example, an implantable pacemaker, cardioverter, and/or defibrillator that provide therapy to heart 14 of patient 12 via electrodes coupled to one or more of leads 18, 20, and 22. In some examples, ICD 16 delivers pacing pulses, but not cardioversion or defibrillation pulses, while in other examples, ICD 16 delivers cardioversion or defibrillation pulses, but not pacing pulses. In addition, in further examples, ICD 16 delivers pacing, cardioversion, and defibrillation pulses, as well as other pulses, to heart 14 of patient 12 to provide therapeutic or stimulative effects.

Therapy system 10 further comprises implantable electrical stimulator 26, which is coupled to lead 28. Electrical stimulator 26 may also be referred to as an implantable neurostimulator (INS) 26. INS 26 may be any suitable implantable medical device (IMD) that includes a signal generator that generates electrical stimulation signals that may be delivered to a tissue site within patient 12, such as a nonmyocardial tissue site (e.g., tissue proximate a nerve) or a nonvascular cardiac tissue site (e.g., a cardiac fat pad). Example tissue sites include, but are not limited to, tissue proximate a vagus nerve, a spinal cord or heart 14 of patient 12. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. The nonmyocardial tissue site may include extravascular tissue sites or intravascular tissue sites.

In some examples, delivery of electrical stimulation to a tissue site proximate a nerve or a nonmyocardial tissue site that may not be proximate a nerve may help modulate an autonomic nervous system of patient 12. In some examples, INS 26 may deliver electrical stimulation therapy to a nerve of patient 12 via a lead implanted within vasculature (e.g., a blood vessel) of patient 12. In some examples, INS 26 may deliver electrical stimulation that is delivered to peripheral nerves that innervate heart 14, or fat pads on heart 14 that may contain nerve bundles. In the example shown in FIG. 1, electrodes of lead 28 are positioned outside the vasculature of patient 12 and positioned to deliver electrical stimulation to target tissue site 40 proximate a vagus nerve (not shown) of patient 12. Stimulation may be delivered to extravascular tissue sites, for example, when lead 28 is not implanted within vasculature, such as within a vein, artery or heart 14. In other examples, stimulation may be delivered to a nonmyocardial tissue site via electrodes of an intravascular lead that is implanted within vasculature.

In the example shown in FIG. 1, the components of ICD 16 and INS 26 are enclosed in separate housings, such that ICD 16 and INS 26 are physically separate devices. For example, as shown in FIG. 1, INS 26 is enclosed within housing 27. Housing 27 may comprise a hermetically-sealed housing that substantially encloses its components. Both ICD 16 and INS 26 may comprise hermetically sealed housings that substantially enclose functional components of the respective device 16, 26, such as sensing circuitry and stimulation circuitry. The components of ICD 16 and INS 26 are described below with reference to FIGS. 6 and 7, respectively.

Leads 18, 20, 22 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. As described in further detail with reference to FIG. 5, in other examples, ICD 16 may deliver stimulation therapy to heart 14 by delivering stimulation to an extravascular tissue site in addition to or instead of delivering stimulation via electrodes of intravascular leads 18, 20, 22.

ICD 16 senses electrical signals attendant to the depolarization and repolarization of heart 14 via electrodes (not shown in FIG. 1) coupled to at least one of the leads 18, 20, 22. In some examples, ICD 16 provides pacing pulses to heart 14 based on the electrical signals sensed within heart 14. These electrical signals sensed within heart 14 may also be referred to as cardiac signals or electrical cardiac signals. The configurations of electrodes used by ICD 16 for sensing and pacing may be unipolar or bipolar. ICD 16 may also provide defibrillation therapy and/or cardioversion therapy via electrodes located on at least one of the leads 18, 20, 22. ICD 16 may detect arrhythmia of heart 14, such as fibrillation of ventricles 28 and 32, and deliver defibrillation therapy to heart 14 in the form of electrical pulses. In some examples, ICD 16 may be programmed to deliver a progression of therapies, e.g., pulses with increasing energy levels, until a fibrillation of heart 14 is stopped. ICD 16 detects fibrillation employing one or more fibrillation detection techniques known in the art.

In the example of FIG. 1, INS 26 is implanted in patient 12 proximate to an extravascular target stimulation site 40, such as a tissue site proximate a vagus nerve. For example, INS 26 may be subcutaneously or submuscularly implanted in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to target stimulation site 40 by implantable medical lead 28, and more particularly, via one or more stimulation electrodes carried by lead 28. Proximal end 28A of lead 28 may be both electrically and mechanically coupled to connector 42 of INS 26 either directly or indirectly (e.g., via a lead extension). In particular, conductors disposed in the lead body may electrically connect stimulation electrodes (and sense electrodes, if present) of lead 28 to INS 26.

INS 26 may also be referred to as a signal generator. In some examples, lead 28 may also carry one or more sense electrodes to permit INS 26 to sense electrical signals from target stimulation site 40. Furthermore, in some examples, INS 26 may be coupled to two or more leads, e.g., for bilateral or multi-lateral stimulation. In examples where lead 28 carries one or more sense electrodes, the sense electrodes may be coupled to a sensing module within INS 26. The sensing module may be configured to withstand approximately 500 volts at its inputs, e.g., inputs that couple to the sense electrodes.

Proximal end 28A of lead 28 may be both electrically and mechanically coupled to connector block 42 of INS 26 either directly or indirectly (e.g., via a lead extension). Conductors disposed in the lead body of lead 28 may electrically connect stimulation electrodes (and sense electrodes, if present) carried by lead 28 to INS 26. As described in more detail below, in addition to conductors, the lead body of lead 28 may comprise a plurality of resistors that electrically couple electrodes of lead 28 to components of INS 26. The resistors may be, for example, positioned between a respective electrode of lead 28 and a sensing module or stimulation generator within INS 26. In some examples, a first side of a resistor may be coupled to at least one of the electrodes of lead 28, and a second side the resistor may be electrically coupled to components within INS 26 via a respective conductor, e.g., a conductive wire.

The size of the resistor may be selected to be low enough to permit INS 26 to efficiently deliver stimulation to patient 12 via lead 28, but high enough to sufficiently limit shunt-current for a given size, location, and configuration of electrodes of lead 28. In some examples, the resistance of the resistor may be selected to be an order of magnitude (e.g., about 10 times) greater than the highest impedance of an electrode electrically connected to lead 28. In addition, the resistance of the resistor may be selected to be substantially equal to or greater than the lowest impedance of an electrode electrically connected to lead 28. In some examples, the resistors of lead 28 may be about ten ohms to about ten kiloohms each. In other examples, the resistors of lead 28 may be about ten kiloohms or greater. However, any suitable resistor value is contemplated by this disclosure.

In some examples, in addition to the plurality of resistors, the lead body of lead 28 comprises a plurality of switches. Each switch of the plurality of switches may be coupled in parallel a respective resistor. A first side of each switch may be coupled to at least one of the electrodes of lead 28 and a second side of each switch may be coupled to INS 26 (e.g., a signal generator or a sensing module of INS 26). INS 26 may close the switch during delivery of a stimulation signal via electrodes of lead 28. In all other instances, the switch may remain open. During delivery of stimulation signal by INS 26, the closed switch may provide a relatively lower impedance path from INS 26 to the at least one electrode of lead 28, as compared to the electrical path through an open switch and/or resistor. In all other instances, the switch may remain open and the resistor may limit the shunt-current into INS 26. In other examples, there is no resistor connected in parallel across each switch. When the switch opens, an open circuit results, and thus there is no shunt-current.

In some examples, instead of or in addition to a plurality of resistors, the lead body comprises resistive wires, instead of or in addition to the conductors of lead 28, whereby the resistive wires electrically couple the electrodes to components (e.g., a stimulation generator or sensing module) within INS 26. In some cases, the resistive wires may electrically couple the second side of each resistor to components within INS 26. The resistive wires may provide approximately 10 ohms to approximately 10 kiloohms of resistance each, approximately 10 ohms to 100 ohms, approximately 3.5 kiloohms to approximately 10 kiloohms. However, any resistive value is contemplated by this disclosure. In other examples, the wire itself may be resistive and/or an integral resistor may be present within the lead.

In some examples, in addition to the resistive wires, the lead body of lead 28 comprises a plurality of switches. Each switch of the plurality of switches may be coupled in parallel with each one of the resistive wires. In such examples, INS 26 may close the plurality of switches during delivery of a stimulation signal. In all other instances, the switches may remain open. During delivery of stimulation signal by INS 26, the closed switches may provide a relatively lower impedance path from INS 26 to the electrodes of lead 28, as compared to the electrical path through an open switch and/or resistor wires. In all other instances, the switches may remain open and the resistive wires may limit the shunt-current into INS 26.

The resistive wires and/or the resistors may help increase the impedance of an electrical path in which shunt-current may travel from ICD 16 to INS 26. Increasing the impedance of the electrical path may help reduce the amount of shunt-current that flows into the stimulation generation circuitry or sensing circuitry within INS 26 via the electrodes coupled to INS 26. The amount of shunt-current that flows into nearby tissue may be reduced because the amount of shunt-current that flows into the stimulation generation circuitry or sensing circuitry within INS 26 is reduced. In this way, reducing the amount of shunt-current that flows through tissue proximate electrodes of lead 28 may help decrease the possibility that tissue near the electrodes may be stressed from the shunt-current flow through the electrodes. Moreover, although the resistors, resistive wires, and/or switches are described as being located within lead 28, in some examples, the resistors, resistive wires, and/or switches may be located within housing 27 of INS 26, connector block 42 of INS 26 or a lead connector (e.g., a lead extension) coupled to INS 26. The resistors, resistive wires, and/or switches coupled to one or more electrodes of lead 28 may be referred to as shunt-current mitigation circuitry that is coupled to the stimulation and/or sensing electrodes of lead 28.

Delivery of electrical stimulation by INS 26 to a nonmyocardial or nonvascular cardiac tissue site (e.g., one or more tissue sites proximate to a nerve, nerve site, cardiac fat pad, or an extravascular target tissue site) that is not proximate a nerve may provide cardioprotective benefits to patient 12. As previously indicated, an extravascular tissue site may be outside of heart 14 and outside of arteries, veins, or other vasculature of patient 12. For example, delivery of neurostimulation by INS 26 may help treat heart failure. In addition, in some examples, delivery of electrical stimulation to the tissue site may help reduce or eliminate cardiovascular conditions such as tachycardia, unhealthy cardiac contractions, ischemia, inefficient heart pumping, inefficient collateral circulation of heart 14 or cardiac muscle trauma. In addition, delivery of electrical stimulation by INS 26 may augment antitachycardia pacing by ICD 16 or provide back-up therapy to ICD 16. For example, if ICD 16 is unavailable to provide therapy to patient 12 (e.g., due to a low power level), INS 26 may deliver therapy to patient 12 to help terminate or prevent a cardiac event (e.g., tachycardia).

In the example shown in FIG. 1, INS 26 provides electrical stimulation therapy of a parasympathetic nerve, such as a vagus nerve, of patient 12. Stimulation of a parasympathetic nerve of patient 12 may help slow intrinsic rhythms of heart 14, which may facilitate antitachyarrhythmia therapy (e.g., antitachycardia pacing, cardioversion or defibrillation) delivered by ICD 16. In this way, neurostimulation by INS 26 may help control a heart rate of patient 12 or otherwise control cardiac function.

In other examples, electrodes of lead 28 may be positioned to deliver electrical stimulation to any other suitable nerve, organ, muscle or muscle group in patient 12, which may be selected based on, for example, a therapy regimen selected for a particular patient. In some examples, INS 26 may deliver electrical stimulation to other parasympathetic nerves, baroreceptors, the carotid sinus or a cardiac branch of the vagal trunk of patient 12 in order to facilitate the delivery of therapy by ICD 16.

Figure 7A:
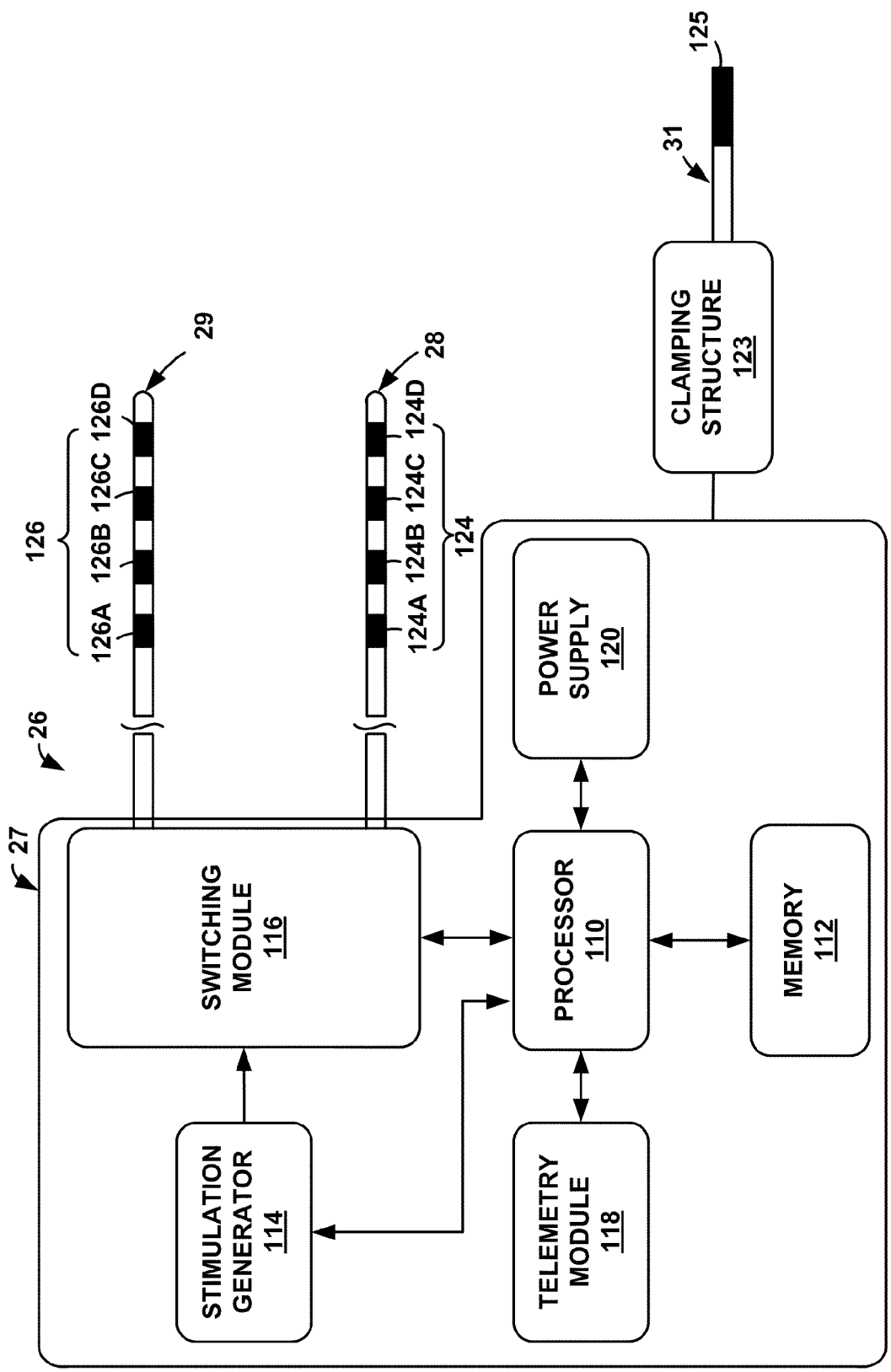
FIG. 7A is a first functional block diagram of an example INS that generates and delivers electrical stimulation signals to a target tissue site other than a heart of a patient.

The electrical stimulation signals generated and delivered by INS 26 may be referred to as neurostimulation signals. However, in some examples, INS 26 may deliver electrical stimulation to a target tissue site 40 that is not proximate to a nerve. For example, in some examples, INS 26 may deliver electrical stimulation to a peripheral nerve field site, whereby the electrodes of lead 28 (e.g., electrodes 124 or electrodes 126, as shown in FIG. 7A) are implanted in a region where patient 12 experiences pain. The pain may be related to stimulation delivered by ICD 16 or a patient condition, such as angina or chronic back pain. As other examples, INS 26 may deliver electrical stimulation to a muscle, muscle group, organ, or other sites that may not be proximate a nerve. Thus, while "neurostimulation" signals are primarily referred to herein, the disclosure is also applicable to examples in which INS 26 delivers electrical stimulation to other sites or than tissue sites proximate a nerve. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve.

Figure 2:
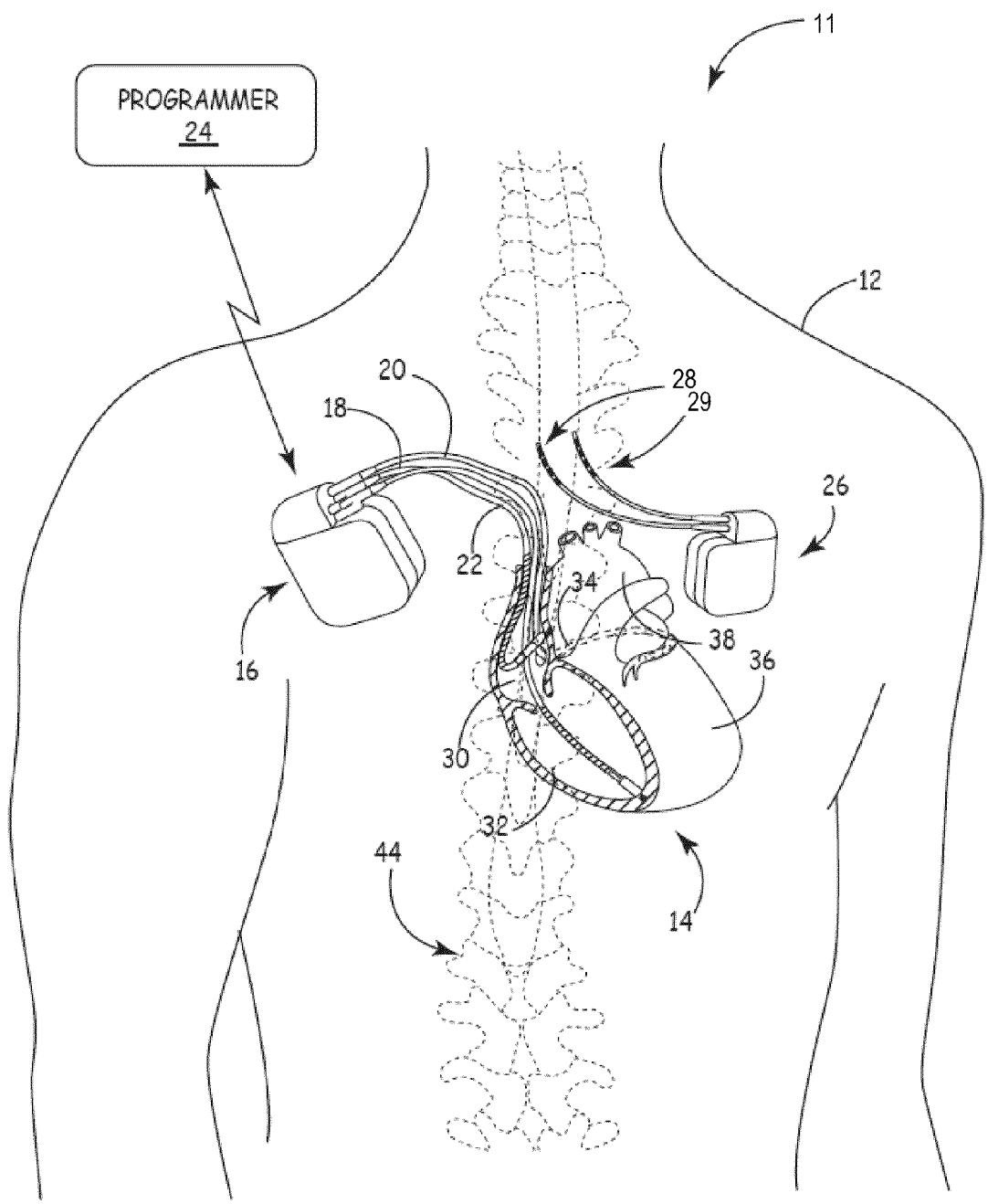
FIG. 2 is a conceptual diagram illustrating another example therapy system that includes the ICD and the INS.

As shown in FIG. 2, in another example, INS 26 may be positioned to deliver electrical stimulation to spinal cord 44 of patient 12. Stimulation of spinal cord 44 or nerves branching therefrom by INS 26 may help prevent or mitigate occurrences of tachyarrhythmias and may facilitate reduction of the level of aggressiveness of the cardiac therapy, such as pacing, cardioversion or defibrillation, delivered by ICD 16. In this way, ICD 16 and INS 26 may operate in conjunction with each other to help prevent arrhythmias of heart 14 of patient 12, as well as to terminate detected arrhythmias.

In some examples, depending upon the neurostimulation target, the delivery of electrical stimulation by INS 26 may also mitigate perceptible discomfort generated from the delivery of pacing pulses or cardioversion/defibrillation shocks by ICD 16. For example, if INS 26 delivers electrical stimulation to spinal cord 44 of patient 12, the neurostimulation may produce paresthesia, which may help reduce the discomfort felt by patient 12 from the delivery of stimulation by ICD 16.

In the example shown in FIG. 2, in therapy system 11, INS 26 is coupled to two leads 28, 29 to provide bilateral stimulation of spinal cord 44. Leads 28, 29 may be introduced into spinal cord 44 in the thoracic region, as shown in FIG. 2. In other examples, leads 28, 29 may be introduced into spinal cord 44 in the cervical or lumbar regions. Electrodes of leads 28, 29 may be positioned within an intrathecal space or epidural space of spinal cord 44, or, in some examples, adjacent nerves that branch off of spinal cord 44. In some examples, leads 28, 29 are implanted within patient 12 and positioned such that electrodes of leads 28, 29 deliver electrical stimulation to locations proximate to the T1 to T6 thoracic vertebrae of the patient's vertebral column. For example, electrodes of at least one of the leads 28, 29 may span the T3 to T6 thoracic vertebrae or deliver electrical stimulation to a tissue site proximate at least one of the T3 to T6 thoracic vertebrae. In other examples, leads 28, 29 may be implanted to deliver electrical stimulation to other regions proximate or within spinal cord 44, such as over or near other vertebrae.

In accordance with this disclosure, in some examples, in therapy system 10 or 11, one or more electrodes of leads 28, 29 may comprise a surface area that is larger than the surface area of the other electrodes of leads 28, 29. In some examples, the electrodes comprising the larger surface area may be electrically connected to housing of INS 26. For example, shunt-current that flows through an electrical path including the one or more electrodes comprising the larger surface area may flow into housing 27 of INS 26. The one or more electrodes that are electrically connected to housing 27 of INS 26 or a heat sink component within INS 26, and which are not used to deliver electrical stimulation therapy to patient 12, may be referred to as a "nontherapeutic electrodes." In some examples, the nontherapeutic electrodes (in addition to or instead of the stimulation or sensing electrodes) may be connected to INS 26 via resistors and/or resistive wires, as described above. In some examples, the nontherapeutic electrodes may be coupled to housing 27 of INS 26 via a diode.

The one or more nontherapeutic electrodes comprising a relatively large surface area compared to the stimulation or sensing electrodes of leads 28, 29 may allow for higher density current to flow through the current path including the nontherapeutic electrode. Increasing the density of current flow through the nontherapeutic electrode may reduce the amount of current that flows through the stimulation and sensing electrodes, which have a smaller surface area than the nontherapeutic electrode. Accordingly, shunt-current that is introduced into the stimulation generation circuitry or sensing circuitry of INS 26 via the electrodes of leads 28, 29 may be reduced because at least some of the shunt-current is diverted to the one or more nontherapeutic electrodes comprising the larger surface area, which are not coupled to the stimulation generation circuitry or sensing circuitry within INS 26. Increasing the shunt-current density that flows through the nontherapeutic electrodes may help reduce the shunt-current density at the therapeutic electrodes. Reducing the shunt-current density at the therapeutic electrodes may reduce the stress resulting from the flow of shunt-current through the tissue adjacent the therapeutic electrodes.

In one example, a stimulating electrode array having more electrodes than needed for stimulation may be used. For example, an 8-electrode array may utilize two electrodes for stimulation of the spine. The remaining six electrodes in the array, which are not used for stimulation, may be any size. The remaining six electrodes may be nontherapeutic electrodes. In one example, the remaining six electrodes in the array may be similar in size to the two stimulating electrodes in the array. As another example, some or all of the remaining six electrodes may be greater in size to the two stimulating electrodes in the array. These remaining six electrodes may be engaged when there is a sufficiently high voltage present between the electrodes, indicative of a need to mitigate shunt current at the stimulating electrode. The six electrodes may be connected via clamping structures to the housing 27, and thus when the clamping structures are activated due to the sufficient high voltage present between the electrodes the six electrodes reduce the amount of shunt-current that flows through the two stimulation electrodes. The six nontherapeutic electrodes provide additional parallel paths for the shunt-current to flow in addition to the electrical paths through the stimulation electrodes. In other words, without the six nontherapeutic electrodes most of the shunt-current may flow through the two stimulation electrodes into the stimulation generator. However, upon activation of the clamping structure, the six nontherapeutic electrodes provide additional electrical paths for the shunt-current to flow. In this manner, at least a portion of the shunt-current does not flow through the stimulation electrodes. Rather, the portion of the shunt-current flows through the six nontherapeutic electrodes into housing 27.

The amount of shunt-current that is diverted from the stimulation electrodes may be a function of the total surface area of the nontherapeutic electrodes, i.e., the total surface area of the six nontherapeutic electrodes. Generally, if the total surface area of the nontherapeutic electrode(s) is greater than the total surface area of the stimulation electrode(s), the nontherapeutic electrode(s) provide a lower impedance electrical path for the shunt-current than the stimulation electrode (s). Accordingly, as described herein, the surface area of the nontherapeutic electrode(s) is described as being large, i.e., greater than the surface area of the stimulation electrodes. However, nontherapeutic electrode(s) having greater surface area than stimulation electrodes is a non-limiting example. In some examples, the total surface area of the nontherapeutic electrode(s) may be less than or equal to the total surface area of the stimulation electrodes. However, even in such examples where the total surface area of the nontherapeutic electrodes is less than or equal to the total surface area of the stimulation electrodes, the nontherapeutic electrodes still provide additional electrical paths to divert at least a portion of the shunt-current away from the stimulation electrodes. Accordingly, nontherapeutic electrodes comprising surface areas less than or equal to the total surface area of the stimulation electrodes may mitigate the shunt-current that flows through the stimulation electrodes.

After the defibrillation is completed, the higher voltage gradient in the vicinity of the electrodes is gone and the clamping structure deactivates and the six electrodes disengage from the stimulating electrodes. The 8-electrode array with two electrodes used for stimulation and six electrodes not used for stimulation is provided for illustration purposes only. The electrode array may comprise more than 8 electrodes. There may be more than or fewer than two electrodes used for stimulation. There may be more than or fewer than six electrodes that are not used for stimulation.

In some examples, the nontherapeutic electrodes are coupled to INS 26 via a clamping structure, as described in more detail with respect to FIG. 7A. Clamping structure may be defined as one or more electrical components that, when activated, provide a lower impedance electrical path to a therapy module, e.g., ICD 16 or INS 26, compared to other electrical paths to the therapy module. As a result, the clamping structure may reduce the shunt-current that may flow through the other electrical paths into circuitry within the therapy module. The clamping structure provides a lower impedance electrical path, compared to the electrical path through the stimulation and sensing electrodes, when the voltage sensed by the nontherapeutic electrodes is greater than a threshold voltage value, e.g., 25 volts (V). When the voltage sensed by the nontherapeutic electrodes is greater than or equal to the threshold voltage value, the clamping structure activates and provides a relatively lower impedance electrical path compared to an electrical path through the stimulation and sensing electrodes of leads 28, 29. Due to the larger surface area of the nontherapeutic electrodes and the lower impedance electrical path, compared to the electrical path through the stimulation and sensing electrode, a substantial portion of the shunt-current may be diverted from the stimulation and sensing electrodes to the nontherapeutic electrodes. In some examples, in addition to or instead of the clamping structure, the nontherapeutic electrodes may be coupled to INS 26 via resistors, diodes, or other components.

It should be noted that in some examples it is not required that the nontherapeutic electrodes have a larger surface area than the therapeutic electrodes, e.g., stimulation or sensing electrodes, but a larger surface area may be helpful in further reducing the shunt-current density. For example, the nontherapeutic electrodes may be of a similar size as the therapeutic electrodes. Though the nontherapeutic electrodes are of a similar size as the therapeutic electrodes, upon activation of the clamping structure, the nontherapeutic electrodes provide electrical paths shunt currents in addition to the electrical paths through the stimulation or sensing electrodes. In this manner, the nontherapeutic electrodes may divert the shunt current away from the stimulation or sensing electrodes even in examples where the nontherapeutic electrodes are of a substantially similar size as the stimulation or sensing electrodes.

In examples in which the nontherapeutic electrode is electrically connected to housing 27 of INS 26, the current that flows through the nontherapeutic electrode is directed to housing 27 of INS 26 or, in some examples, the heat-sink hardware (e.g., conductors) that may be enclosed within housing 27. In addition, the amount of shunt-current that passes through the stimulation and sensing electrodes of leads 28, 29 and into the stimulation generation circuitry or sensing circuitry within INS 26 may be further reduced by other shunt-current mitigation circuitry that is electrically connected to leads 28, 29, such as the mitigation circuitry described with reference to FIG. 1. The shunt-current mitigation circuitry may include, for example, resistors and/or resistive wires that are coupled to at least some of the stimulation and sensing electrodes. The heat sink component described above may also be considered shunt-current mitigation circuitry.

In some examples, instead of or in addition to leads 28, 29 comprising one or more nontherapeutic electrodes with larger surface area than the stimulation or sensing electrodes, the shunt-mitigation circuitry may include a monitor that determines an electrical parameter value at the stimulation or sensing electrodes, e.g., the therapeutic electrodes, of leads 28, 29 and a switch coupled to the monitor. The switch, which opens or closes the electrical path between the one or more electrodes of leads 28, 29 (e.g. the therapeutic electrodes, and the stimulation or sensing circuitry of INS 26), may be opened or closed based on the electrical parameter value. A processor of INS 26 may control the switch based on the electrical parameter value measured by the monitor. In other examples, the monitor controls the switch based on the electrical parameter value measured by the monitor.

The monitor may include, for example, a voltage monitor or a current monitor electrically coupled to one or more of the leads 28, 29. The voltage monitor or current monitor may be coupled to a switch that is coupled to circuitry within INS 26 in series. In other words, the switch is located between the voltage monitor or current monitor and the circuitry within INS 26. At least some of the stimulation and sensing electrodes may be electrically coupled to a first side of a current or voltage monitor. A second side of the current or voltage monitor may be electrically coupled to a first side of a switch, and a second side of the switch may be coupled to circuitry within INS 26, e.g., the stimulation generation circuitry or sensing circuitry within INS 26. In this way, the electrical path between at least some of the electrodes of leads 28, 29 and the stimulation generation circuitry and sensing circuitry within INS 26 may be selectively opened or closed.

In accordance with this disclosure, a voltage monitor coupled to a stimulation or sensing electrode may monitor the voltage at the stimulation or sensing electrode. If the voltage is greater than or equal to a threshold voltage value, the voltage monitor may cause the switch to toggle open, such that limited or no current flows to the circuitry within INS 26. In other examples, a processor within INS 26 causes the switch to toggle open when the voltage at the stimulation or sensing electrode is greater than or equal to a threshold voltage value. In this manner, the shunt-current that feeds into the circuitry within INS 26 is minimized or even eliminated. The threshold voltage may be stored within the voltage monitor or may be stored within INS 26.

In some examples, the threshold voltage value is in a range from about 10 volts to about 1000 volts, such as about 10 volts to about 50 volts, although other threshold voltage values are contemplated. A relatively high threshold voltage value may be useful if INS 26 includes a high voltage blocking circuit that is able to withstand relatively high voltages to which INS 26 may be exposed. However, because there is a possibility that INS 26 may be exposed to higher voltages than the high voltage blocking circuit is designed to withstand, INS 26 may include shunt-current mitigation circuitry, as described herein. Examples of switches that may be coupled to voltage monitors include, but are not limited to, electronic switches, field effect transistor (FET) switches, reed switches, optical isolations, silicon controlled rectifier (SCR), other silicon-based clamping structures, or other electrical components.

If a current monitor is electrically coupled to a stimulation or sensing electrode of leads 28, 29, the current monitor may monitor the current through the respective stimulation or sensing electrode. If the current exceeds a threshold current value, the current monitor may cause the switch to toggle open such that no current can flow to the circuitry within INS 26. Alternatively, a processor within INS 26 may cause the switches to toggle open. Just as with the voltage monitor, toggling the switch to an open position may help limit or even eliminate the amount of shunt-current that feeds into the circuitry within INS 26. The threshold voltage may be stored within the current monitor or may be stored within INS 26.

In some examples, the threshold current value limit is in a range from about 1 milliamps to about 100 amps, such as about 10 milliamps to about 50 milliamps or 1 milliamps to 10 amps, although other threshold current values are contemplated. As one non-limiting example, the total shunt-current that flows through all therapeutic electrodes of leads 28, 29 may range from 10 milliamps to about 100 amps. However, the amount of shunt-current that flows through each electrode may range from 1 milliamp to about 50 milliamps. Examples of switches that may be coupled to the current monitor include, but are not limited to, electronic switches, FET switches, reed switches, optical isolations, SCRs, and the like.

The threshold voltage value for the clamping structure and the voltage monitor and threshold current values may be selected based on a number of factors. For example, the threshold voltage value and/or threshold current value may depend upon how much current or energy the circuitry (e.g., stimulation or sensing circuitry) within INS 26 may tolerate without substantial stress on the circuitry (e.g., stress that may affect operation). In addition, in some cases, the threshold voltage value and/or threshold current value may be selected to minimize stress to the patient's tissue. In these examples, the threshold voltage value and/or threshold current value may depend upon the size of electrodes that are electrically connected to INS 26 and the location of the electrodes because different types of tissue (e.g., subcutaneous tissue, muscle tissue, and the like) may have different current density limitations.

In some examples, INS 26 delivers therapy to patient 12 with a voltage amplitude of about 0.2 volts to about 12 volts, a pulse duration of about 40 microseconds ($\mu$s) to about 600 $\mu$s, such as about 50 $\mu$s to about 500 $\mu$s), and a pulse rate of 1 to 100 Hz (e.g., 10 Hz to 100 Hz). However, other stimulation parameter values for INS 26 are contemplated. INS 26 may deliver electrical stimulation to patient 12 substantially continuously or periodically. In some examples, INS 26 may deliver electrical stimulation to patient 12 based on the timing of electrical stimulation by ICD 16, such as prior to the delivery of electrical stimulation (e.g., antitachycardia pacing or a defibrillation or cardioversion pulse) by ICD 16, during the delivery of electrical stimulation by ICD 16, subsequent to the delivery of electrical stimulation by ICD 16 or any combination of the aforementioned times.

In addition, in some examples, INS 26 delivers electrical stimulation to patient 12 based on a sensed event or, such as atrial or ventricular depolarization, or based on a sensed physiological condition. The event or physiological condition may be sensed by ICD 16, INS 26 or another sensing device. ICD 16 and INS 26 may communicate with each other in order for INS 26 to time the delivery of electrical stimulation based on the delivery of stimulation pulses by ICD 16, where the stimulation pulses may be pacing pulses or cardioversion/defibrillation pulses. ICD 16 and INS 26 may communicate directly or indirectly (e.g., via an intermediate device, such as programmer 24) using any suitable communication technique. Examples communication techniques that may be implemented to facilitate communication between ICD 16 and INS 26 may include, for example, radiofrequency (RF) communication techniques, optical communication techniques, ultrasonic communication techniques, and the like. Communication between ICD 16 and INS 26 may be periodic, e.g., according to a regular schedule, or on an as needed basis, e.g., when INS 26 or ICD 16 delivers electrical stimulation to patient 12.

In other examples, INS 26 delivers electrical stimulation to patient 12 independently of the electrical stimulation delivered by ICD 16. For example, INS 26 may be programmed to deliver electrical stimulation to patient 12 according to a schedule that is determined independently of the actual delivery of stimulation pulses by ICD 16. The schedule may be determined, for example, by a clinician based on a trial stimulation period in which multiple therapy schedules for INS 26 are tested on patient 12. The schedule may dictate when INS 26 actively delivers electrical stimulation to patient 12 and when INS 26 does not actively deliver electrical stimulation to patient 12. For example, the schedule may include a mandatory sleep period for INS 26 during which INS 26 reverts to a relatively low-power sleep mode, during which INS 26 does not deliver therapy to patient 12. The sleep period may be, for example, when patient 12 is sleeping or otherwise has a relatively low activity level. The sleep period may be useful for conserving the power within the power source of INS 26.

In some examples, communication between ICD 16 and INS 26 may also be used to trigger implementation of a shunt-current protection mode of INS 26. Prior to delivery of a stimulation signal by ICD 16, ICD 16 may communicate with INS 26 to indicate the prospective stimulation delivery by ICD 16. For example, ICD 16 may transmit a communication signal to INS 26 that indicates that ICD 16 is intending on delivering a stimulation signal (e.g., a defibrillation shock) to patient 12, e.g., within about five seconds or less. The communication signal may be an electrical signal that does not provide any therapeutic benefits to patient 12 or may be an electrical signal that provides therapeutic benefits to patient, e.g., may be a stimulation signal. Based on the indication that ICD 16 is about to provide a stimulation signal, e.g., a defibrillation shock, INS 26 may change an operating mode to a shunt-current mitigation mode. In some examples, the shunt-current mitigation mode may be implemented by shunt-current mitigation circuitry that includes switches that may help limit the current flow into the stimulation generation circuitry or sensing circuitry within of INS 26.

For example, the sensing and stimulation electrodes electrically connected to one or more therapy modules within housing 27 of INS 26 may be coupled to a first side of a switch, and a second side of the switch may be coupled to the one or more therapy modules. Upon receiving the indication of prospective cardiac rhythm management therapy delivery by ICD 16 to patient 12, INS 26 may toggle the switches open to reduce or even eliminate shunt-current flow through the sensing and stimulation electrodes electrically connected to the sensing or stimulation modules of INS 26. In some examples, a monitor (e.g., current and/or voltage monitor), as described above, may be coupled to the switches. In such examples, the switches may toggle open whenever the voltage or current monitor senses a voltage or current, respectively, that is greater than a threshold value, or the switches may toggle open in response to a signal indicative of the prospective cardiac rhythm management therapy delivery by ICD 16.

The values for the therapy parameters that define the electrical stimulation delivered by INS 26 may be organized into a group of parameter values referred to as a "therapy program" or "therapy parameter set." "Therapy program" and "therapy parameter set" are used interchangeably herein. In the case of electrical stimulation, the therapy parameters may include an electrode combination, and an amplitude, which may be a current or voltage amplitude, and, if INS 26 delivers electrical pulses, a pulse width, and a pulse rate for stimulation signals to be delivered to the patient. An electrode combination may include a selected subset of one or more electrodes of lead 28, as well as lead 29 in the case of therapy system 11 of FIG. 2. The electrode combination may also refer to the polarities of the electrodes in the selected subset. By selecting particular electrode combinations, a clinician may target particular anatomic structures within patient 12. In some cases, INS 26 may deliver stimulation to patient 12 according to a program group that includes more than one therapy program. The stimulation signals according to the different therapy programs in a therapy group may be delivered on a time-interleaved basis or substantially simultaneously.

If INS 26 delivers therapy to patient 12 according to two or more electrode combinations, e.g., according to a therapy program group including two or more therapy programs defining at least two different electrode combinations, timeinterleaving the stimulation signals defined each of the therapy programs may result in stimulation that is sequentially applied to different electrodes.

Programmer 24 may include a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with ICD 16 and/or INS 26. For example, the user may interact with programmer 24 to retrieve physiological or diagnostic information from ICD 16 and/or INS 26. A user may also interact with programmer 24 to program ICD 16 and INS 26, e.g., select values for operational parameters of ICD 16 and INS 26, respectively.

For example, the user may use programmer 24 to retrieve information from ICD 16 regarding the rhythm of heart 14, trends therein over time, or tachyarrhythmia episodes. As another example, the user may use programmer 24 to retrieve information from ICD 16 regarding other sensed physiological parameters of patient 12, such as electrical depolarization/repolarization signals from the heart (referred to as "electrogram" or EGM), intracardiac or intravascular pressure, activity, posture, respiration, or thoracic impedance. As another example, the user may use programmer 24 to retrieve information from ICD 16 regarding the performance or integrity of ICD 16 or other components of system 10, such as leads 18, 20, and 22, or a power source of ICD 16.

The user may use programmer 24 to program a therapy progression, select electrodes used to deliver defibrillation pulses, select waveforms for the defibrillation pulse, or select or configure a fibrillation detection algorithm for ICD 16. The user may also use programmer 24 to program aspects of other therapies provided by INS 26, such as cardioversion or pacing therapies. In some examples, the user may activate certain features of ICD 16 by entering a single command via programmer 24, such as depression of a single key or combination of keys of a keypad or a single point-and-select action with a pointing device.

As another example, the user may use programmer 24 to retrieve information from INS 26 regarding the performance or integrity of INS 26 or lead 28 (and lead 29 if the therapy system includes lead 29), or a power source of INS 26. With the aid of programmer 24 or another computing device, a user may select values for therapy parameters for controlling therapy delivery by INS 26. By selecting values for amplitude, pulse width, and pulse rate, the physician can attempt to generate an efficacious therapy for patient 12 that is delivered via the selected electrode subset.

Programmer 24 may communicate with ICD 16 and INS 26 via wireless communication using any techniques known in the art. Examples of communication techniques may include, for example, low frequency or RF telemetry, but other techniques are also contemplated. In some examples, programmer 24 may include a programming head that may be placed proximate to the patient's body near the ICD 16 and INS 26 implant sites in order to improve the quality or security of communication between ICD 16 or INS 26, respectively, and programmer 24.

Figure 3:
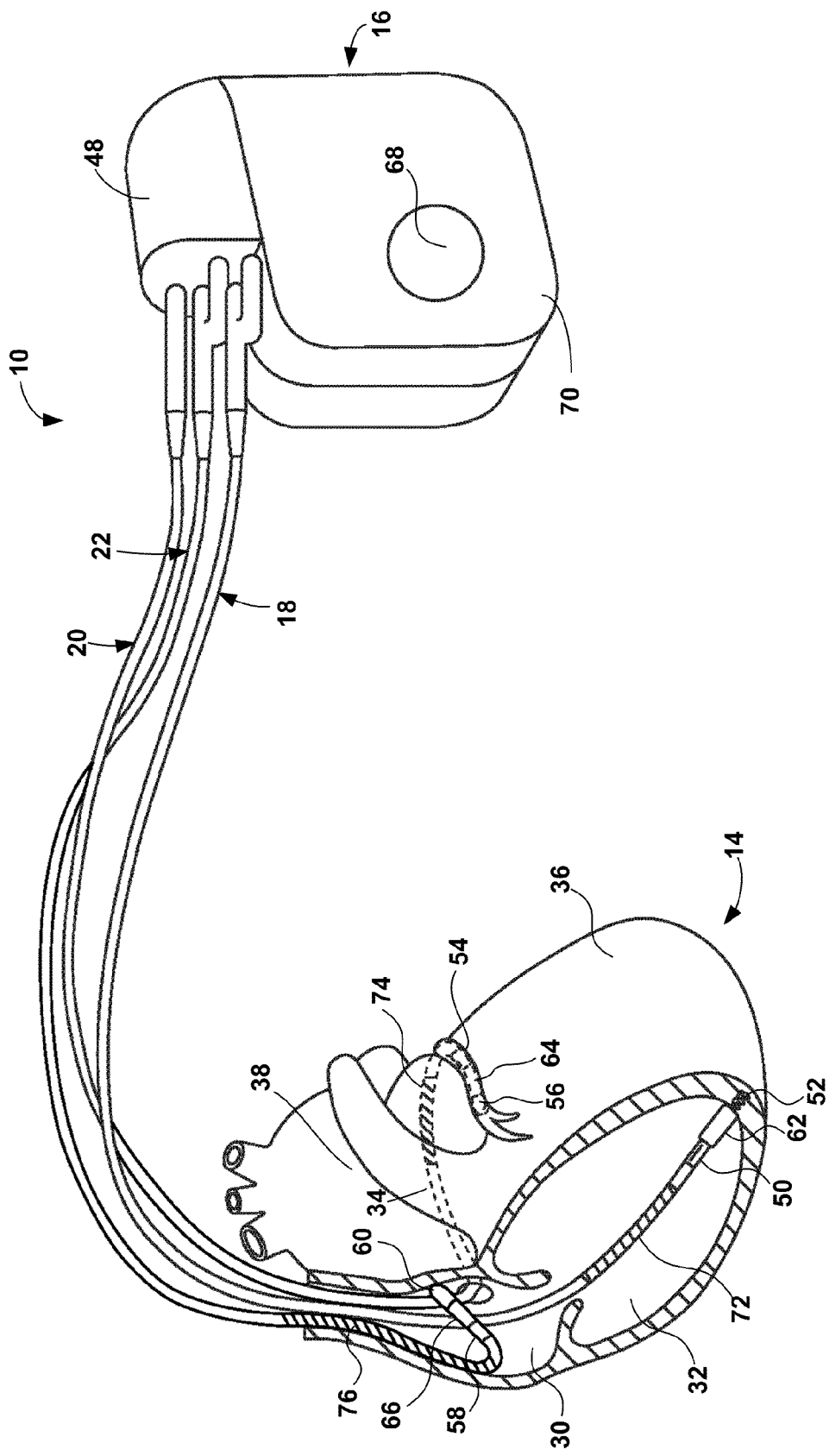
FIG. 3 is a conceptual diagram illustrating the ICD of FIGS. 1 and 2 and the respective leads in greater detail.

FIG. 3 is a conceptual diagram illustrating ICD 16 and leads 18, 20, and 22 of therapy system 10 in greater detail. Leads 18, 20, 22 may be electrically coupled to a stimulation generator, a sensing module, or other modules ICD 16 via connector block 48. In some examples, proximal ends of leads 18, 20, 22 may include electrical contacts that electrically couple to respective electrical contacts within connector block 48. In addition, in some examples, leads 18, 20, 22 may be mechanically coupled to connector block 48 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. Other lead configurations are also contemplated, such as configurations that do not include coiled conductors. In the illustrated example, bipolar electrodes 40 and 42 are located proximate to a distal end of lead 18. In addition, bipolar electrodes 54 and 56 are located proximate to a distal end of lead 20 and bipolar electrodes 58 and 60 are located proximate to a distal end of lead 22.

Electrodes 50, 54, and 58 may take the form of ring electrodes, and electrodes 52, 56, and 60 may take the form of extendable helix tip electrodes mounted retractably within insulative electrode heads 62, 64, and 66, respectively. Each of the electrodes 50, 52, 54, 56, 58, and 60 may be electrically coupled to a respective one of the coiled conductors within the lead body of its associated lead 18, 20, 22, and thereby coupled to respective ones of the electrical contacts on the proximal end of leads 18, 20 and 22.

Electrodes 50, 52, 54, 56, 58, and 60 may sense electrical signals attendant to the depolarization and repolarization of heart 14. The electrical signals are conducted to ICD 16 via the respective leads 18, 20, 22. In some examples, ICD 16 also delivers pacing pulses via electrodes 50, 52, 54, 56, 58, and 60 to cause depolarization of cardiac tissue of heart 14. In some examples, as illustrated in FIG. 2, ICD 16 includes one or more housing electrodes, such as housing electrode 68, which may be formed integrally with an outer surface of hermetically-sealed housing 70 of ICD 16 or otherwise coupled to housing 70. In some examples, housing electrode 68 is defined by an uninsulated portion of an outward facing portion of housing 70 of ICD 16. Other division between insulated and uninsulated portions of housing 70 may be employed to define two or more housing electrodes. In some examples, housing electrode 68 comprises substantially all of housing 70. Any of the electrodes 50, 52, 54, 56, 58, and 60 may be used for unipolar sensing or pacing in combination with housing electrode 68. As described in further detail with reference to FIG. 4, housing 70 may enclose a stimulation generator that generates cardiac pacing pulses and defibrillation or cardioversion shocks, as well as a sensing module for monitoring the patient's heart rhythm.

Leads 18, 20, 22 also include elongated electrodes 72, 74, 76, respectively, which may take the form of a coil. ICD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, such as, but not limited to, platinum, platinum alloy or other materials known to be usable in implantable defibrillation electrodes.

The configurations of therapy system 10 illustrated in FIGS. 1-3 are merely examples. In other examples, a therapy system may include epicardial leads and/or patch electrodes instead of or in addition to the transvenous leads 18, 20, 22 illustrated in FIG. 1. Further, ICD 16 and INS 26 need not be implanted within patient 12. In examples in which ICD 16 is not implanted in patient 12, ICD 16 may deliver defibrillation pulses and other therapies to heart 14 via percutaneous leads that extend through the skin of patient 12 to a variety of positions within or outside of heart 14 or via external patch electrodes. In examples in which INS 26 is not implanted in patient 12, INS 26 may deliver electrical stimulation to target tissue sites within patient 12 via external electrodes or via percutaneous leads that extend through the skin of patient 12.

In other examples of therapy systems that provide electrical stimulation therapy to heart 14, a therapy system may include any suitable number of leads coupled to ICD 16, and each of the leads may extend to any location within or proximate to heart 14. Other examples of therapy systems may include three transvenous leads located as illustrated in FIGS. 1 and 3, and an additional lead located within or proximate to left atrium 38. Alternatively, other examples of therapy systems may include a single lead that extends from ICD 16 into right atrium 30 or right ventricle 32, or two leads that extend into a respective one of the right ventricle 32 and right atrium 30. An example of this type of therapy system is shown in FIG. 4.

Figure 4:
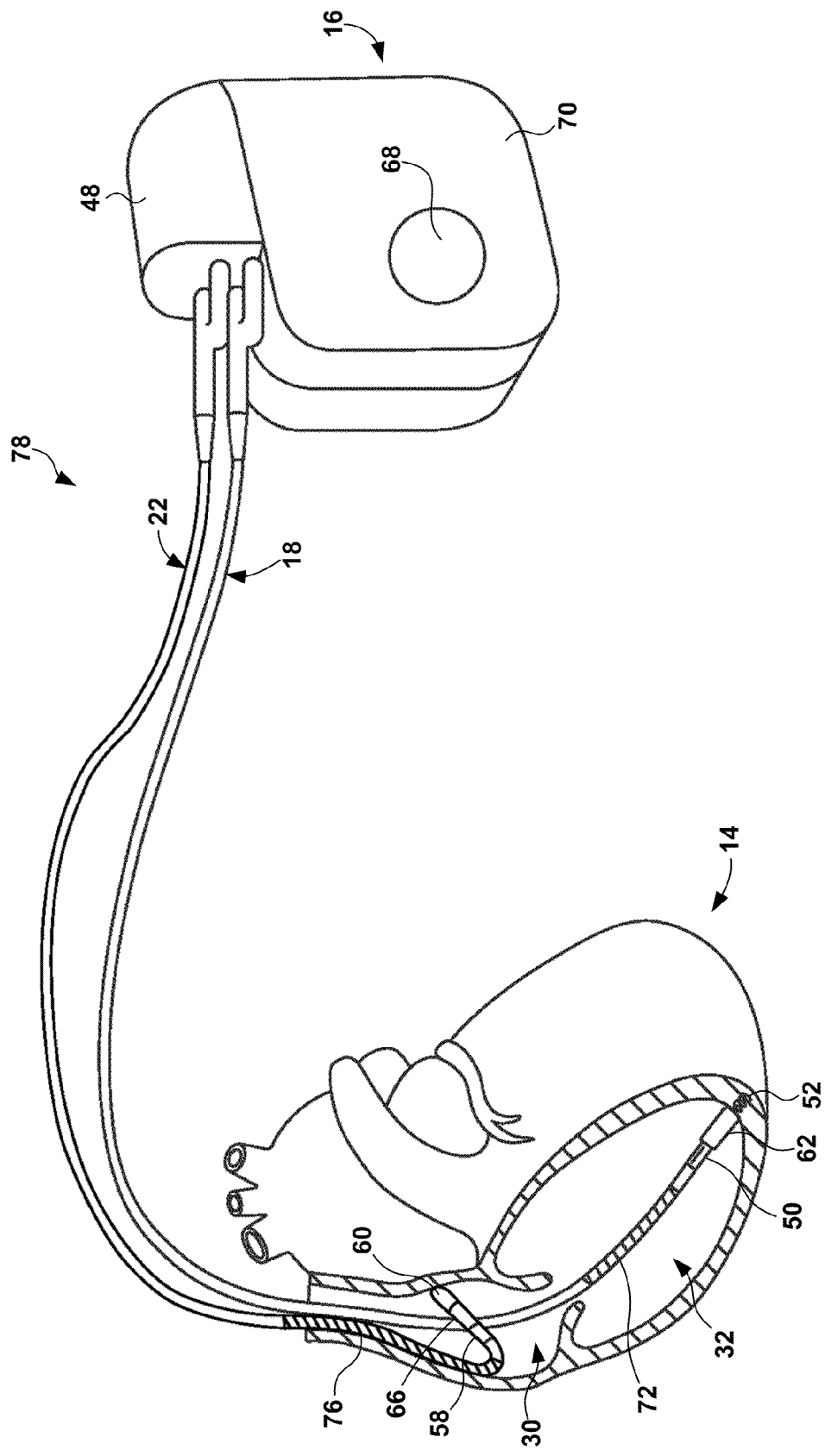
FIG. 4 is a conceptual diagram illustrating another example of the ICD of FIGS. 1 and 2 and the respective leads in greater detail.

FIG. 4 is a conceptual diagram illustrating another example of therapy system 78, which is similar to therapy system 10 of FIGS. 1 and 2, but includes two leads 18, 22, rather than three leads. Leads 18, 22 are implanted within right ventricle 32 and right atrium 30, respectively. Therapy system 78 shown in FIG. 4 may be useful for providing defibrillation and pacing pulses to heart 14. Therapy system 78 may further include INS 26 (not shown in FIG. 4), which is configured to deliver electrical stimulation therapy in order to help prevent or mitigate an arrhythmia of patient 12. As previously indicated, INS 26 may deliver stimulation therapy to modulate an autonomic nervous system of patient 12.

Figure 5:
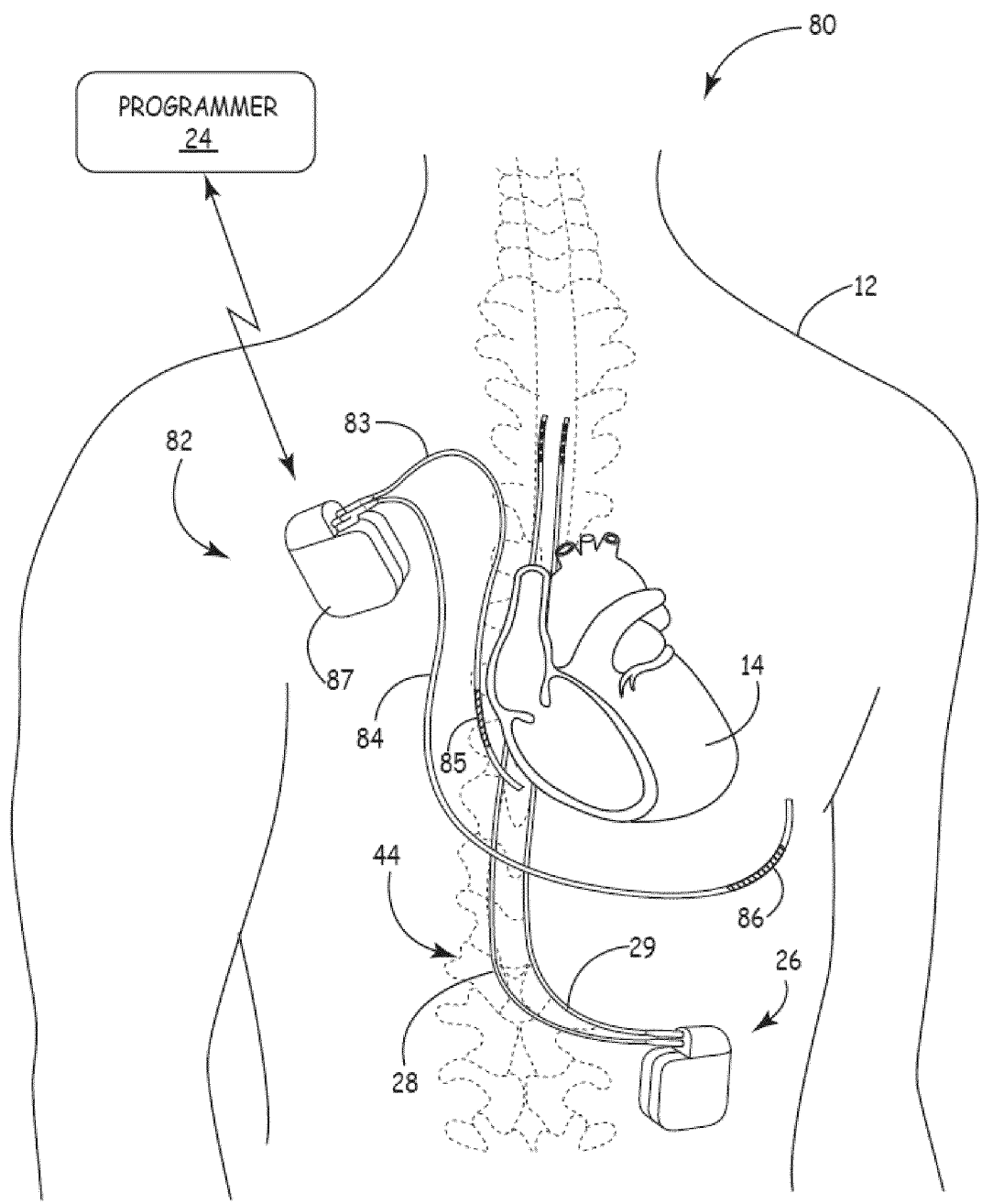
FIG. 5 is a conceptual diagram illustrating another example therapy system that includes an ICD and an INS.

FIG. 5 is a conceptual diagram of another example therapy system 80 that includes two medical devices that provide therapy to patient 12, e.g., to manage a cardiac condition such as heart failure. In addition to INS 26, therapy system 80 includes ICD 82, which delivers electrical stimulation to heart 14 without intravascular leads. ICD 82 is coupled to extravascular leads 83, 84, that each include at least one electrode 85, 86. Electrodes 85, 86 may be subcutaneous coil electrodes, which may be positioned within a subcutaneous tissue layer of patient 12. In other examples, electrodes 85, 86 may comprise any other suitable type of extravascular electrode. For example, electrodes 85, 86 may include any other type of subcutaneous electrode, such as subcutaneous ring electrodes, subcutaneous plate electrodes, subcutaneous patch or pad electrodes, a submuscular electrode, an epicardial electrode or an intramural electrode.

Electrodes 85 may be located within the thoracic cavity of patient 12 proximate to right ventricle 32 (FIG. 1), on the patient's side or back, or any other portion of the body appropriate for providing electrical stimulation to heart 14. Electrode 86 may be located within the thoracic cavity of patient 12 proximate left ventricle 36 (FIG. 1), on the patient's side or back, or any other portion of the body appropriate for providing electrical stimulation to the heart. Similar extravascular electrodes are disclosed in commonly-assigned U.S. Pat. No. 5,261,400 to Bardy, which is entitled "DEFIBRILLATOR EMPLOYING TRANSVENOUS AND SUBCUTANEOUS ELECTRODES AND METHOD OF USE" and issued Nov. 16, 1993, and U.S. Pat. No. 5,292,338 to Bardy, which is entitled "ATRIAL DEFIBRILLATOR EMPLOYING TRANSVENOUS AND SUBCUTANEOUS ELECTRODES AND METHOD OF USE" and issued Mar. 8, 1994. U.S. Pat. Nos. 5,261,400 and 5,292,338 are incorporated herein by reference in their entireties.

Leads 83, 84 may be electrically coupled to stimulation modules, and, in some cases, sensing modules, that are enclosed within housing 87 of ICD 82. As with housing 70 of ICD 16 (FIG. 3), housing 87 may comprise a hermetic housing that substantially encloses the components of ICD 16, such as a sensing module, stimulation generator, processor and the like. Components of an example ICD 16 or ICD 82 are described with respect to FIG. 6. ICD 82 may deliver electrical stimulation (e.g., pacing, cardioversion or defibrillation pulses) to heart 14 between electrodes 85, 86 e.g., in a bipolar configuration. In other examples, ICD 82 may deliver electrical stimulation to heart 14 between electrodes 85 and housing 87, or between electrode 86 and housing 87, e.g., in a unipolar configuration.

Just as with ICD 16 (FIG. 1) that delivers cardiac rhythm management therapy to heart 14 via intravascular electrodes, the delivery of electrical stimulation by ICD 82 may cause a shunt-current to flow through the electrodes electrically connected to INS 26. Thus, in therapy system 80, INS 26 may include shunt-current mitigation circuitry, e.g., as described above with respect to FIG. 1.

In addition, the delivery of electrical stimulation by INS 26 may cause a shunt-current to flow through the electrodes of leads 18, 20, and 22 electrically connected to ICD 16 (FIG. 1) or leads 83, 84 electrically connected to ICD 82 (FIG. 5). In accordance with this disclosure, the various shunt-current mitigation techniques (e.g., shunt-current mitigation circuitry) described herein may be used to mitigation the shunt-current that may flow through electrodes connected to ICD 16. For purposes of clarity and illustration, the shunt-current mitigation circuitry is described with respect to INS 26. However, the various shunt-current mitigation circuitries described herein may be coupled to the electrodes of leads that couple to ICD 16 or ICD 82. While the disclosure primarily refers to therapy system 10 including ICD 16 (FIG. 1) and INS 26, the description of the techniques, systems, and devices herein are also applicable to therapy system 80 including ICD 82 and INS 26.

In some examples, stimulation signals delivered by an AED may cause shunt-current to flow into INS 26 or ICD 16. The shunt-mitigation circuitry described herein may also be used to limit that amount of shunt-current generated by a stimulation from an AED that feeds into INS 26 or ICD 16. In examples in which an AED generates a shunt-current, only one of the implantable medical devices, e.g. either INS 26 or ICD 16, may be implanted within patient 12.

Figure 6:
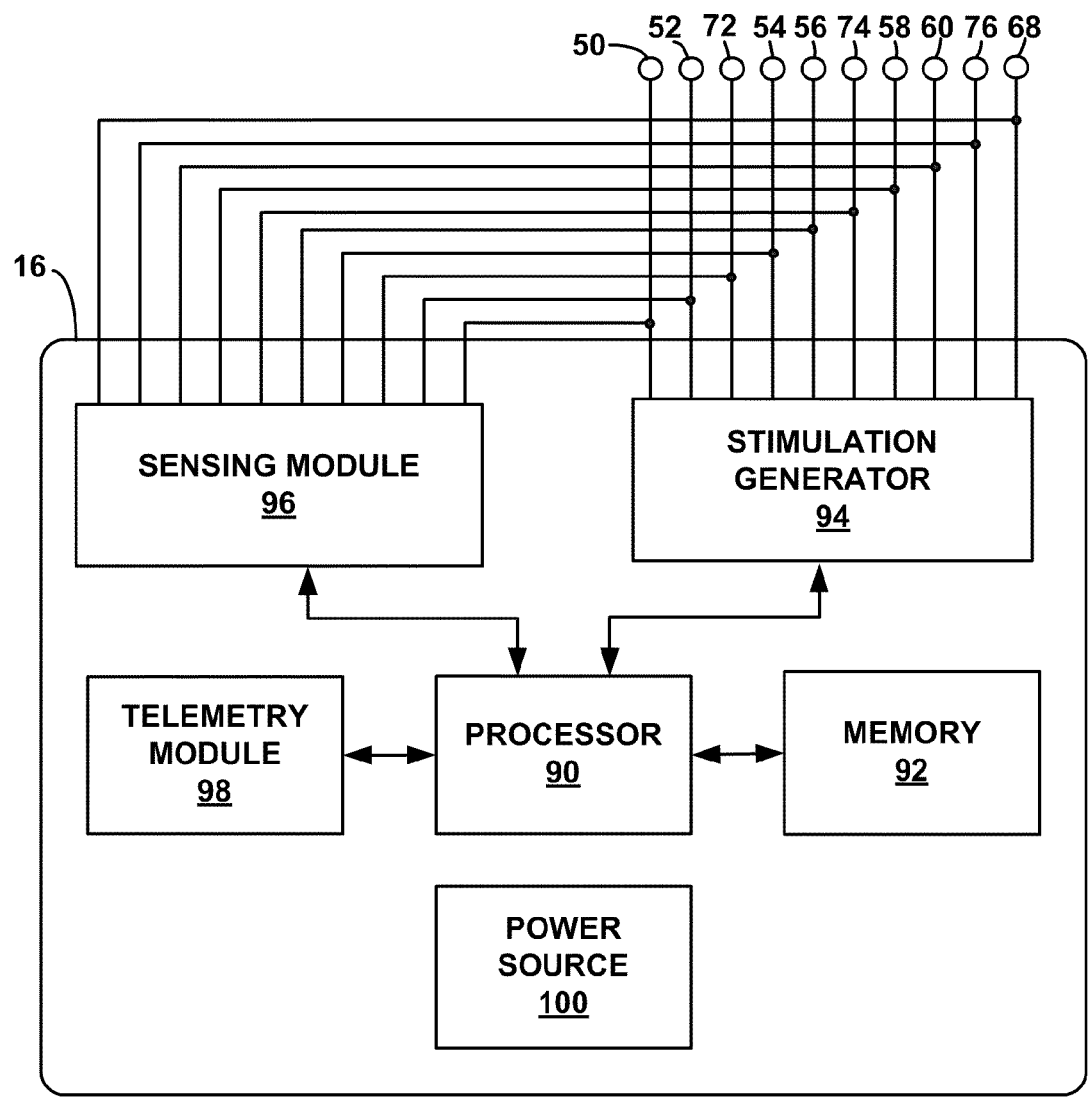
FIG. 6 is a functional block diagram of an example ICD that generates and delivers electrical stimulation to a heart of a patient.

FIG. 6 is a functional block diagram of an example configuration of ICD 16 (FIG. 1), which includes processor 90, memory 92, stimulation generator 94, sensing module 96, telemetry module 98, and power source 100. The block diagram shown in FIG. 6 may also illustrate an example configuration of ICD 82 (FIG. 5). Memory 92 includes computer-readable instructions that, when executed by processor 90, cause ICD 16 and processor 90 to perform various functions attributed to ICD 16 and processor 90 herein. Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof. Processor 90 controls stimulation generator 94 to deliver stimulation therapy to heart 14 according to a selected one or more of therapy programs, which may be stored in memory 92. Specifically, processor 90 may control stimulation generator 94 to deliver electrical pulses with the amplitudes, pulse widths, frequency, or electrode polarities specified by the selected one or more therapy programs.

Stimulation generator 94 is electrically coupled to electrodes 50, 52, 54, 56, 58, 60, 68, 72, 74, and 76, e.g., via conductors of the respective lead 18, 20, 22, or, in the case of housing electrode 68, via an electrical conductor disposed within housing 70 of ICD 16. Stimulation generator 94 is configured to generate and deliver cardiac rhythm management therapy to heart 14. For example, stimulation generator 94 may deliver defibrillation shocks to heart 14 via at least two electrodes 68, 72, 74, 76. Stimulation generator 94 may deliver pacing pulses via ring electrodes 50, 54, 58 coupled to leads 18, 20, and 22, respectively, and/or helical electrodes 52, 56, and 60 of leads 18, 20, and 22, respectively. In some examples, stimulation generator 94 delivers pacing, cardioversion, or defibrillation stimulation in the form of electrical pulses. In other examples, stimulation generator 94 may deliver one or more of these types of stimulation in the form of other signals, such as sine waves, square waves, or other substantially continuous time signals.

In some examples, stimulation generator 94 may include a switch module (not shown in FIG. 6) and processor 90 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes. In other examples, however, stimulation generator 94 may independently deliver stimulation to electrodes 50, 52, 54, 56, 58, 60, 68, 72, 74, and 76 or selectively sense via one or more of electrodes 50, 52, 54, 56, 58, 60, 68, 72, 74, and 76 without a switch matrix.

Sensing module 96 monitors signals from at least one of electrodes 50, 52, 54, 56, 58, 60, 68, 72, 74, and 76 in order to monitor electrical activity of heart 14, e.g., via an EGM signal. Sensing module 96 may also include a switch module (not shown in FIG. 6) to select a particular subset of available electrodes to sense the heart activity. In some examples, processor 90 may select the electrodes that function as sense electrodes via the switch module within sensing module 96, e.g., by providing signals via a data/address bus. In some examples, sensing module 96 includes one or more sensing channels, each of which may comprise an amplifier. In response to the signals from processor 90, the switch module of within sensing module 96 may couple the outputs from the selected electrodes to one of the sensing channels.

In some examples, shunt-current mitigation circuitry described herein with respect to INS 26 may also be used to electrically connect electrodes 50, 52, 54, 56, 58, 60, 68, 72, 74, and 76 to stimulation generator 94 and sensing module 96. The shunt-current mitigation circuitry may be located between ICD 16 and the electrodes. In some examples, in addition to or instead of the shunt-current mitigation circuitry, nontherapeutic electrodes may be electrically coupled to the housing of ICD 16, e.g., housing 70 (shown in FIGS. 3 and 4). The nontherapeutic electrodes may be coupled to housing 70 via clamping structures, resistors, diodes, and the like. However, in examples where nontherapeutic electrodes are coupled to housing 70, electrode 68 (FIGS. 3 and 4) may not be coupled to housing 70.

One channel of sensing module 96 may include an R-wave amplifier that receives signals from electrodes 50 and 52, which are used for pacing and sensing in right ventricle 32 of heart 14. Another channel may include another R-wave amplifier that receives signals from electrodes 54 and 56, which are used for pacing and sensing proximate to left ventricle 36 of heart 14. In some examples, in one operating mode of sensing module 96, the R-wave amplifiers may take the form of an automatic gain controlled amplifier that provides an adjustable sensing threshold as a function of the measured R-wave amplitude of the heart rhythm.

In addition, in some examples, one channel of sensing module 96 may include a P-wave amplifier that receives signals from electrodes 58 and 60, which are used for pacing and sensing in right atrium 30 of heart 14. In some examples, in one operating mode of sensing module 96, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 96 may be selectively coupled to housing electrode 68, or elongated electrodes 72, 74, or 76, with or instead of one or more of electrodes 50, 52, 54, 56, 58 or 60, e.g., for unipolar sensing of R-waves or P-waves in any of chambers 30, 32, or 36 of heart 14.

In some examples, sensing module 96 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 92 as an EGM. In some examples, the storage of such EGMs in memory 92 may be under the control of a direct memory access circuit. Processor 90 may employ digital signal analysis techniques to characterize the digitized signals stored in memory 92 to detect and classify the patient's heart rhythm from the electrical signals. Processor 90 may detect and classify the heart rhythm of patient 12 by employing any of the numerous signal processing methodologies known in the art.

If ICD 16 is configured to generate and deliver pacing pulses to heart 14, processor 90 may include pacer timing and control module, which may be embodied as hardware, firmware, software, or any combination thereof. The pacer timing and control module may comprise a dedicated hardware circuit, such as an ASIC, separate from other processor 90 components, such as a microprocessor, or a software module executed by a component of processor 90, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided. When a pacing mode includes "D" as the third letter in the code, it may indicate that the atrial sense invokes a ventricular pace after a programmed sensed A-V interval.

Intervals defined by the pacer timing and control module within processor 90 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 96 to blank one or more channels, e.g., amplifiers, for a period during and after delivery of electrical stimulation to heart 14. The durations of these intervals may be determined by processor 90 in response to stored data in memory 92. The pacer timing and control module of processor 90 may also determine the amplitude of the cardiac pacing pulses.

During pacing, escape interval counters within the pacer timing/control module of processor 90 may be reset upon sensing of R-waves and P-waves. Stimulation generator 94 may include pacer output circuits that are coupled, e.g., selectively by a switching module, to any combination of electrodes 50, 52, 54, 56, 58, 60, 68, 72, 74, and 76 appropriate for delivery of a bipolar or unipolar pacing pulse to one of the chambers of heart 14. Processor 90 may reset the escape interval counters upon the generation of pacing pulses by stimulation generator 94, and thereby control the basic timing of cardiac pacing functions, including anti-tachyarrhythmia pacing.

The value of the count present in the escape interval counters when reset by sensed R-waves and P-waves may be used by processor 90 to measure the durations of R-R intervals, P-P intervals, P-R intervals and R-P intervals, which are measurements that may be stored in memory 92. Processor 90 may use the count in the interval counters to detect a tachyarrhythmia event, such as ventricular fibrillation event or ventricular tachycardia event. Upon detecting a threshold number of tachyarrhythmia events, processor 90 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, the count in the interval counters may not meet the requirements for triggering a therapeutic response.

In some examples, processor 90 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 90 and any updating of the values or intervals controlled by the pacer timing and control module of processor 90 may take place following such interrupts. A portion of memory 92 may be configured as a plurality of recirculating buffers, capable of holding series of measured intervals, which may be analyzed by processor 90 in response to the occurrence of a pace or sense interrupt to determine whether heart 14 of patient 12 is presently exhibiting atrial or ventricular tachyarrhythmia.

In some examples, an arrhythmia detection method may include any suitable tachyarrhythmia detection algorithms. In one example, processor 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 90 in other examples.

In the examples described herein, processor 90 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 92 of ICD 16. In addition, the number of tachyarrhythmia events that are detected to confirm the presence of a tachyarrhythmia episode may be stored as a number of intervals to detect (NID) threshold value in memory 92. In some examples, processor 90 may also identify the presence of the tachyarrhythmia episode by detecting a variability of the intervals between tachycardia events. For example, if the interval between successive tachyarrhythmia events varies by a particular percentage or the differences between the coupling intervals are higher than a given threshold over a predetermined number of successive cycles, processor 90 may determine that the tachyarrhythmia is present.

If processor 90 detects an atrial or ventricular tachyarrhythmia based on signals from sensing module 96, and an anti-tachyarrhythmia pacing regimen is desired, timing intervals for controlling the generation of anti-tachyarrhythmia pacing therapies by stimulation generator 94 may be loaded by processor 90 into the pacer timing and control module to control the operation of the escape interval counters therein and to define refractory periods during which detection of R-waves and P-waves is ineffective to restart the escape interval counters.

If ICD 16 is configured to generate and deliver defibrillation pulses to heart 14, stimulation generator 94 may include a high voltage charge circuit and a high voltage output circuit. In the event that generation of a cardioversion or defibrillation pulse is required, processor 90 may employ the escape interval counter to control timing of such cardioversion and defibrillation pulses, as well as associated refractory periods. In response to the detection of atrial or ventricular fibrillation or tachyarrhythmia requiring a cardioversion pulse, processor 90 may activate a cardioversion/defibrillation control module, which may, like pacer timing and control module, be a hardware component of processor 90 and/or a firmware or software module executed by one or more hardware components of processor 90. The cardioversion/defibrillation control module may initiate charging of the high voltage capacitors of the high voltage charge circuit of stimulation generator 94 under control of a high voltage charging control line.

Processor 90 may monitor the voltage on the high voltage capacitor, e.g., via a voltage charging and potential (VCAP) line. In response to the voltage on the high voltage capacitor reaching a predetermined value set by processor 90, processor 90 may generate a logic signal that terminates charging.

Thereafter, timing of the delivery of the defibrillation or cardioversion pulse by stimulation generator 94 is controlled by the cardioversion/defibrillation control module of processor 90. Following delivery of the fibrillation or tachycardia therapy, processor 90 may return stimulation generator 94 to a cardiac pacing function and await the next successive interrupt due to pacing or the occurrence of a sensed atrial or ventricular depolarization.

Stimulation generator 94 may deliver cardioversion or defibrillation pulses with the aid of an output circuit that determines whether a monophasic or biphasic pulse is delivered, whether housing electrode 68 serves as cathode or anode, and which electrodes are involved in delivery of the cardioversion or defibrillation pulses. Such functionality may be provided by one or more switches or a switching module of stimulation generator 94.

Telemetry module 98 includes any suitable hardware, firmware, software or any combination thereof for communicating with another device, such as programmer 24 (FIG. 1). Under the control of processor 90, telemetry module 98 may receive downlink telemetry from and send uplink telemetry to programmer 24 with the aid of an antenna, which may be internal and/or external. Processor 90 may provide the data to be uplinked to programmer 24 and the control signals for the telemetry circuit within telemetry module 98, e.g., via an address/data bus. In some examples, telemetry module 98 may provide received data to processor 90 via a multiplexer. Moreover, in some examples, processor 90 may cause telemetry module 98 to transmit a signal to INS 26 that is indicative of prospective therapy delivery by ICD 16, e.g., a signal that indicatives ICD 16 is about to deliver a stimulation signal to patient 12.

In some examples, processor 90 may transmit atrial and ventricular heart signals (e.g., EGM signals) produced by atrial and ventricular sense amp circuits within sensing module 96 to programmer 24. Programmer 24 may interrogate ICD 16 to receive the heart signals. Processor 90 may store heart signals within memory 92, and retrieve stored heart signals from memory 92. Processor 90 may also generate and store marker codes indicative of different cardiac episodes that sensing module 96 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. In some examples, data from sensing module 96 may be uploaded to a remote server, from which a clinician or another user may access the data to determine whether a potential sensing integrity issue exists. An example of a remote server includes the CareLink Network, available from Medtronic, Inc. of Minneapolis, Minn.

The various components of ICD 16 are coupled to power source 100, which may include a rechargeable or non-rechargeable battery. A non-rechargeable battery may be selected to last for several years, while a rechargeable battery may be inductively charged from an external device, e.g., on a daily or weekly basis.

FIG. 7A is a first functional block diagram of an example INS 26. INS 26 includes processor 110, memory 112, stimulation generator 114, switching module 116, telemetry module 118, and power supply 120. In the example shown in FIG. 7A, processor 110, memory 112, stimulation generator 114, switching module 116, telemetry module 118, and power supply 120 are enclosed within housing 27, which may be, for example a hermetic housing.

As shown in FIG. 7A, stimulation generator 114 is electrically coupled to leads 28 and 29 either directly or indirectly (e.g., via a lead extension). In the example illustrated in FIG. 7A, lead 28 includes electrodes 124A-124D (collectively referred to as "electrodes 124"). Lead 29 includes electrodes 126A-126D (collectively referred to as "electrodes 126"). Electrodes 124 and 126 may comprise ring electrodes. In other examples, electrodes 124 and 126 may be arranged in a complex electrode array that includes multiple non-contiguous electrodes at different angular positions about the outer circumference of leads 28 and 29, as well as different levels of electrodes spaced along a longitudinal axis of leads 28 and 29. The configuration, type, and number of electrodes 124 and 126 illustrated in FIG. 7A are merely one example. In other examples, INS 26 may be coupled to any suitable number of leads with any suitable number and configuration of electrodes. Moreover, leads 28 and 29 may comprise a shape other than a cylindrical shape. As an example, leads 28 and 29 may comprise a paddle-shaped portion that carries electrodes 124. In some examples, housing 27 of INS 26 may also include one or more electrodes.

In the example shown in FIG. 7A, lead 31 is electrically connected to housing 27 of INS 26 via clamping structure 123. Housing 27 may or may not be electrically coupled to stimulation generator 114 or other components shown in FIG. 7A. Lead 31 includes at least one electrode 125. In some examples, electrode 125 has a larger conductive surface area than that of any of the electrodes 124 and 126, or the combination of the conductive surface areas of electrodes 124 and 126. In other example, electrode 125 may have a substantially similar conductive surface area or a smaller conductive surface area as any of electrodes 124 and 126. In still another example, though not shown in FIG. 7A, rather than one electrode 125, lead 31 may comprise a plurality of electrodes similar to electrode 125. The plurality of electrodes may be connected to housing 27 via clamping structure 123. For example, each of the plurality of electrodes may be connected to one another via a wire, and the wire may be connected to clamping structure 123.

Electrode 125 may comprise a ring electrode, coil electrode, patch electrode, pad electrode or any other suitable type of electrode. In some examples, the surface area of electrode 125 may be ten times larger than the surface area of each of electrodes 124. That is, the ratio of the surface area of electrode 125 to each of electrodes 124 and 126 may be ten, although other ratio values are contemplated by this disclosure. In some examples, in addition to clamping structure 123, electrode 125 may be coupled to housing 27 via a resistor and/or resistive wire, or may be coupled to a heat sink component within housing 27, such as a conductor.

As shown in FIG. 7A, electrode 125 is not electrically connected to any stimulation or sensing circuitry of INS 26. For example, electrode 125 is not electrically connected to stimulation generator 114, and, therefore, may be considered to be a nontherapeutic electrode because electrode 125 is not used to deliver electrical stimulation therapy to patient 12 or sense electrical activity. In other examples, leads 28 or 29 may include electrode 125, and a conductor within the respective lead 28, 29 may electrically connect electrode 125 to housing 27 of INS 26.

As previously discussed, the delivery of cardiac rhythm therapy to heart 14 of patient 12 by ICD 16 may generate a voltage gradient in the patient's body. This voltage gradient may generate a flow of shunt-current through an electrical path including electrodes 124, 125, and 126. Surface area of electrode 125 may be used to minimize shunt-current flow into stimulation generator 114. Due to its relatively large conductive surface with respect to individual electrodes 124 and 126, electrode 125 may provide a lower impedance electrical path than the electrical path through therapeutic electrodes 124, 126. As a result of the lower impedance path, a larger percentage of shunt-current may flow into housing 27 or the heat sink components instead of flowing through electrodes 124, 126 into stimulation generator 114. In this way, larger amount of current may flow through the relatively large surface area electrode 125 to housing 27, minimizing the amount of current flowing from electrodes 124, 126 to stimulation generator 114. This may reduce the current density at the interface between electrodes 124, 126 and tissue of patient 12, which may reduce the stress to the tissue. In addition, diverting current flow to nontherapeutic electrode 125 may help reduce stress to the circuitry of stimulation generator 114.

As previously discussed, in some examples, nontherapeutic electrode 125 may comprise a substantially similar conductive surface area as electrodes 124, 126. In these examples, electrode 125 provides electrical paths for the shunt current in addition to the electrical paths through electrodes 124, 126. In this manner, some of the shunt current may be diverted from electrodes 124, 126 and may flow through nontherapeutic electrode 125 which may help reduce stress on the tissue of patient 12 and the circuitry of stimulation generator 114.

Upon activation, clamping structure 123 may provide a lower impedance electrical path for the shunt-current through electrode 125 to housing 27 than the electrical path through electrodes 124, 126 to circuitry within INS 26. Due to the lower impedance electrical path provided by electrode 125 and clamping structure 123 compared to the electrical path provided by electrodes 124, 126 to circuitry within INS 16, a substantial amount of the shunt-current may flow through electrode 125 and clamping structure 123 rather than flowing through electrodes 124, 125 to circuitry within INS 26. Clamping structure 123 activates when the voltage gradient sensed by electrode 125 is greater than a threshold voltage value, e.g., about 25 V to about 50 V, although other threshold voltage values are also contemplated. When there is no voltage gradient or when the voltage gradient sensed by electrode 125 is less than the threshold voltage value, clamping structure 123 remains deactivated and provides a relatively high impedance electrical path for electrical current compared to the electrical path when clamping structure 123 is activated.

In some examples, upon activation, clamping structure 123 may not provide a lower impedance electrical path for the shunt-current through electrode 125 to housing 27 than the electrical path through electrodes 124, 126 to circuitry within INS 26. In such examples, even though clamping structure 123 does not provide a lower impedance electrical path compared to the path through electrodes 124, 126, at least some of the shunt-current will be diverted from electrodes 124, 126 and will flow through clamping structure 123. In this manner, the amount of shunt-current that may flow through electrodes 124, 126 is reduced.

In some examples, clamping structure 123 may comprise at least one diode, at least one Zener diode (which permits current flow in two directions), a SCR and a resistor, a varistor, a gas plasma arrestor, or any combination thereof. Examples of clamping structure 123 are shown in FIGS. 8A-8D and described below. As shown in FIG. 7A, clamping structure 123 is external to lead 31 and housing 27. In other examples, clamping structure 123 may be enclosed within lead 31, housing 27, connector block 42 (FIG. 1) or otherwise electrically coupled to electrode 125.

In some examples, electrode 125 may be implanted within one of a subcutaneous layer, a sub-muscular location, and intravenous location of patient 12. Implanting the relatively low impedance electrode 125, e.g., low impedance compared to electrodes 124, 126, in the subcutaneous or sub-muscular tissue layer, or intravenously, may help reduce the possibility that shunt-current flowing through electrode 125 may undesirably stress tissue that is located proximate to electrode 125 because tissue within the subcutaneous or sub-muscular tissue layer may be less susceptible to stress from the localization of high density current than other types of tissue deeper than the subcutaneous tissue. However, in some examples, electrode 125 may be implanted within other tissue sites, such as submuscular tissue sites.

Memory 112 includes computer-readable instructions that, when executed by processor 110, cause INS 26 to perform various functions described herein. Memory 112 may include any volatile, non-volatile, magnetic, optical, or electrical media, such as a RAM, ROM, NVRAM, EEPROM, flash memory, or any other digital media. Memory 112 may store therapy programs, which may be stored in therapy program groups, and operating instructions. The therapy programs may define a particular program of therapy in terms of respective values for electrical stimulation parameters, such as electrode combination, electrode polarity, current or voltage amplitude, pulse width and pulse rate. A program group may comprise a plurality of therapy programs that may be delivered together on an overlapping or non-overlapping basis. The stored operating instructions may guide the general operation of INS 26 under control of processor 110, and may include instructions for measuring the impedance of electrodes 124.

Stimulation generator 114 generates stimulation signals, which may be pulses as primarily described herein, or continuous time signals, such as sine waves, for delivery to patient 12 via selected combinations of electrodes 124. Stimulation generator 114 generates an electrical stimulation signal based on the therapy program parameters. Stimulation generator 114 may be referred to as a signal generator because stimulation generator 114 generates and delivers electrical stimulation signals that provide electrical stimulation. As used herein, the term "stimulation generator" may be interchangeable with the term "signal generator." Processor 110 controls stimulation generator 114 according to stored therapy programs and/or program groups in memory 112 to apply particular stimulation parameter values specified by one or more of programs, such as amplitude, pulse width, and pulse rate. Processor 110 may include any one or more microprocessors, controllers, a DSPs, ASICs, FPGAs, or equivalent discrete or integrated digital or analog logic circuitry, and the functions attributed to processor 110 herein may be embodied as software, firmware, hardware or any combination thereof.

Processor 110 may also control switching module 116 to apply the stimulation signals generated by stimulation generator 114 to selected combinations of electrodes 124. In particular, switching module 116 couples stimulation signals to selected conductors within leads 28 and 29 which, in turn, deliver the stimulation signals across selected electrodes 124 and 126. Switching module 116 may include a switch array, switch matrix, multiplexer, or any other type of switching device suitable to selectively couple stimulation energy to selected electrodes. Hence, stimulation generator 114 is coupled to electrodes 124 and 126 via switching module 116 and conductors within leads 28 and 29. In some examples, INS 26 does not include switching module 116.

Stimulation generator 114 may be a single or multi-channel stimulation generator. In particular, stimulation generator 114 may be capable of delivering a single stimulation pulse, multiple stimulation pulses, or a continuous signal at a given time via a single electrode combination or multiple stimulation pulses at a given time via multiple electrode combinations. In some examples, however, stimulation generator 114 and switching module 116 may be configured to deliver multiple channels on a time-interleaved basis. In this case, switching module 116 serves to time division multiplex the output of stimulation generator 114 across different electrode combinations at different times to deliver multiple programs or channels of stimulation energy to patient 12.

Telemetry module 118 supports wireless communication between INS 26 and an external programmer 24 (FIG. 1) or another computing device, as well as between INS 26 and ICD 16 under the control of processor 110. Processor 110 of INS 26 may receive, as updates to programs, values for various stimulation parameters such as amplitude and electrode combination, from programmer 24 via telemetry module 118. The updates to the therapy programs may be stored within memory 112.

The various components of INS 26 are coupled to power supply 120, which may include a rechargeable or non-rechargeable battery. A non-rechargeable battery may be selected to last for several years, while a rechargeable battery may be inductively charged from an external device, e.g., on a daily or weekly basis. In other examples, power supply 120 may be powered by proximal inductive interaction with an external power supply carried by patient 12.

Figure 7B:
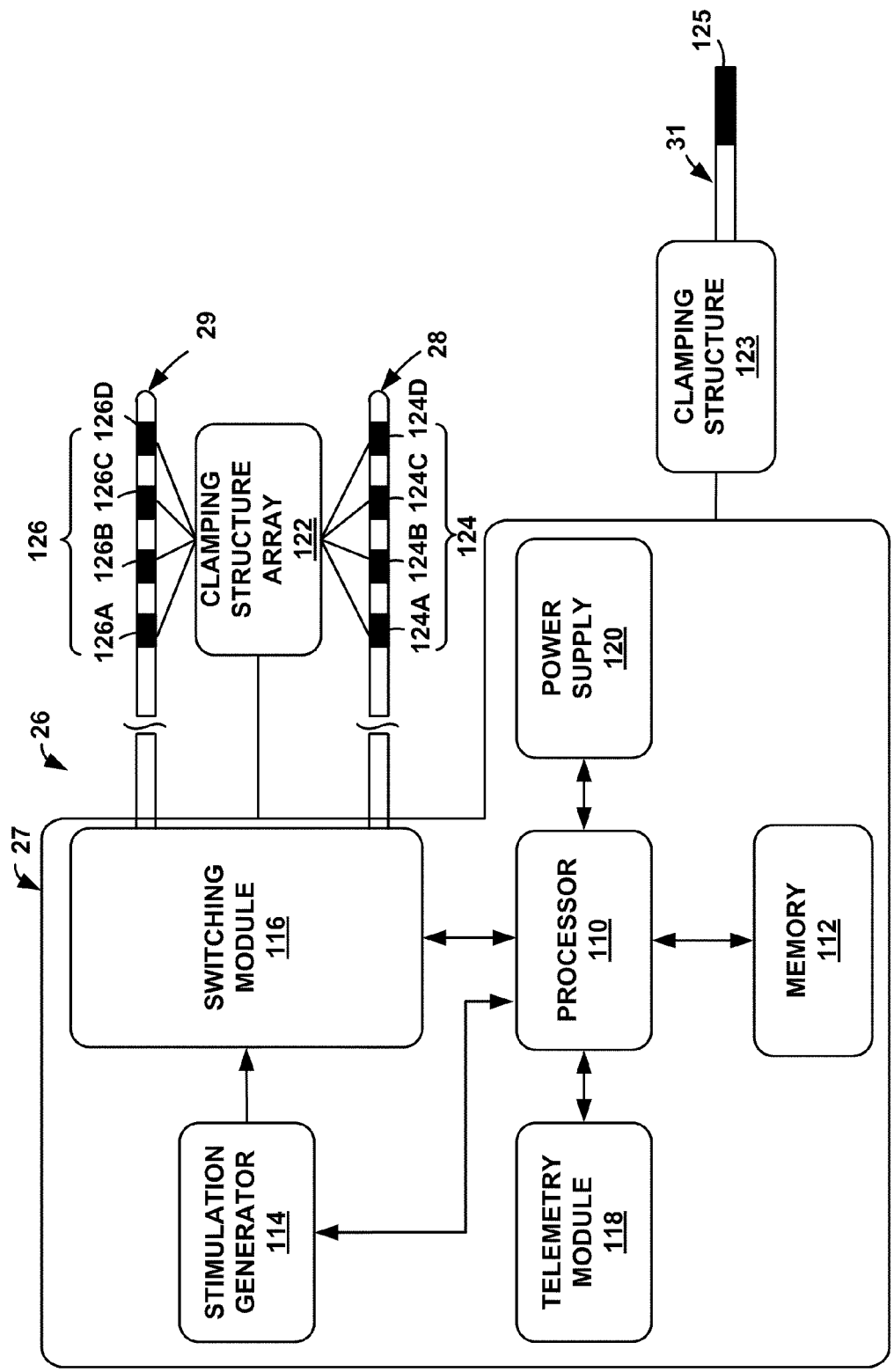
FIG. 7B is a second functional block diagram of an example INS that generates and delivers electrical stimulation signals to a target tissue site other than a heart of a patient.

FIG. 7B is a second functional block diagram of an example INS 26. As discussed with reference to FIG. 7A, INS 26 includes processor 110, memory 112, stimulation generator 114, switching module 116, telemetry module 118, and power supply 120. Furthermore, as shown in FIG. 7B, electrode 125 is coupled to INS 26 via clamping structure 123.

As shown in FIG. 7B, therapeutic electrodes 124, 126 are coupled to clamping structure array 122, which may comprise at least one clamping structure similar to clamping structure 123. Clamping structure array 122 provides shunt-current mitigation to the circuitry within INS 26 in addition to electrode 125 and clamping structure 123. In particular, clamping structure array 122 electrically decouples electrodes 124, 126 from stimulation generator 114 and, in the example shown in FIG. 7A, electrically connects electrodes 124, 126 to housing 127 when a voltage gradient at electrodes 124 or 126 is greater than or equal to a threshold voltage value. In this way, the shunt-current that is introduced into stimulation generator 114 from electrodes 124, 126 may be reduced when the voltage at one or more of the electrodes 124, 126 is greater than or equal to a threshold voltage value.

In some examples, clamping structure array 122 may be designed such that the threshold voltage value for activating clamping structure array 122 is greater than the threshold voltage value for activating clamping structure 123, which is electrically connected to nontherapeutic electrode 125. For example, clamping structure 123 may activate when the voltage gradient sensed by electrode 125 is greater than or equal to 25 V, and the clamping structure within clamping structure array 122 may activate when the voltage gradient at electrodes 124 or 126 is greater than or equal to about 27 V to about 100 V.

As shown in FIG. 7B, in one example, clamping structure array 122 is electrically connected to housing 27. Housing 27 provides a common coupling node for electrodes 124, 126. Each of the clamping structures within clamping structure array 122 may couple each one of electrodes 124, 126 to housing 27. For example, electrode 124A may be coupled to housing 27 via a first clamping structure within clamping structure array 122, electrode 126A may be coupled to housing 27 via a second clamping structure within clamping structure array 122, electrode 124B may be coupled to housing 27 via a third clamping structure within clamping structure 122, and so on.

Each of the clamping structures with clamping structure array 122 may activate when the voltage gradient is greater than or equal to a threshold voltage value. Upon activation, the clamping structures within clamping structure array 122 may reduce the shunt-current from flowing into circuitry within INS 26, e.g., stimulation generator 114 of INS 26. The clamping structures within clamping structure array 122 may divert the shunt-current into housing 27 thereby reducing the shunt-current flowing into circuitry within INS 26. In such examples, clamping structures within clamping structure array 122 may provide additional shunt-current mitigation in addition to the shunt-current mitigation provided by clamping structure 123. In some examples, the clamping structures within clamping structure array 122 may activate at different threshold voltages.

As previously discussed, clamping structure 123 diverts a substantial amount of the shunt-current from flowing into circuitry within INS 26, e.g., stimulation generator 114 of INS 26. Clamping structure 123 allows the substantial amount of shunt-current to flow into housing 27 thereby diverting the shunt-current from circuitry within INS 26. However, if the voltage of the voltage gradient is very high, e.g., greater than 50 V, the current that may flow through electrodes 124 or electrodes 126 into INS 26, e.g., the total amount of shunt-current minus the amount of shunt-current diverted through clamping structure 123, may potentially stress circuitry within INS 26. Clamping structures within clamping structure array 122 may cause the current that flows through electrodes 124 or electrodes 126 to flow into housing 27 rather than circuitry within INS 26.

In other examples, each of the clamping structures within clamping structure array 122 may couple each of electrodes 124 to each one of electrodes 126. For example, a first clamping structure within clamping structure array 122 may couple electrode 124A to electrode 126A, a second clamping structure within clamping structure array 122 may couple electrode 124B to electrode 126B, a third clamping structure within clamping structure array 122 may couple electrode 124C to electrode 126C, and so on. In such examples, the connection between clamping structure array 122 and housing 27 may not be necessary.

In examples where each of the clamping structures couple each of electrodes 124 to each one of electrodes 126, clamping structures within clamping structure array 122 may provide additional shunt-current mitigation in addition to clamping structure 123 and electrode 125. The voltage of the voltage gradient sensed by electrodes 124 may be different than the voltage of the voltage gradient sensed by electrodes 126 due to the tissue impedance between the electrodes 124 and electrodes 126. If the sensed voltage between electrodes 124 and electrodes 126 is greater than the threshold voltage value, the clamping structures may activate. Upon activation, the clamping structures may divert the shunt-current from flowing into stimulation generator 114 within the INS 26. The clamping structures may cause the shunt-current to flow between leads 28 and 29.

Although clamping structure 122 is external to INS 26 in the example shown in FIG. 7B, in other examples clamping structure array 122 may be enclosed within INS 26. Furthermore, in some cases, a therapy system may not include clamping structure array 122, which provides shunt-current mitigation in addition to clamping structure 123. In such examples, electrode 125 and clamping structure 123 may provide sufficient shunt-current mitigation.

Though not shown in FIGS. 7A and 7B, in some examples, each one of electrodes 124 of lead 28 may be coupled to at least one other electrode 124 via clamping structures. Similarly, each one of electrodes 126 of lead 29 may be coupled to at least one other electrode 126 via clamping structures. The clamping structures may be substantially similar to clamping structure 123. For example, electrode 124A may be coupled to electrode 124B, 124C, and 124D via clamping structures. Similarly, electrode 124B may be coupled to electrode 124C and 124D via clamping structures, and so on. However, clamping structures that couple each one of electrodes 124 to all other electrodes 124 may not be necessary. Also, clamping structures that couple each one of electrodes 126 to all other electrodes 126 may not be necessary.

It should be noted that, in some examples, each of electrodes 124, 126 is capable of delivering electrical stimulation therapy to patient 12, but the user may program only a few of the electrodes, e.g., electrodes 124A, 124B, 126A, and 126B, to be therapeutic electrodes. The remaining electrodes, e.g., 124C, 124D, 126C, and 126D may be programmed to act as nontherapeutic electrodes. The nontherapeutic electrodes may reduce shunt-current density at the therapeutic electrodes by providing additional surface area, rather than delivering electrical stimulation therapy to patient 12.

Figure 7C:
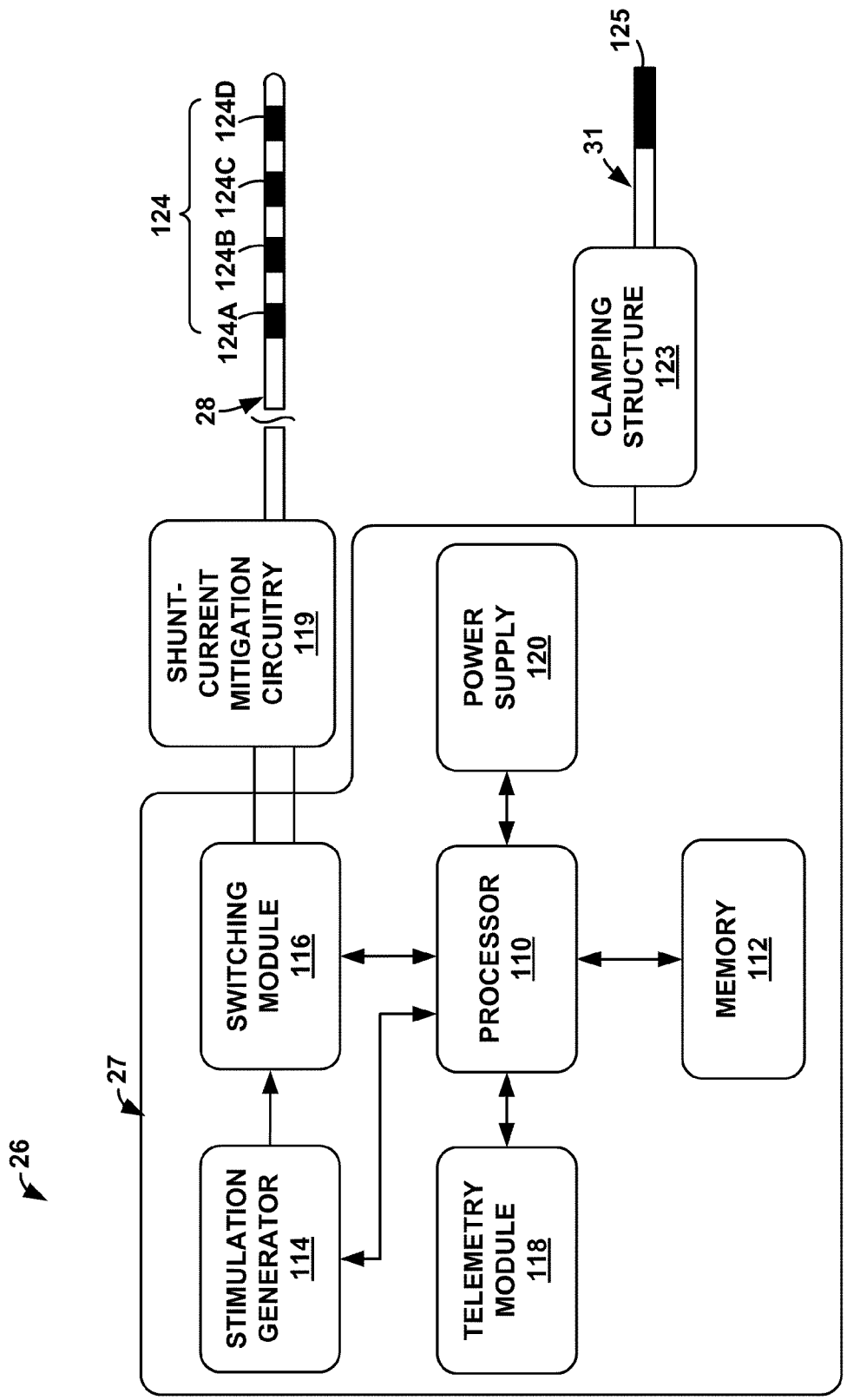
FIG. 7C is a third functional block diagram of an example INS that generates and delivers electrical stimulation signals to a target tissue site other than a heart of a patient.

FIG. 7C is a third functional block diagram of an example INS 26. As discussed with reference to FIGS. 7A and 7B, INS 26 includes processor 110, memory 112, stimulation generator 114, switching module 116, telemetry module 118, and power supply 120. Furthermore, as shown in FIG. 7C, electrode 125 is coupled to INS 26 via clamping structure 123.

As shown in FIG. 7C, stimulation generator 114 is electrically coupled to lead 28 via shunt-current mitigation circuitry 119. For purposes of clarity, lead 29 shown in FIGS. 7A and 7B is not shown in FIG. 7C. In examples that include additional leads, e.g., lead 29, stimulation generator 114 may be coupled to the electrodes of the additional leads via shunt-current mitigation circuitry that is substantially similar to shunt-current mitigation circuitry 119. Shunt-current mitigation circuitry 119 may be coupled to lead 28 either directly or indirectly (e.g., via a lead extension). Alternatively, shunt-current mitigation circuitry 119 may be coupled to more than one lead directly or indirectly (e.g., via a lead extension, such as a bifurcating lead extension that may electrically and mechanically couple to two leads) as needed to provide neurostimulation therapy to patient 12. In some examples, a lead body of lead 28 may comprise shunt-current mitigation circuitry 119. Although FIG. 7C illustrates an example in which shunt-current mitigation circuitry 119 is external to housing 27, e.g. external to INS 26, aspects of this disclosure are not so limited. In some examples, shunt-current mitigation circuitry 119 may be enclosed within housing 27 and electrically coupled to stimulation generator 114. In some examples, a connector, e.g. connector 42 (FIG. 1), coupled to INS 26 that is used to electrically and mechanically connect lead 28 to stimulation generator may comprise shunt-mitigation circuitry 119.

In the example illustrated in FIG. 7C, each of the electrodes 124 of lead 28 may be electrically coupled to the stimulation generator 114 via shunt-current mitigation circuitry 119. That is, shunt-current mitigation circuitry 119 is located between stimulation generator 114 and electrodes 124. In general, shunt-current mitigation circuitry 119 may help limit the passage of shunt-current through an electrical path including electrodes 124, conductors within lead 28, and stimulation generator 114. In examples in which INS 26 includes a sensing module (not shown in FIG. 7C) for sensing one or more physiological parameters of patient 12 (e.g., ECG signals) via electrodes 124, shunt-current mitigation circuitry 119 may be electrically coupled to the sensing module and electrodes 124.

As previously discussed, the delivery of cardiac rhythm therapy to heart 14 of patient 12 by ICD 16 may generate a voltage gradient in the patient's body. This voltage gradient may generate a flow of shunt-current through an electrical path including electrodes 124, 125. Shunt-current mitigation circuitry 119 may reduce the shunt-current that flows through the electrical path by increasing the impedance of the electrical path including electrodes 124. In this way, shunt-current mitigation circuitry 119 may reduce the current density at the interface between electrodes 124 and tissue, which may help reduce stresses imposed on the tissue. In addition, increasing the impedance of the electrical path including electrodes 124 may help prevent the inadvertent stimulation of tissue that may be disposed between ICD 16 and electrodes 124 by, for example, decreasing the possibility that current with the ability to stimulate tissue (e.g., because of the amplitude of the current) may flow through the tissue. This may help prevent the inadvertent stimulation of tissue that is not intended to be stimulated.

Examples of shunt-current mitigation circuitry 119 include, but are not limited to, a resistor, a resistive wire, a switch, a current limiter, and a monitor coupled to the switch that monitors one or more electrical parameter values at electrodes 124. Examples of shunt-mitigation circuitry 119 are described in further detail with respect to FIGS. 11-15. As described in more detail with respect to FIG. 11, shunt-current mitigation circuitry 119 may comprise a plurality of resistors and/or resistive wires. The resistors and/or resistive wires provide a high impedance path for the shunt-current thereby reducing the amount of shunt-current that may flow through electrodes 124 into circuitry within INS 26. As also described below with respect to FIG. 11, in some examples, shunt-current mitigation circuitry 119 comprises a plurality of switches where each switch is in parallel with each resistor and/or resistive wire. As described below with respect to FIG. 12, shunt-current mitigation circuitry 119 may comprise a plurality of diodes, such as transient absorber diodes, Zener diodes, or high voltage diodes. The diodes may allow current to flow in one direction, and limit the amount of current that may flow in the opposite direction. In some examples, the diodes are leaky diodes that may allow a certain amount of current to leak through so that the charge on the electrodes is balanced. A leaky diode may be realized, in some examples, by using a non-leaky regular diode connected in parallel with a high impedance resistor, e.g., about 1 mega-ohm to 100 mega-ohms.

Figure 13:
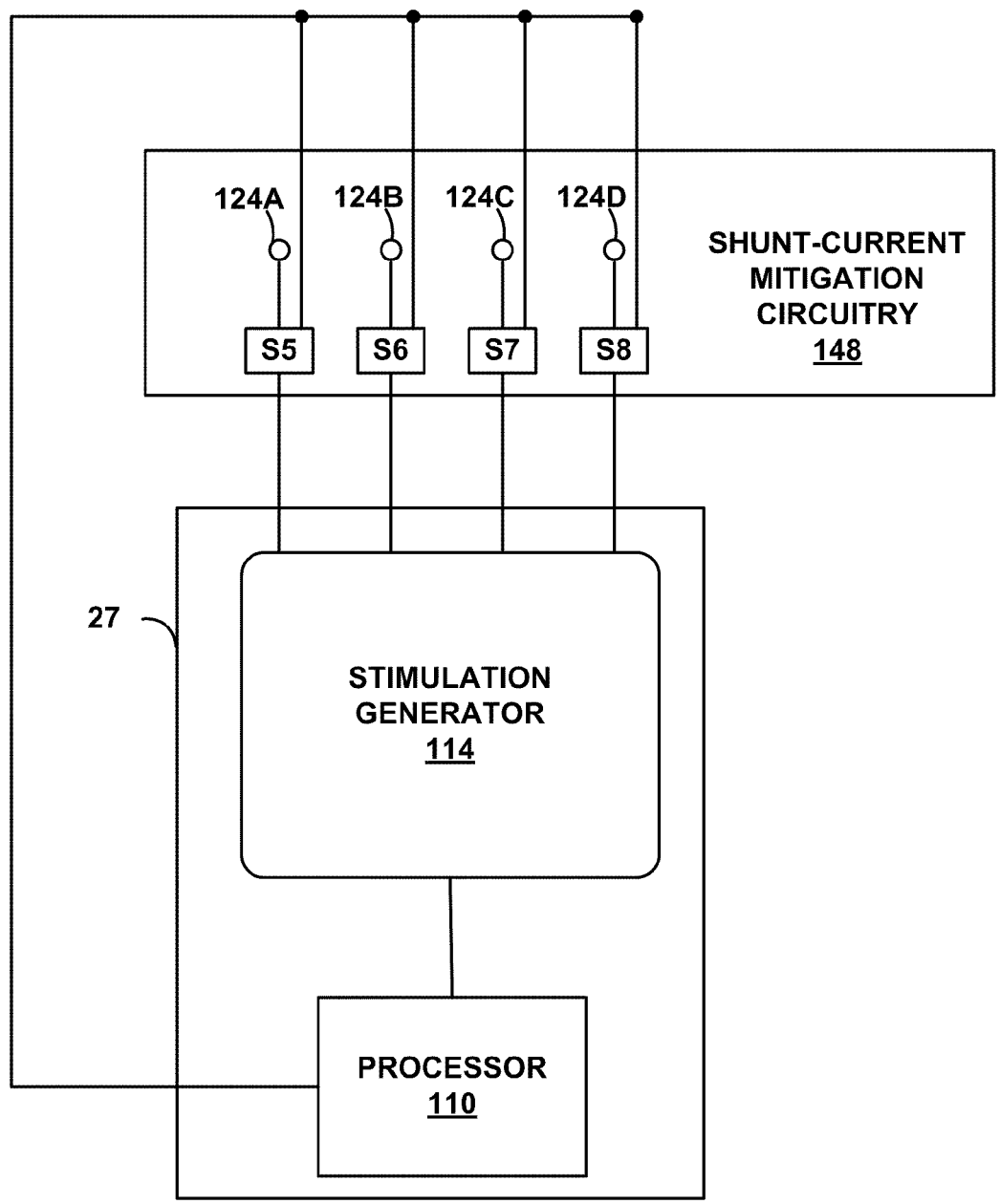
FIG. 13 is a block diagram illustrating another example IMD that includes shunt-current mitigation components.

As described with respect to FIG. 13, shunt-current mitigation circuitry 119 may comprise a plurality of switches that toggle open to generate a high impedance path for the shunt-current thereby reducing the amount of shunt-current that may flow through electrodes 124 into circuitry within INS 26. The switches may be opened in response to receiving a communication signal from ICD 16 (FIG. 1) indicative of prospective therapy delivery by ICD 16. As described in more detail with respect to FIG. 14, shunt-current mitigation circuitry 119 may also comprise a plurality of switches and one or more monitors. The monitors may monitor a voltage or current at electrodes 124. If the voltage or current exceeds a threshold value, the switches may toggle open to create a high impedance path for the shunt-current thereby reducing the amount of shunt-current that may flow through electrodes 124 into circuitry within INS 26. In addition, using multiple switches connected in series, and in some examples with resistors across each switch, may increase the ability to switch at higher voltages. As described in more detail with respect to FIG. 15, shunt-current mitigation circuitry 119 may also comprise a plurality of current limiters such as fuses, bimetallic circuit breakers, and the like. Current limiters may limit the amount of current that may flow through electrodes 124. Accordingly, if the shunt-current is greater than the limit of the current limiters, the current limiters may limit the amount of shunt-current that may flow from electrodes 124.

Figure 8A:
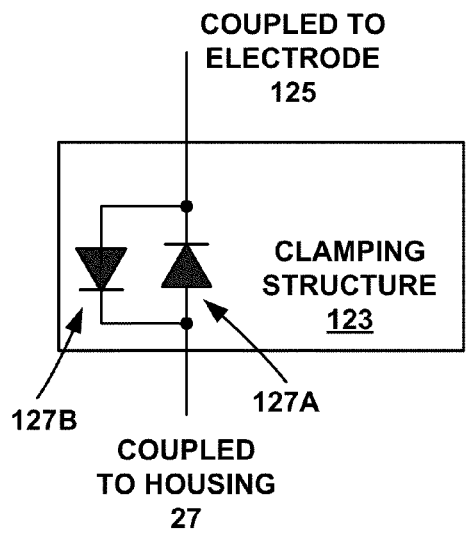
FIGS. 8A-8E are circuit diagrams of example clamping structures that may be coupled to the INS shown in FIGS. 7A and 7B.

FIGS. 8A-8E are circuit diagrams of example clamping structures 123 (FIGS. 7A, 7B, and 7C), which may be electrically connected to nontherapeutic electrode 125 and coupled to housing 27. As shown in FIG. 8A, in one example, clamping structure 123 comprises diodes 127A and 127B. Diodes 127A and 127B may provide a lower impedance current path for the shunt current compared to the current path through electrodes 124, 126 when the voltage gradient sensed by electrode 125 is greater than approximately 0.7 V or less than approximately −0.7 V. If the voltage gradient sensed by electrode 125 is between 0.7 V and −0.7 V, both diodes 127A and 127B may be considered as deactivated. In the deactivated state, little to no current may flow through diodes 127A and 127B.

If the voltage gradient sensed by electrode 125 is greater than 0.7 V, diode 127A remains deactivated and diode 127B becomes activated. Upon activation, diode 127B may provide a lower impedance current path to housing 27 compared to the current path to INS 26 through electrodes 124, 126, in some examples. If the voltage gradient sensed by electrode 125 is less than −0.7 V, diode 127B remains deactivated and diode 127A becomes activated. Upon activation, diode 127A may provide a lower impedance current path from housing 27 compared to the current path from INS 26 through electrodes 124, 126, in some examples.

In some other examples, rather than providing a lower impedance current path to housing 27 compared to the current path to INS 26 through electrodes 124, 126, upon activation, diodes 127A and 127B may provide the shunt-current a substantially similar impedance current path to housing 27 or a higher impedance current path to housing 27. Even in such instances, at least some of the shunt-current may flow through diode 127A or 127B thereby reducing the amount of shunt-current that flows through electrodes 124, 126.

As shown in FIG. 8A, diodes 127A and 127B provide symmetrical activation capability. In other words, clamping structure 123, as shown in FIG. 8A, activates if the voltage gradient sensed by electrode 125 is greater than a positive threshold voltage and activates if the voltage gradient sensed by electrode 125 is less than a negative threshold voltage. In some examples, rather than symmetrical activation capability, clamping structure 123 may only activate if the voltage gradient sensed by electrode 125 is greater than a positive threshold voltage. In such examples, diode 127A may be unnecessary. Similarly, in some examples, clamping structure 123 may only activate if the voltage gradient sensed by electrode 125 is less than a negative threshold voltage. In such examples, diode 127B may be unnecessary.

Furthermore, as described above, clamping structure 123, as shown in FIG. 8A, activates if the voltage gradient is less than −0.7 V or greater than 0.7 V. In this example, the threshold voltage for activating clamping structure 123 is 0.7 V and −0.7 V. In one example, to increase or decrease the threshold voltage that activates clamping structure 123, many diodes substantially similar to diodes 127A and 127B may be connected in series. To increase the positive threshold voltage that activates clamping structure 123, diodes similar to diode 127B may be connected in series, i.e., the cathode of a diode may be connected in series to the anode of another diode. Similarly, to increase the absolute value of the negative threshold voltage that activates clamping structure 123, diodes similar to diode 127A may be connected in series, i.e., the cathode of a diode may be connected in series to the anode of another diode. For example, 100 diodes substantially similar to diode 127B may be connected in series (cathode to anode series connection) to increase the positive threshold voltage to 70 V. In this example, if the voltage gradient sensed by electrode 125 is greater than 70 V, the diodes may provide a lower impedance current path to housing 27 than the current path through electrodes 124, 126 to INS 26. Similarly, 100 diodes substantially similar to diode 127A may be connected in series to increase the absolute value of the negative threshold voltage to 70 V. In this example, if the voltage gradient sensed by electrode 125 is less than −70 V, the diodes may provide a lower impedance current path to housing 27 than the current path through electrodes 124, 126 to INS 26.

Figure 8B:
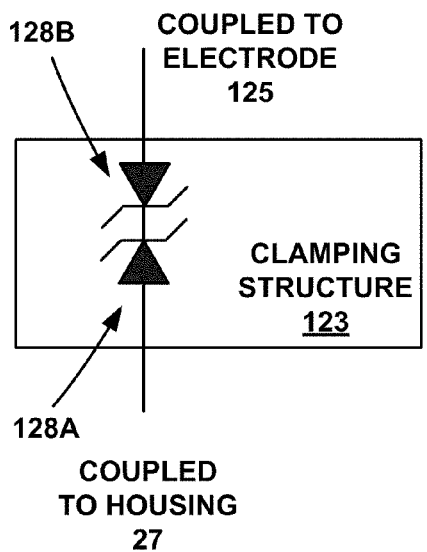

As shown in FIG. 8B, in one example, clamping structure 123 may comprise Zener diodes 128A and 128B. As shown in FIG. 8B, the cathode of Zener diode 128A is connected to the cathode of Zener diode 128B. In FIG. 8B, Zener diodes 128A and 128B provide a high impedance path if the voltage gradient sensed by electrode 125 is positive and less than the breakdown voltage of Zener diode 128B. If the voltage gradient sensed by electrode 125 is greater than a breakdown voltage of Zener diode 128A, Zener diodes 128A and 128B may allow current to flow from electrode 125 to housing 27. Accordingly, when electrode 125 senses a positive voltage gradient greater than the breakdown voltage for Zener diode 128A, Zener diode 128A and 128B may provide a lower impedance electrical path for the shunt-current to flow from electrode 125 to housing 27, compared to an electrical path through electrodes 124, 126 into circuitry within INS 26.

Similarly, in FIG. 8B, Zener diodes 128A and 128B provide a high impedance path if the voltage gradient sensed by electrode 125 is negative and the absolute value of the voltage gradient is less than the breakdown voltage of Zener diode 128A. Conversely, if the voltage gradient sensed by electrode 125 is negative and the absolute value of the voltage gradient is greater than a breakdown voltage of Zener diode 128B, Zener diodes 128A and 128B may allow current to flow from electrode 125 to housing 27 thereby diverting at least some of the shunt-current away from electrodes 124, 126.

Due to the lower impedance electrical path through Zener diode 128A and 128B compared to the electrical path through electrodes 124, 126, a substantial amount of the shunt-current may flow through electrode 125 and Zener diode 128A and 128B into housing 27 rather than through electrodes 124, 126 into circuitry within INS 26 thereby minimizing the shunt-current that flows to the circuitry within INS 26 and the tissue proximate to leads 28 and 29.

Similar to the description with respect to FIG. 8A, in some examples, the activation of Zener diode 128A or 128B may not provide a lower impedance electrical path for the shunt-current compared to the electrical path through electrodes 124, 126. However, even in such examples, the amount of the shunt-current that flows through electrodes 124, 126 may be reduced. The activation of Zener diode 128A or 128B provides additional paths for the shunt-current in addition to the paths through electrodes 124, 126. Accordingly, some of the shunt-current is diverted from electrodes 124, 126 and flows through Zener diodes 128A and 128B even in examples where the electrical path through Zener diodes 128A and 128B is not necessarily of a lower impedance compared to the electrical path through electrodes 124, 126.

Although not shown in FIG. 8B, in some examples, multiple Zener diodes may be coupled in series to provide a higher breakdown voltage. For example, two Zener diodes substantially similar to Zener diode 128A and two Zener diodes substantially similar to diode 128B may be coupled in series to provide a breakdown voltage of 50 V or −50V. To connect Zener diodes in series, the anode of one Zener diode may be connected to the cathode of another Zener diode. In this example, clamping structure 123 comprises four Zener diodes. The first and second Zener diodes may be connected in series, i.e., the cathode of the first Zener diode may be connected to the anode of the second Zener diode. The anode of the first Zener diode may be connected to electrode 125. The third and fourth Zener diodes may be connected in series, i.e., the anode of the third Zener diode may be connected to the cathode of the fourth Zener diode. The cathode of the third Zener diode may be connected to the cathode of the second Zener diode. The anode of the fourth diode may be connected to housing 27.

Though not shown in FIG. 8B, in some examples, rather than or in addition to Zener diodes, two transient voltage suppression diodes, connected with opposite polarity, may be connected in a similar fashion as described above with respect to the Zener diodes shown in FIG. 8B. In another example, a single component such as a bidirectional conducting diode for alternating current, or DIAC, may be used.

As shown in FIG. 8B, the cathode of Zener diode 128B is connected to the cathode of Zener diode 128A. In an alternate example, the anode of Zener diode 128B may be connected to the anode of Zener diode 128A. In this example, the cathode of Zener diode 128B may be coupled to electrode 125, and the cathode of Zener diode 128A may be coupled to housing 27. In this example, if the voltage gradient sensed by electrode 125 is positive and is greater than the breakdown voltage of Zener diode 128B, Zener diodes 128A and 128B may provide a lower impedance electrical path compared to the electrical path through electrodes 124, 126. Similarly, if the voltage gradient sensed by electrode 125 is negative and the absolute value of the voltage gradient is greater than the breakdown voltage of Zener diode 128B, Zener diodes 128A and 128B may provide a lower impedance electrical path compared to the electrical path through electrodes 124, 126.

Similar to FIG. 8A, as shown in FIG. 8B, Zener diodes 128A and 128B provide symmetrical activation capability. Clamping structure 123, as shown in FIG. 8B, activates if the voltage gradient sensed by electrode 125 is greater than a positive threshold voltage and activates if the voltage gradient sensed by electrode 125 is less than a negative threshold voltage. In some examples, rather than symmetrical activation capability, clamping structure 123 may only activate if the voltage gradient sensed by electrode 125 is greater than a positive threshold voltage. In such examples, Zener diode 128B may be unnecessary. Similarly, in some examples, clamping structure 123 may only activate if the voltage gradient sensed by electrode 125 is less than a negative threshold voltage. In such examples, diode 128A may be unnecessary.

Figure 8C:
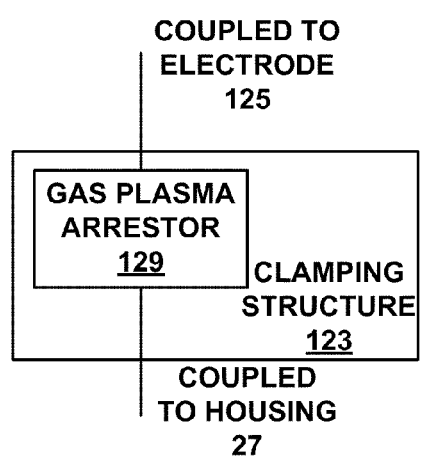

As shown in FIG. 8C, in one example, clamping structure 123 may comprise gas plasma arrestor 129, also known as a gas discharge tube. If the voltage gradient sensed by electrode 125 is greater than a threshold voltage, gas plasma arrestor 129 may activate and diver the shunt-current from flowing into electrodes 124 and 126. Gas plasma arrestor may be two electrodes in close proximity within a gas environment. When the voltage gradient sensed by electrode 125 exceeds a threshold voltage, the gas ionizes and activates gas plasma arrestor 129.

Upon activation, gas plasma arrestor 129 may provide a lower impedance electrical path for the shunt-current to flow from electrode 125 to housing 27, compared to an electrical path for the shunt-current to flow from electrodes 124, 126 into the circuitry within INS 26. Due to the lower impedance electrical path through gas plasma arrestor 129 compared to the electrical path through electrodes 124, 126, a substantial amount of the shunt-current may flow through electrode 125 and gas plasma arrestor 129 into housing 27 thereby minimizing the shunt-current that flows into the circuitry within INS 26 and tissue proximate to leads 28 and 29 via electrodes 124, 126. Although not shown in FIG. 8C, in some examples, multiple gas plasma arrestors, substantially similar to gas plasma arrestor 129, may be coupled in series. When coupled in series, the threshold voltage that may trigger the gas plasma arrestor may be greater than the threshold voltage that triggers any stand alone gas plasma arrestor, e.g., a gas plasma arrestor not in series with other gas plasma arrestors.

In some examples, clamping structure 123 may comprise a hybrid gas plasma overvoltage protector. The hybrid gas plasma overvoltage protector comprises a gas plasma arrestor and two silicone avalanche diodes (SADs). The SADs may be coupled in parallel to the gas plasma arrestor and may provide fast clamping action, i.e., may activate quickly when the voltage gradient sensed by electrode 125 exceeds a threshold voltage.

Similar to the description with respect to FIGS. 8A and 8B, in some examples, the activation of gas plasma arrestor 129 may not provide a lower impedance electrical path for the shunt-current compared to the electrical path through electrodes 124, 126. However, even in such examples, the amount of the shunt-current that flows through electrodes 124, 126 may be reduced. The activation of gas plasma arrestor 129 provides additional paths for the shunt-current in addition to the paths through electrodes 124, 126. Accordingly, some of the shunt-current is diverted from electrodes 124, 126 and flows through gas plasma arrestor even in examples where the electrical path through gas plasma arrestor is not necessarily of a lower impedance compared to the electrical path through electrodes 124, 126.

Figure 8D:
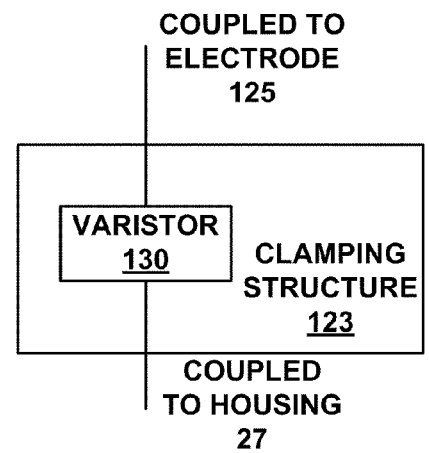

As shown in FIG. 8D, in one example, clamping structure 123 may comprise varistor 130. In some examples, varistor 130 may be a metal oxide varistor (MOV). Similar to the gas plasma arrestor of FIG. 8C, if the voltage gradient sensed by electrode 125 is greater than a threshold voltage, varistor 130 may activate and divert the shunt-current from flowing into electrodes 124 and 126. Upon activation, varistor 130 may provide a lower impedance electrical path for the shunt-current to flow from electrode 125 to housing 27, compared to an electrical path through electrodes 124, 126 into the circuitry within INS 26. Again, due to the lower impedance electrical path through varistor 130 compared to the electrical path through electrodes 124, 126, a substantial amount of the shunt-current may flow through electrode 125 and varistor 130 into housing 27 thereby minimizing the shunt-current that flows into the circuitry within INS 26 and tissue proximate to leads 28 and 29. Similar to FIG. 8C, although not shown in FIG. 8D, in some examples, multiple varistors, substantially similar to varistor 130, may be coupled in series. When coupled in series, the threshold voltage that may trigger the varistors may be greater than the threshold voltage that triggers any stand alone varistor, e.g., a varistor not in series with other varistors.

Similar to the description with respect to FIGS. 8A, 8B, and 8C, in some examples, the activation of varistor 130 may not provide a lower impedance electrical path for the shunt-current compared to the electrical path through electrodes 124, 126. However, even in such examples, the amount of the shunt-current that flows through electrodes 124, 126 may be reduced. The activation of varistor 130 provides additional paths for the shunt-current in addition to the paths through electrodes 124, 126. Accordingly, some of the shunt-current is diverted from electrodes 124, 126 and flows through varistor 130 even in examples where the electrical path through varistor 130 is not necessarily of a lower impedance compared to the electrical path through electrodes 124, 126.

Figure 8E:
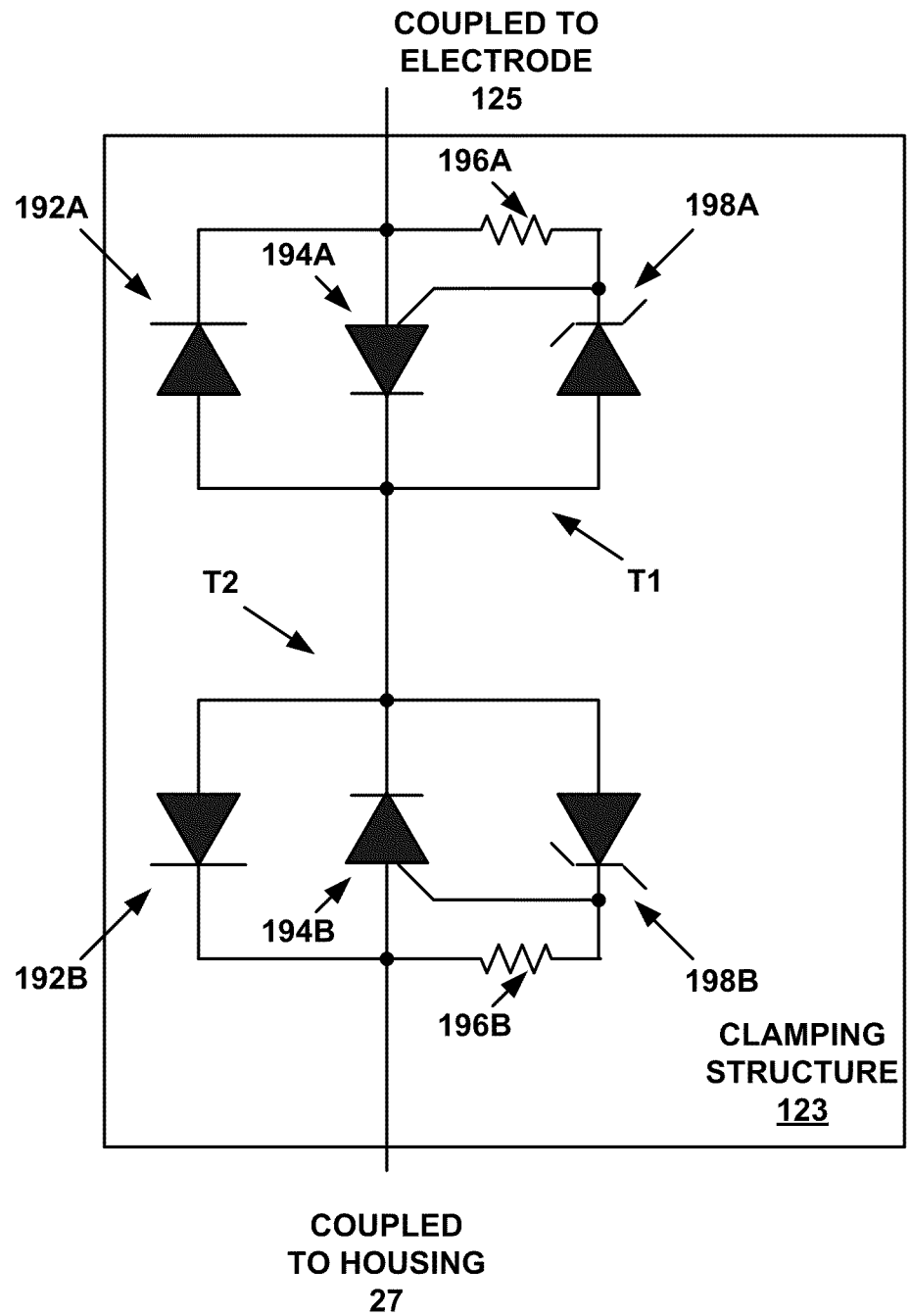

As shown in, FIG. 8E, in one example, clamping structure 123 may comprise diodes 192A and 192B, silicone controlled rectifiers (SCRs) 194A and 194B, resistors 196A and 196B, and Zener diodes 198A and 198B. As shown in FIG. 8E, circuit T1 comprises diode 192A, SCR 194A, resistor 196A, and Zener diode 198A. Circuit T2 comprises diode 192B, SCR 194B, resistor 196B, and Zener diode 198B. During an initial state, i.e., when there is no voltage gradient for electrode 125 to sense, circuits T1 and T2 are deactivated and are at relatively high impedance. As the voltage gradient starts increasing, e.g., approaches and is about to exceed 12 V, the voltage across circuit T1 is more greater than the voltage across circuit T2, the conductive path for any shunt-current is through resistor 196A, Zener diode 198A, and diode 192B. When the voltage exceeds approximately 10 V relative to housing 27, as one non-limiting example, Zener diode 198A activates and a portion of the shunt-current flows through Zener diode 198A, resistor 196A, and diode 192B. Current flowing through resistor 196A causes a voltage drop across resistor 196A. When the voltage gradient level is approximately 10 V but less than 12 V, the voltage drop across resistor 196A is less than approximately 0.7 V. As the voltage gradient increases to approximately 12 V, the voltage drop across resistor 196A reaches approximately 0.7 V to 2 V.

A voltage drop of approximately 0.7 V to 2 V activates SCR 194A. The activation of SCR 194A causes a forward voltage drop of approximately 0.7 V. The activation of SCR 194A causes Zener diode 198A to deactivate because the voltage drop across Zener diode 198A is no longer greater than 10 V, but is rather approximately 0.7 V. After Zener diode 198A deactivates, the voltage drop across circuits T1 and T2 is approximately 1.4 V, i.e., 0.7 V drop across SCR 194A and 0.7 V diode 192B. In this example, clamping structure 123 may provide a lower impedance electrical path for the shunt-current through electrode 125 compared to the electrical path through electrodes 124, 126 when the voltage gradient is greater than approximately 1.4 V.

The example clamping structure 123 shown in FIG. 8E provides some amount of hysteresis. The clamping structure 123 activates when the voltage gradient is greater than approximately 10 V, and when the voltage gradient exceeds approximately 12 V, SCR 194A activates. When the voltage is greater than 10 V, clamping structure 123 may provide a lower impedance electrical path for the shunt-current to flow through electrode 125 compared to the electrical path through electrodes 124, 126. Notably, after activation of SCR 194A, the clamping structure 123 as shown in FIG. 8E, may provide a lower impedance electrical path through electrode 125 compared to the electrical path through electrodes 124, 126 as long as the voltage gradient is greater than approximately 1.4 V. The 10 V, 12 V, and 1.4 V values are provided only for illustration purposes. In some examples, the threshold voltage that activates clamping structure 123, as shown in FIG. 8E, may be 18 V.

Similar to FIGS. 8A and 8B, circuits T1 and T2 provide symmetrical activation capability. Clamping structure 123, as shown in FIG. 8E, activates if the voltage gradient sensed by electrode 125 is greater than a positive threshold voltage and activates if the voltage gradient sensed by electrode 125 is less than a negative threshold voltage. For example, if the voltage gradient sensed by electrode 125 is approximately −10 V than Zener diode 198B activates. As the voltage gradient approaches approximately −12 V, SCR 194B activates, and circuits T1 and T2 may provide a lower impedance electrical path for the shunt-current compared to the electrical paths through electrodes 124, 126. In this example, clamping structure 123 does not deactivate until the absolute value of the voltage gradient is less than 1.4 V, e.g., −1.3 V.

Similar to FIGS. 8A and 8B, if symmetrical activation capability is not necessary, only one of circuits T1 or T2 may be needed. In such examples, if clamping structure 123 comprises circuit T1 and not T2, clamping structure 123 may activate when the voltage gradient exceeds 10 V, and SCR 194A may activate when the voltage gradient exceeds 12 V. Similarly, if clamping structure 123 comprises circuit T2 and not T1, clamping structure 123 may activate when the voltage gradient is negative and the absolute value of the negative voltage gradient exceeds 10 V, and SCR 194A may activate when the absolute value of the negative voltage gradient exceeds 12 V.

Similar to the description with respect to FIGS. 8A-8D, in some examples, the activation of clamping structure 123 may not provide a lower impedance electrical path for the shunt-current compared to the electrical path through electrodes 124, 126. However, even in such examples, the amount of the shunt-current that flows through electrodes 124, 126 may be reduced. The activation of clamping structure 123, as shown in FIG. 8E, provides additional paths for the shunt-current in addition to the paths through electrodes 124, 126. Accordingly, some of the shunt-current is diverted from electrodes 124, 126 and flows through clamping structure 123 even in examples where the electrical path through clamping structure 123 is not necessarily of a lower impedance compared to the electrical path through electrodes 124, 126.

Figure 9:
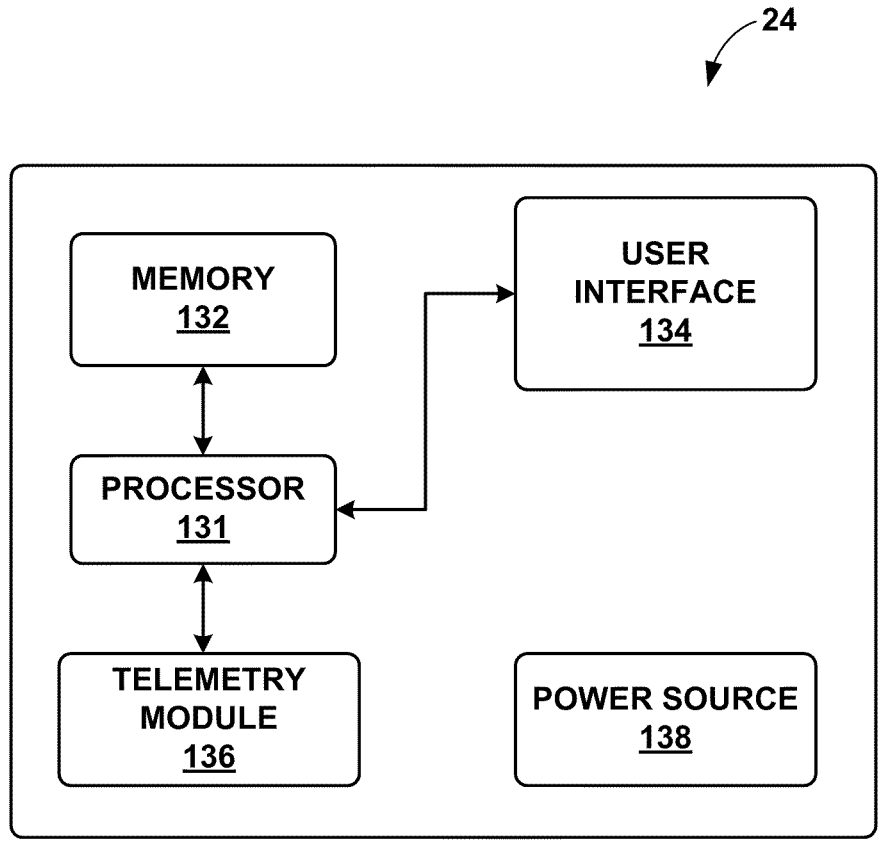
FIG. 9 is a functional block diagram of an example medical device programmer.

FIG. 9 is block diagram of an example programmer 24. As shown in FIG. 9, programmer 24 includes processor 131, memory 132, user interface 134, telemetry module 136, and power source 138. Programmer 24 may be a dedicated hardware device with dedicated software for programming of ICD 16 and INS 26. Alternatively, programmer 24 may be an off-the-shelf computing device running an application that enables programmer 24 to program ICD 16 and INS 26. In some examples, separate programmers may be used to program ICD 16 and INS 26. However, a common programmer 24 that is configured to program both ICD 16 and INS 26 may provide a more streamlined programming process for a user, such as a clinician or patient 12.

A user may use programmer 24 to select therapy programs (e.g., sets of stimulation parameters), generate new therapy programs, modify therapy programs through individual or global adjustments or transmit the new programs to a medical device, such as ICD 16 or INS 26 (FIG. 1). The clinician may interact with programmer 24 via user interface 134, which may include display to present graphical user interface to a user, and a keypad or another mechanism for receiving input from a user.

Processor 131 can take the form one or more microprocessors, DSPs, ASICs, FPGAs, programmable logic circuitry, or the like, and the functions attributed to processor 131 herein may be embodied as hardware, firmware, software or any combination thereof. Memory 132 may store instructions that cause processor 131 to provide the functionality ascribed to programmer 24 herein, and information used by processor 131 to provide the functionality ascribed to programmer 24 herein.

Memory 132 may include any fixed or removable magnetic, optical, or electrical media, such as RAM, ROM, CD-ROM, hard or floppy magnetic disks, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery by ICD 16 and INS 26, such as stimulation parameter values.

Programmer 24 may communicate wirelessly with ICD 16 and INS 24, such as using RF communication or proximal inductive interaction. This wireless communication is possible through the use of telemetry module 136, which may be coupled to an internal antenna or an external antenna. An external antenna that is coupled to programmer 24 may correspond to the programming head that may be placed over heart 14, as described above with reference to FIG. 1. Telemetry module 136 may be similar to telemetry module 98 of ICD 16 (FIG. 6) or telemetry module 118 of INS 26 (FIGS. 7A, 7B and 7C).

Telemetry module 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation. Recharging may be accomplished by electrically coupling power source 138 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 138 may include circuitry to monitor power remaining within a battery. In this manner, user interface 134 may provide a current battery level indicator or low battery level indicator when the battery needs to be replaced or recharged. In some cases, power source 138 may be capable of estimating the remaining time of operation using the current battery.

In some cases, the placement of ICD 16 and INS 26 relative to each other within patient 12 may help reduce the amount of shunt-current that flows through electrodes 124 (FIGS. 7A and 7B) and into INS 26. For example, the shunt-current to INS 26 from ICD 16 may be reduced by placing INS 26 and lead 28 substantially outside of the current path generated by the delivery of stimulation by ICD 16.

Figure 10:
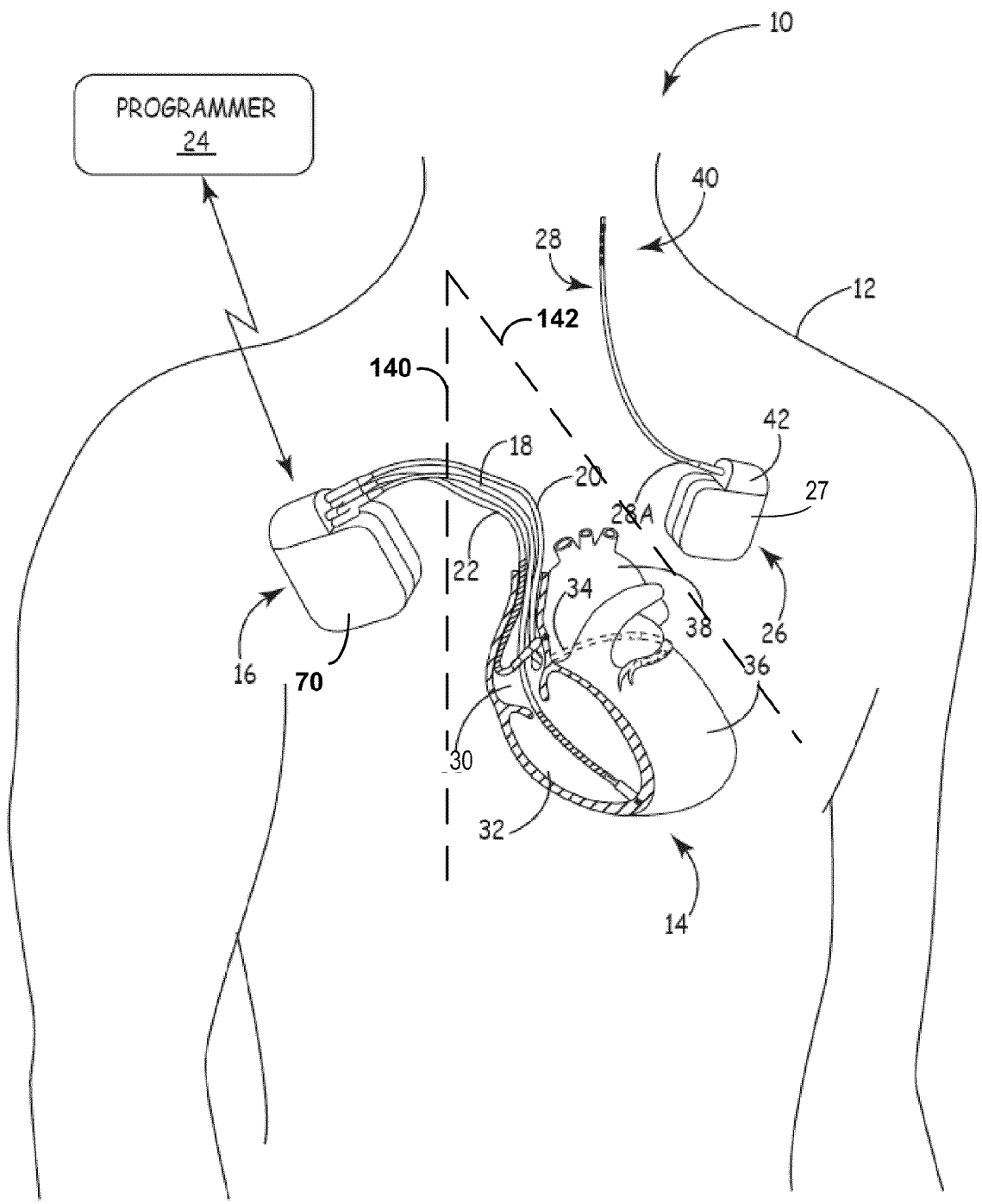
FIG. 10 is a conceptual diagram illustrating an example placement of the ICD and INS within a patient.

FIG. 10 is a conceptual diagram that helps illustrate this concept. FIG. 10 is substantially similar to FIG. 1 but illustrates marker lines 140 and 142. As FIG. 10 illustrates, shunt-current to INS 26 may be mitigated by placing INS 26 such that electrodes 124 of lead 28 (FIGS. 7A, 7B, and 7C) are not positioned between housing 70 of ICD 16 and electrodes 50, 52, 54, 56, 58, 60, 68, 72, 74, and 76 of leads 18, 20, and 22 (FIGS. 3 and 4), or, specifically between housing 70 and electrodes 68, 72, 74, 76 (FIGS. 3 and 4) that may be used to deliver a cardioversion or defibrillation shock to heart 14.

In the example shown in FIG. 10, the current path of the stimulation signal delivered by ICD 16 is between marker line 140 and marker line 142 (e.g., the space including heart 14), and INS 26 is outside the current path of the stimulation signal, e.g., outside of the area marked by marker lines 140 and 142. Marker lines 140 and 142 are a two dimensional representation of marker lines for purposes of illustrations. In some examples, housing 27 of INS 26 maybe positioned between lines 140, 142, while electrodes 124 of lead 28 (FIGS. 7A, 7B, and 7C) may remain outside of the current path, e.g., outside of the spaced defined between lines 140, 142. During implantation of INS 26 and lead 28 within patient 12, the clinician may determine the approximate current path of the stimulation delivered by ICD 16 based on the stimulation parameter values, such as the amplitude, frequency, and pulse width of the stimulation parameters, as well as the known characteristics of tissue proximate leads 18, 20, 22 and housing 70.

INS 26 may be located on either marker 142 or within about 2.5 to 10.2 centimeters on either side of marker 142. ICD 16 may be within the area marked by marker 140 and 142. By placing INS 26 outside of the stimulation current path of ICD 16 the shunt-current may be reduced or eliminated because no stimulation current may feed into INS 26.

Clamping structure 123 and nontherapeutic electrode 125 (FIG. 7A) may reduce shunt-current received by therapy delivery components (e.g., stimulation generator 114 or a sensing module) of INS 26 due to the delivery of stimulation by ICD 16. FIGS. 11-15 are conceptual diagrams illustrating various examples of shunt-current mitigation circuitry 119 (FIG. 7B) that may be used to further reduce shunt-current received by INS 26 due to the delivery of stimulation by ICD 16. FIGS. 11-15 illustrate stimulation generator 114 disposed within housing 27 of INS 26. For purposes of illustration, the additional components of INS 26, such as switching module 116 and processor 110, are not illustrated in FIGS. 11-15. Although FIGS. 11-15 illustrate an example in which shunt-current mitigation circuitry 119 is external to housing 27, in other examples, shunt-current mitigation circuitry 119 may be enclosed within housing 27, connector block 42 (FIG. 1) or otherwise electrically coupled to electrodes 124.

Figure 11:
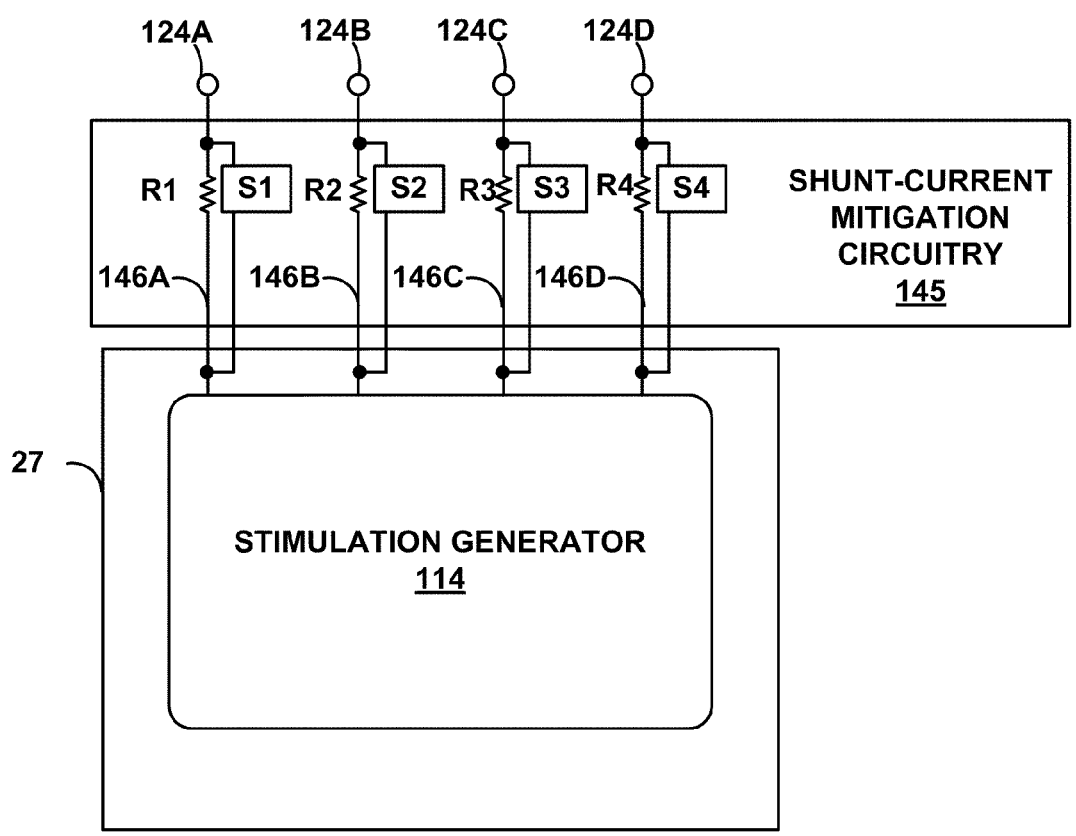
FIG. 11 is a block diagram illustrating an example implantable medical device (IMD) that includes shunt-current mitigation components.

FIG. 11 is a conceptual block diagram that illustrates an example of shunt-current mitigation circuitry 145, which is an example of shunt-current mitigation circuitry 119 (FIG. 7B). In the example shown in FIG. 11, electrodes 124A-124D of lead 28 (FIG. 7B) are electrically coupled to stimulation generator 114 with a respective conductor 146A-146D (collectively "conductors 146"), respectively. Conductors 146 may be enclosed in a common lead body (e.g., lead 28) or separate lead bodies. In the example shown in FIG. 11, shunt-current mitigation circuitry 145 comprises resistors R1-R4, which are electrically coupled to a respective one of the conductors 146. As shown in FIG. 11, resistors R1-R4 are external to housing 27. In some examples, resistors R1-R4 may be internal to housing 27.

Resistors R1-R4 may comprise high impedance (or "resistance") resistors. Resistors R1-R4 may each have a resistance of about 1 kiloohm to about 10 kiloohms, although other resistance values are contemplated. In some examples, wires 146A-146D may comprise low impedance wires. In some other examples, wires 146A-146D may comprise high impedance wires. Example values of the impedance of wire 146A-146D may be about 10 ohms to 10 kiloohms, 10 ohms to 100 ohms, or 3.5 kiloohms to 10 kiloohms, although other impedance values are contemplated.

In some examples, in addition to being resistive, wires 146A-146D may be inductive. Example values of the inductance of wires 146A-146D may be about 0.1 mH to 100 mH. In examples in which wires 146A-146D are inductive, wires 146A-146D may inhibit instantaneous changes in currents flowing through wires 146A-146D. Furthermore, in some examples, shunt-current mitigation circuitry 145 may not include resistors R1-R4, but the shunt-current mitigation may be provided by high-impedance wires 146A-146D. In such examples, the high impedance wires 146A-146D may be considered shunt-current mitigation circuitry 145.

As shown in FIG. 11, in some examples, shunt-mitigation circuitry 119 may comprise switches S1-S4 as shown in FIG. 11. Switches S1-S4 may comprise any one or more of electronic switches, FET switches, reed switches, optical isolators, SCRs, or other forms of switches. When closed, each one of switches S1-S4 may provide a low impedance electrical path for a stimulation signal generated by stimulation generator 114. Switches S1-S4 generally remain open except for when electrodes 124 need to be electrically connected to components within INS 26. For example, switches S1-S4 may remain open except for when stimulation generator 114 is delivering a stimulation signal via electrodes 124, when a sensing module within INS 26 is sensing one or more physiological parameters of patient 12 via electrodes 124, or when processor 110 (FIGS. 7A, 7B, and 7C) of INS 26 determines an impedance of an electrical path including electrodes 124, e.g., for lead integrity determinations. When stimulation generator 114 is about to transmit a neurostimulation signal, INS 26 may toggle switches S1-S4 closed, thereby creating a low impedance electrical path for the neurostimulation signal. When switches S1-S4 are open, no shunt-current may flow through switches S1-S4, and all the shunt-current may only flow through resistors R1-R4.

In examples where shunt-current mitigation circuitry does not include resistors R1-R4 and wires 146A-146D are resistive wires, switches S1-S4 may function in the same manner as examples that include resistors R1-R4. For example, switches S1-S4 may remain open except for when stimulation generator 114 is outputting a stimulation signal or when a sensing module is sensing one or more physiological parameters of patient 12. Furthermore, in some examples, switches S1-S4 may not be necessary, and resistors R1-R4 and wires 146A-146D may provide shunt-current mitigation.

Resistors R1-R4 and/or wires 146A-146D increase an impedance of the shunt-current path through electrodes 124. Accordingly, the presence of resistors R1-R4 may reduce the amount shunt-current that flows through INS 26 from the delivery of electrical stimulation by ICD 16. In this way, increasing the impedance of the electrical path between electrodes 124 and stimulation generator 114 may help reduce the amount of shunt-current that is introduced into stimulation generator 114, as well as reduce the possibility that tissue between INS 26 and ICD 16 may be unintentionally stimulated or stressed due to the flow of shunt-current through electrodes 124.

The flow of shunt-current into stimulation generator 114 may be undesirable because stimulation generator 114 may be intended to only source electrical current as stimulation signals and not sink electrical current. The shunt-current may cause stimulation generator 114 to sink current, which may stress stimulation generator 114 if stimulation generator 114 is only configured to source current. Moreover, the shunt-current and the stimulation current generated by stimulation generator 114 may flow in opposite directions. For example, the shunt-current may flow into electrodes 124 and into stimulation generator 114 while the stimulation current may flow out of electrodes 124. Thus, the flow of shunt-current into electrodes 124 may reduce the amount of stimulation that is actually provided by the stimulation generator 114, which may affect the efficacy of the therapy provided by INS 26.

Figure 12:
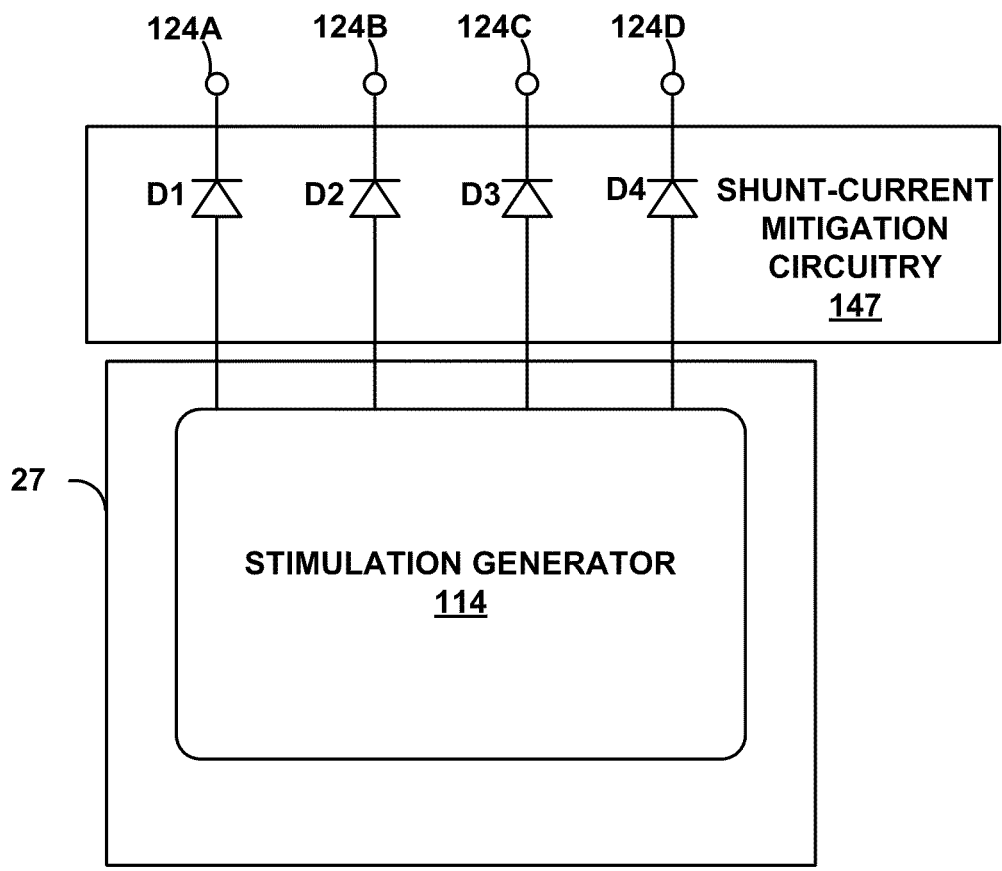
FIG. 12 is a block diagram illustrating another example IMD that includes shunt-current mitigation components.

FIG. 12 is a block diagram illustrating another example shunt-current mitigation circuitry 147. In the example shown in FIG. 12, shunt-current mitigation circuitry 147 comprises diodes D1-D4, which are electrically coupled to stimulation generator 114 and electrodes 124. Electrodes 124A-124D are electrically coupled to stimulation generator 114 via diodes D1-D4. As shown in FIG. 12, diodes D1-D4 are located externally to housing 27. In other examples, diodes D1-D4 may be internal, e.g., enclosed within housing 27. In some examples, diodes D1-D4 may comprise diodes that are configured to conduct in two directions. For example, diodes D1-D4 may comprise transient absorber diodes or Zener diodes. Diodes D1-D4 may allow the current generated by stimulation generator 114 to flow from stimulation generator 114 to electrodes 124 via conductors within lead 28. However, diodes D1-D4 may limit the amount of current that may flow from electrodes 124 to stimulation generator 114.

In some examples, diodes D1-D4 may be leaky diodes that allow charge that is built up on electrodes 124 to dissipate into housing 27. Because diodes D1-D4 only allow current to flow in one direction, electrodes 124 may build up charge which may cause electrodes 124 to corrode. The leaky characteristic of diodes D1-D4 may allow the built up charge to dissipate into housing 27 and minimize the corrosion of electrodes 124.

Diodes D1-D4 may generate a high impedance path for a shunt-current to flow from electrodes 124 into stimulation generator 114. Accordingly, the presence of diodes D1-D4 may reduce the amount of shunt-current that flows from ICD 16 to INS 26. In this way, placing diodes D1-D4 in the electrical path between electrodes 124 and stimulation generator 114 may help reduce the amount of shunt-current that is introduced into stimulation generator 114, as well as reduce the possibility that tissue adjacent electrodes 124 may be unintentionally stimulated or stressed due to the flow of shunt-current through electrodes 124.

FIG. 13 is a conceptual block diagram illustrating another example shunt-current mitigation circuit 148, which includes switches S5-S8 that are electrically coupled to a respective electrode 124A-124D. Switches S5-S8 may comprise any one or more of electronic switches, FET switches, reed switches, optical isolators, SCRs, and the like. Switches S5-S8 may be controlled by processor 110 (FIGS. 7A, 7B, and 7C) of INS 26. In some examples, ICD 16 may transmit a communication signal to INS 26 via the respective telemetry modules 98 (FIG. 6), 118 (FIGS. 7A, 7B, and 7C), where the communication signal indicates prospective therapy delivery by ICD 16. In some other examples, ICD 16 may transmit a communication signal to programmer 24 (FIG. 1) via telemetry module 98 (FIG. 6), where the communication signal is indicative of prospective therapy delivery by ICD 16. For example, ICD 16 may transmit a communication signal to INS 26 that indicates that ICD 16 is intending on delivering a stimulation signal (e.g., a defibrillation shock) to patient 12, e.g., within about five seconds or less. Programmer 24 may transmit the communication signal to INS 26, which may receive the communication signal via telemetry module 118. The communication signal may or may not provide therapeutic benefits to patient 12. In response to receiving the communication signal from ICD 16, processor 110 of INS 26 may toggle switches S5-S8 open in order to limit or even stop the current flow through switches S5-S8. In this way, the opening of switches S5-S8 may reduce the flow of shunt-current from the stimulation generated by ICD 16 into stimulation generator 114.

Figure 14:
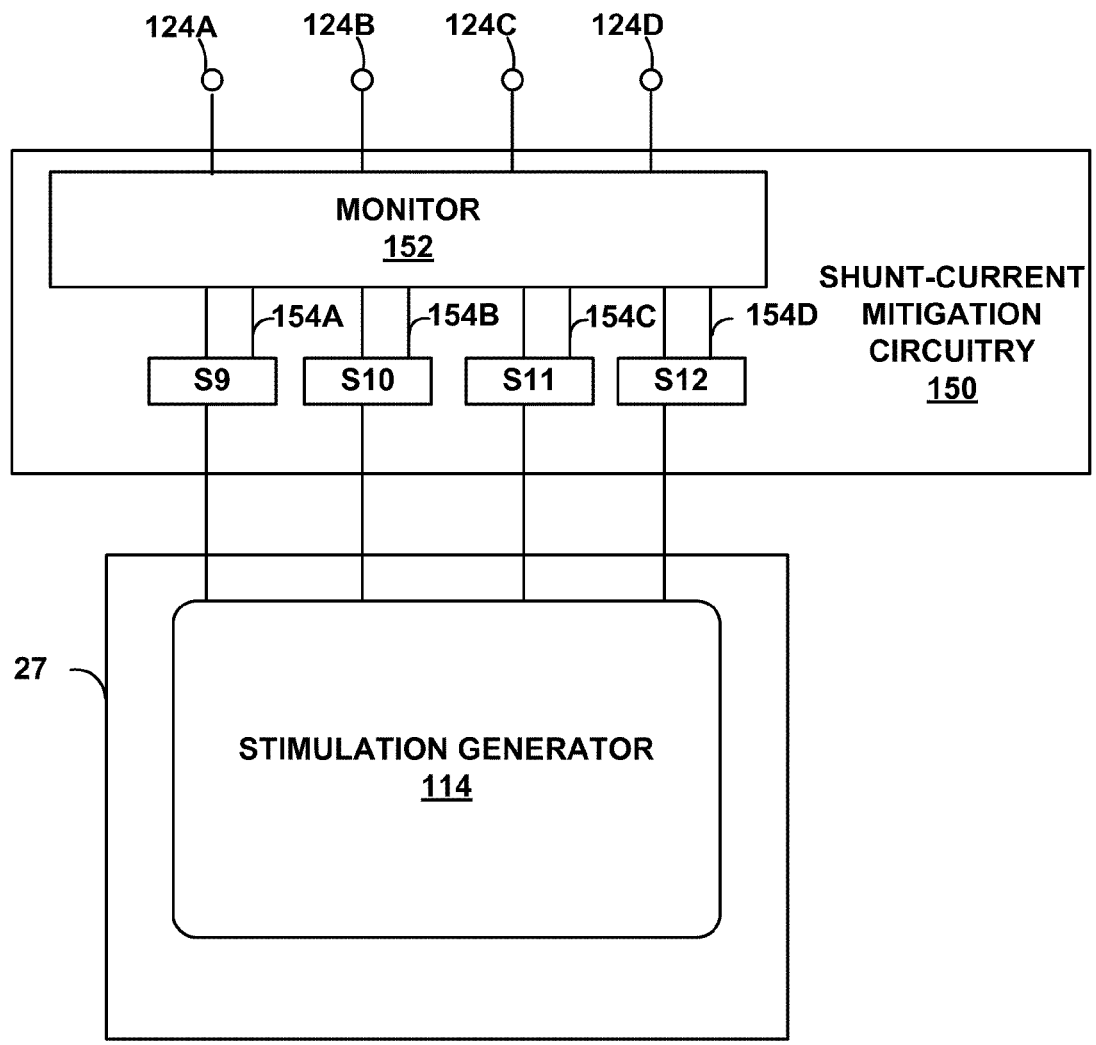
FIG. 14 is a block diagram illustrating another example IMD that includes shunt-current mitigation components.

FIG. 14 is a block diagram illustrating another example of shunt-current mitigation circuitry 150, which includes monitor 152 and switches S9-S12. Monitor 152 monitors an electrical parameter value at one or more of the electrodes 124. The electrical parameter value may be a voltage at each one of electrodes 124, a current through each one of electrodes 124, or a voltage across at least two of electrodes 124. In the example shown in FIG. 14, electrodes 124 are electrically coupled to stimulation generator 114 via monitor 152 and switches S9-S12, respectively. Monitor 152 may include a voltage monitor or a current monitor. In some examples, monitor 152 comprises a plurality of current monitors or voltage monitors that monitor the current flowing through a respective one of electrodes 124, or monitor the voltage at each one of electrodes 124. A current monitor may monitor the current in series with the current flow through electrodes 124, and a voltage monitor may monitor voltage in parallel with the current flow through electrodes 124. Accordingly, in examples in which monitor 152 comprises one or more voltage monitors, each one of the voltage monitors may comprise a low impedance resistor. Each one of the voltage monitors may measure the voltage across the low impedance resistor.

In other examples in which monitor 152 comprises one or more voltage monitors, the voltage monitor may not measure the voltage at electrodes 124. Instead, the voltage monitor may measure the voltage across two of electrodes 124. For example, one voltage monitor may measure the voltage across electrode 124A and 124B, and a second voltage monitor may measure the voltage across electrode 124C and 124D. Measuring the voltage across two electrodes may be beneficial where electrodes 124 are bipolar electrodes.

In examples in which monitor 152 comprises a current monitor, if the current that flows through one or more of the electrodes 124 is greater than or equal to a predetermined threshold value, monitor 152 may transmit a signal via a respective control line 154A-154D to toggle switches S9-S12 open. Switches S9-S12 may be substantially similar to switches S1-S4 (FIG. 11). A clinician may select the threshold current value that triggers the opening of switches S9-S12. In some examples, the threshold current value may be within the range of about 1 milliamp to about 100 milliamps, such as about 10 milliamps to about 50 milliamps, although other threshold current values are contemplated. As previously discussed, the threshold current value may be selected based on various factors, such as the amount of current and/or energy that the circuitry within INS 26 is designed to withstand without substantial damage, the type if tissue in which electrodes 124 are implanted, or the surface area of electrodes 124.

In examples in which monitor 152 comprises a voltage monitor, if the voltage across the low impedance resistor within the voltage monitor is greater than or equal to a predetermined threshold voltage value, or if the voltage across two of electrodes 124 is greater than the threshold voltage value, monitor 152 may transmit a signal via control line 154A-154D to toggle open switches S9-S12. Again, a clinician may select the threshold voltage value, which may be, for example, in a range of about 15 volts to about 1000 volts, such as about 15 volts to about 50 volts. However, other threshold voltage values are contemplated.

Figure 15:
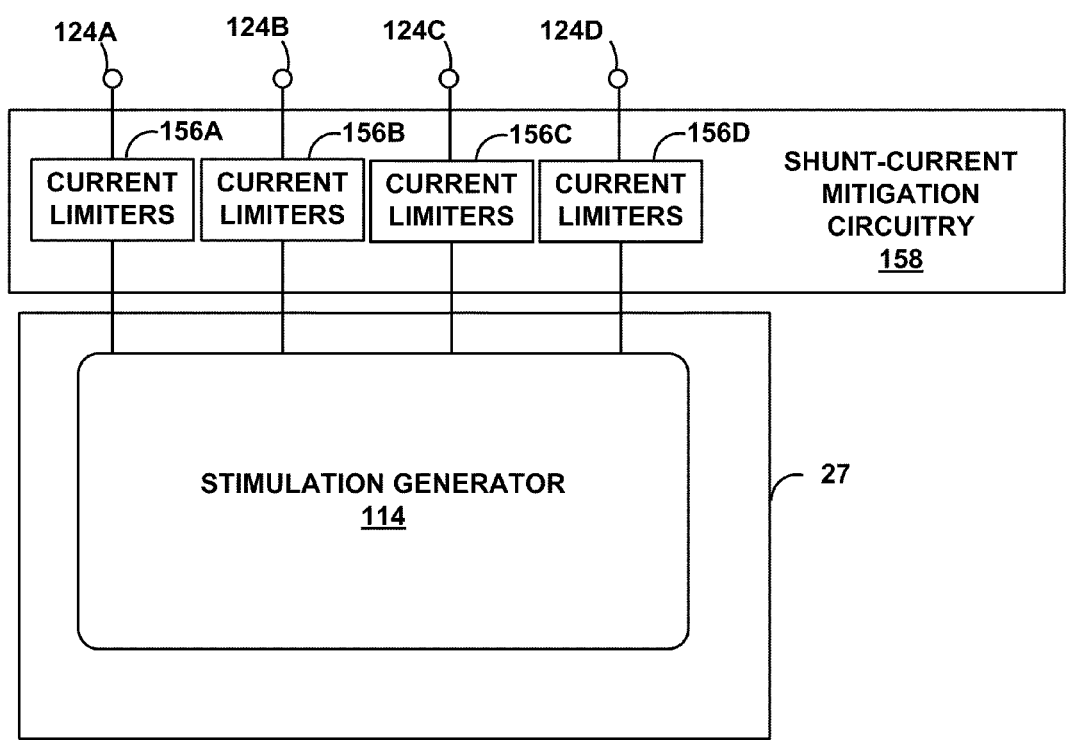
FIG. 15 is a block diagram illustrating another example IMD that includes shunt-current mitigation components.

FIG. 15 is a block diagram illustrating another example of shunt-current mitigation circuitry 158. In the example shown in FIG. 15, shunt-current mitigation circuitry 158 comprises current limiters 156A-156D (collectively referred to as "current limiters 156"), which are electrically coupled to stimulation generator 114 and electrodes 124. Each one of current limiters 156 may comprise a fuse or a bimetallic circuit breaker, in one aspect. One example of a fuse is a resettable fuse.

Current limiters 156 may limit the amount of current that may flow from electrodes 124 to stimulation generator 114. If the current that may flow from electrodes 124 is greater than a threshold current for current limiters 156, current limiters 156 may provide a high impedance for the current, thereby limiting the amount of current that may flow from electrodes 124 to stimulation generator 114. For example, at least one of the current limiters 156 may comprise a resettable fuse. The resettable fuse may activate and may provide high impedance when the shunt-current is greater than the threshold current. The resettable fuse provides high impedance path by blocking substantially all current, e.g., creating an open circuit. In such a manner, the resettable fuse activates to keep the shunt-current within or nearer to a safe level, thereby reducing or avoiding stress to the tissue. After activation, in some examples, the resettable fuse deactivates by itself or by a control signal provided by processor 110 (FIGS. 7A, 7B, and 7C). Accordingly, the presence of current limiters 156 may limit the amount of shunt-current that flows from ICD 16 to INS 26. In this way, placing current limiters 156 in the electrical path between electrodes 124 and stimulation generator 114 may help limit the amount of shunt-current that is introduced into stimulation generator 114, as well as reduce the possibility that tissue adjacent electrodes 124 may be unintentionally stimulated or stressed due to the flow of shunt-current through electrodes 124.

Various shunt-current mitigation circuitries (or components) are described in FIGS. 11-15. In some examples, stimulation generator 114 may be coupled to one or more of the shunt-current mitigation circuitries described with respect to FIGS. 11-15. For example, stimulation generator 114 may be coupled to each one of electrodes 124 via a resistive wire, a resistor, a switch, and a monitor. As another example, stimulation generator 114 may be coupled to each one of electrodes 124 via only a resistive wire and a switch. As yet another example, stimulation generator 114 may be coupled to each one of electrodes 124 via a resistor and a current limiter. Other permutations and combinations may be possible, and are contemplated by this disclosure.

Figure 16:
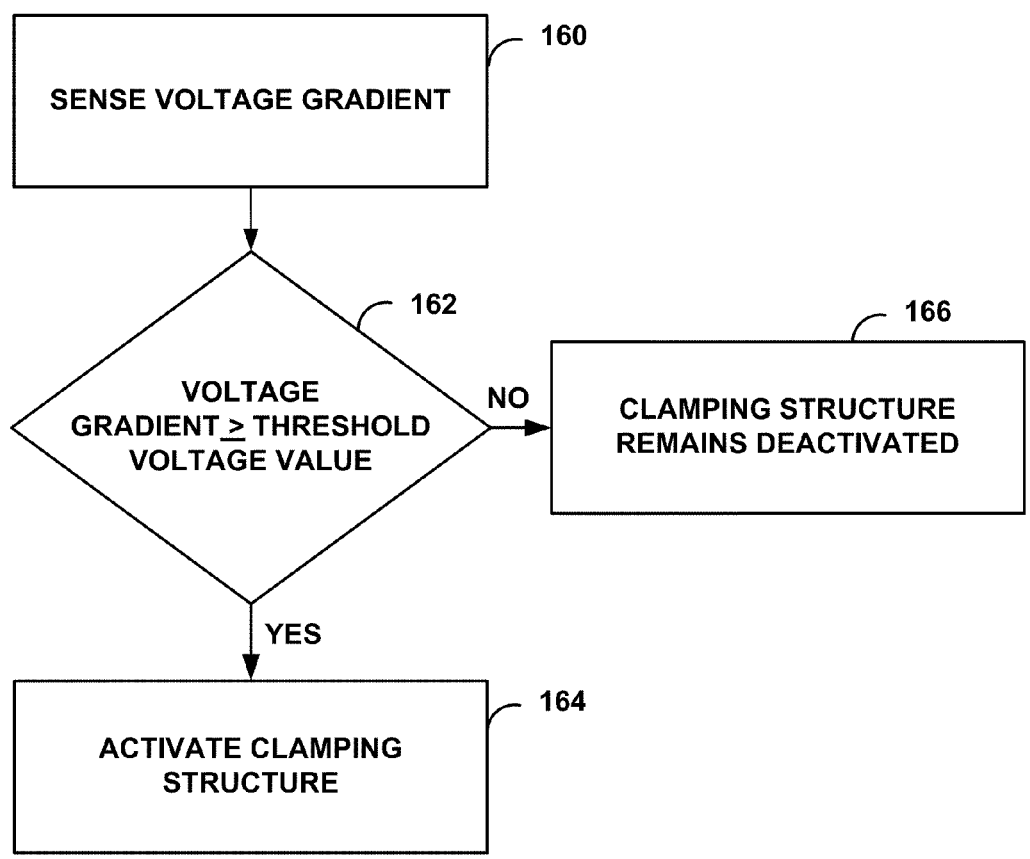
FIG. 16 is a flow diagram illustrating an example technique that may be implemented to reduce shunt-current that may flow through an electrical path connected to an IMD.

FIG. 16 is a flow diagram illustrating an example technique that INS 26 may implement in order to limit or reduce shunt-current. For purposes of illustration, reference will be made to FIG. 7A. In accordance with the technique shown in FIG. 16, electrode 125 may sense a voltage gradient generated by a stimulation signal from ICD 16 (160). If the voltage gradient is greater than or equal to a threshold voltage value (YES of 162), clamping structure 123 may activate and provide a lower impedance electrical path for the shunt-current generated by the stimulation signal compared to an electrical path through electrodes 124, 126 (164). In an activated state, clamping structure 123 may divert a substantial amount of the shunt-current generated by ICD 16 that may flow into circuitry within INS 26, e.g., stimulation generator 114, through electrodes 124. The substantial amount of the shunt-current may flow into housing 27 via electrode 125 thereby diverting the substantial amount of the shunt-current from flowing into circuitry within INS 26. In the activated state, clamping structure 123 and electrode 125 provide a path for the shunt-current of approximately the same impedance or lower impedance than through electrodes 124. In this way, clamping structure 123 and electrode 125 may help divert the amount of shunt-current that is introduced into stimulation generator 114, as well as reduce the possibility that tissue adjacent electrodes 124 may be unintentionally stimulated or stressed due to the flow of shunt-current through electrodes 124. If the voltage gradient is less than the threshold voltage value (NO of 158), clamping structure 123 may remain deactivated (166). In a deactivated state, clamping structure 123 provides high impedance for currents compared to the impedance when clamping structure 123 is active. In the deactivated state, clamping structure may limit the amount of current that may flow from electrode 125 into housing 27.

Figure 17:
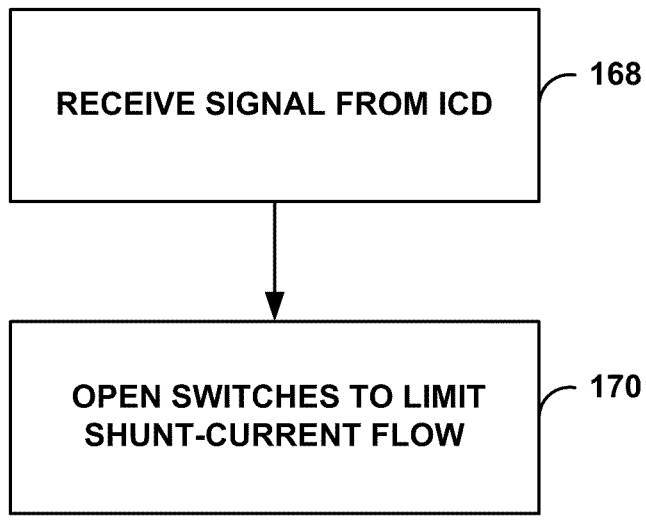
FIG. 17 is a flow diagram illustrating another example technique that may be implemented to reduce shunt-current that may flow through an electrical path connected to an IMD.

FIG. 17 is a flow diagram illustrating another example technique that INS 26 may implement in order to limit shunt-current. For purposes of illustration, reference will be made to shunt-current mitigation circuitry 148 described with respect to FIG. 13. In accordance with the technique shown in FIG. 17, INS 26 may receive a communication signal from ICD 16 indicating prospective therapy delivery by ICD 16 (168). The communication signal may be provided by telemetry module 98 (FIG. 6) and received by telemetry module 118 (FIGS. 7A, 7B, and 7C). For example, ICD 16 may transmit a communication signal to programmer 24 (FIG. 1) via telemetry module 98 (FIG. 6), where the communication signal is indicative of prospective therapy delivery by ICD 16. For example, ICD 16 may transmit a communication signal to INS 26 that indicates that ICD 16 is intending on delivering a stimulation signal (e.g., a defibrillation shock) to patient 12, e.g., within about five seconds or less. In response to receiving the communication signal from ICD 16, processor 110 may control one or more switches S5-S8 to toggle open in order to limit the current that may feed into INS 26 via switches S5-S8 (170). In this way, the opening of switches S5-S8 may reduce the flow of shunt-current from the stimulation generated by ICD 16 into stimulation generator 114.

Figure 18:
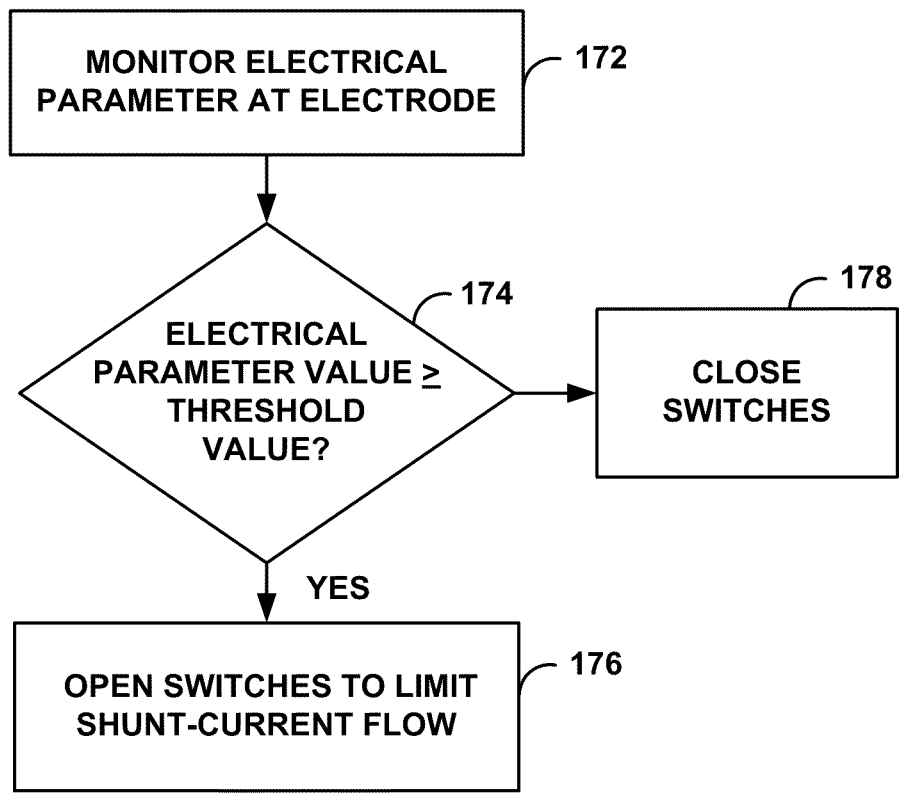
FIG. 18 is a flow diagram illustrating another example technique that may be implemented to reduce shunt-current that may flow through an electrical path connected to an IMD.

FIG. 18 is a flow diagram illustrating another example technique that INS 26 may implement in order to limit shunt-current. For purposes of illustration, reference will be made to shunt-current mitigation circuitry 150 illustrated in FIG. 14. In accordance with the technique shown in FIG. 18, monitor 152 monitors an electrical parameter value at one or more of therapeutic electrodes 124 that are electrically connected to stimulation generator 114 of INS 26 (FIG. 7A) (172). The electrical parameter value may be a voltage at each one of electrodes 124, a current through each one of electrodes 124, or a voltage across at least two of electrodes 124.

Processor 110, or a processor within monitor 152 may determine whether the measured parameter value (e.g., current or voltage) is greater than or equal to a threshold value (174). The threshold value may, in some instances, be stored within memory 112, or may be stored within monitor 152. If the measured parameter value is greater than or equal to the threshold value (YES of 174), monitor 152 may control switches S9-S12 (FIG. 14) to toggle open to limit the current that feeds into INS 26 (176). If the measured parameter value is less than or equal to the threshold value (NO of 174), monitor 152 may control switches S9-S12 to toggle close (178).

Figure 19:
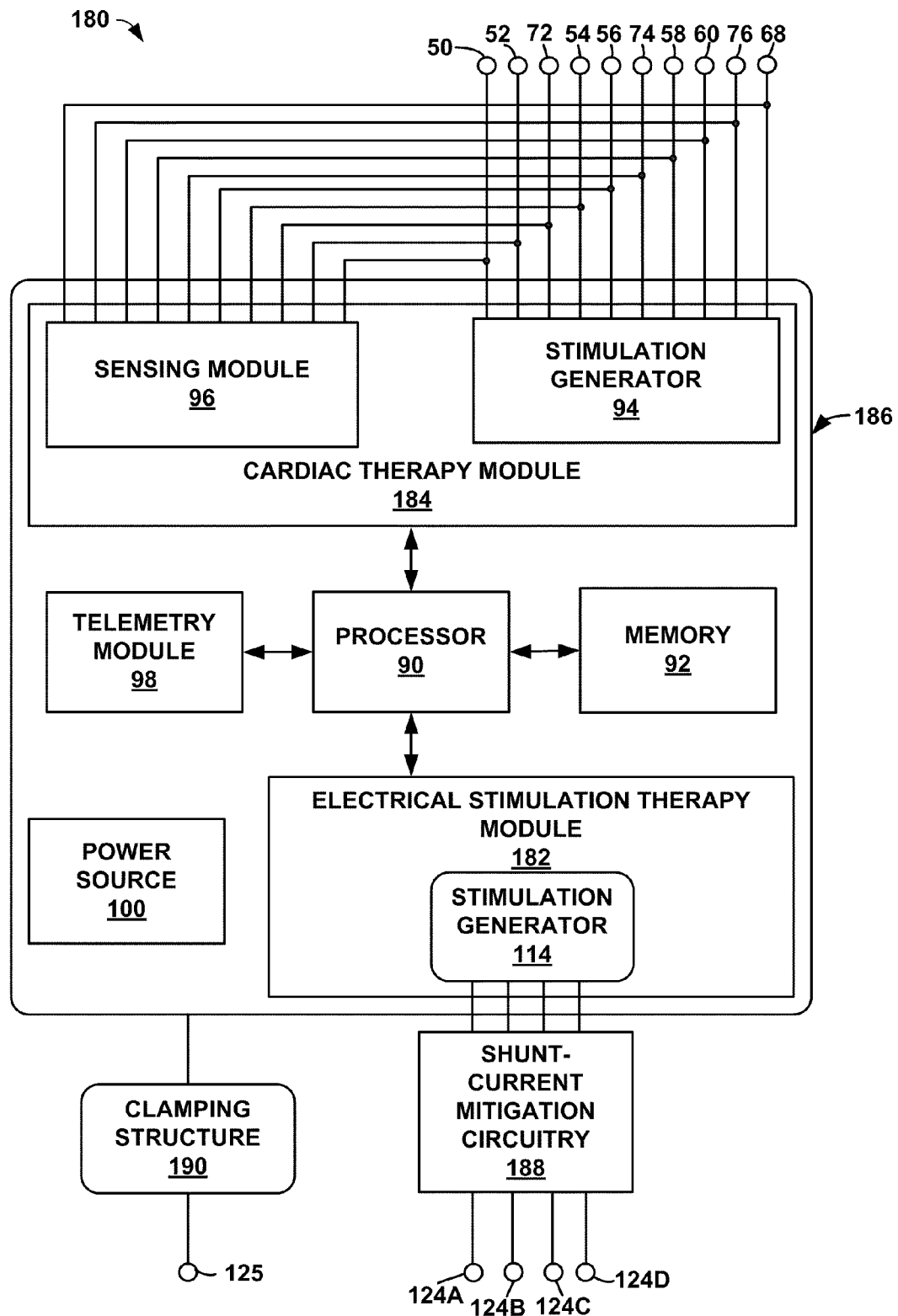
FIG. 19 is a functional block diagram of an example IMD that includes an electrical stimulation module that generates and delivers electrical stimulation to a tissue site within a patient, e.g. proximate a nerve and/or an extravascular tissue site, and a cardiac therapy module that generates and delivers cardiac rhythm therapy to a heart of the patient.

FIG. 19 is a functional block diagram illustrating an example IMD 180 that includes electrical stimulation therapy module 182 and cardiac therapy module 184 in a common housing 186. Electrical stimulation therapy module 182 may be, for example, include circuitry for generating electrical stimulation that is delivered to a nonmyocardial tissue site within patient 12 or a nonvascular cardiac tissue site within patient 12. For example, electrical stimulation therapy module 182 may be a neurostimulation module that generates and delivers neurostimulation therapy to patient 12. Electrical stimulation therapy module 182 includes stimulation generator 114, which is described above with respect to FIGS. 7A and 7B. Similarly, cardiac therapy module 184 includes stimulation generator 94 and sensing module 96, which are described above with respect to ICD 16 (FIG. 6). IMD 180 also includes processor 90, memory 92, telemetry module 98, and power source 100, which are described above with respect to FIG. 6.

Electrical stimulation therapy module 182 may deliver electrical stimulation to a tissue site proximate to a nerve. As previously discussed with respect to INS 26, the stimulation may be delivered to the nerve via an intravascular lead or an extravascular lead. In other examples, electrical stimulation therapy module 182 may deliver electrical stimulation to an extravascular tissue site that may or may not be proximate a nerve. Cardiac therapy module 184 may sense electrical cardiac signals of patient 12 and deliver cardiac rhythm management therapy to heart 14, such as pacing, cardioversion or defibrillation therapy.

Processor 90, as shown in FIG. 19, may perform all the functions ascribed to processor 90 of FIG. 6 and processor 110 of FIGS. 7A and 7B. Similarly, memory 92 and telemetry module 98, as shown in FIG. 19, may perform all the functions ascribed to memory 92 and telemetry module 98 of FIG. 6 and memory 112 and telemetry module 118 of FIGS. 7A and 7B, respectively. Power source 100 may provide power to both electrical stimulation therapy module 182 and cardiac therapy module 184, as well as processor 90, memory 92, and telemetry module 98.

In some examples, electrical stimulation therapy module 182 is electrically connected to electrodes 124 via shunt-current mitigation circuitry 188. Shunt-current mitigation circuitry 188 may be similar to shunt-current mitigation circuitry 119 (FIG. 7B) of INS 26, examples of which are described above with respect to FIGS. 11-15. For example, shunt-current mitigation circuitry 188 may comprise voltage or current monitors coupled to one or more switches and electrodes 124, one or more resistors and/or current limiters coupled to the switches, and resistive wires that couple the one or more resistors to stimulation generator 114.

Furthermore, though not shown in FIG. 19, in some examples, each one of electrodes 124 may be coupled to all others electrodes 124 via clamping structures as described in FIG. 7B. Additionally, though not shown in FIG. 19, in some examples, stimulation generator 114 may be coupled to electrodes 126 of lead 29 (FIGS. 7A and 7B) via shunt mitigation circuitry substantially similar to shunt mitigation circuitry 119. Similar to FIG. 7B, in examples where stimulation generator 114 is coupled to electrodes 124 and 126, a clamping structure array similar to clamping structure array 122 may couple each one of electrodes 124 and 126 to housing 186. As another example, a clamping structure array similar to clamping structure array 122 may couple each one of electrodes 124 to each one of electrodes 126 as described with respect to FIG. 7B.

As shown in FIG. 19, in some examples, nontherapeutic electrode 125 having a larger conductive surface area than electrodes 124 is electrically connected to housing 186 of IMD 174 via clamping structure 190. Clamping structure 190 may be substantially similar to clamping structure 123 (FIGS. 7A and 7B).

Delivery of pacing, cardioversion or defibrillation therapy by cardiac therapy module 184 may generate a voltage gradient in the patient's body. As described above, this voltage gradient may generate a flow of shunt-current through an electrical path including electrodes 124. Electrode 125 and clamping structure 190 may divert a substantial amount of the shunt-current from flowing into electrodes 124. Electrode 125 and clamping structure 190 may provide a lower impedance electrical path for the shunt-current than the electrical path through electrodes 124. Due to the lower impedance electrical path through electrode 124 and clamping structure 184 as compared to the electrical path through electrodes 124, the substantial amount of shunt-current may flow into housing 186 via electrode 125 and clamping structure 190 and not through electrodes 124. Shunt-current mitigation circuitry 188 may reduce the shunt-current that flows through electrodes 124 and into stimulation generator 114 by increasing the impedance of the electrical path including electrodes 124 and stimulation generator 114.

The techniques described in this disclosure, including those attributed to ICD 16, INS 26, IMD 174, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 90 of ICD 16 or IMD 164, processor 110 of INS 26, and/or processor 131 of programmer 24, any one or more parts of the techniques described herein may be implemented by a processor of one of the devices 16, 26, 164, programmer 24 or another computing device, alone or in combination with ICD 16, INS 26, IMD 164, or programmer 24.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described in the disclosure. These and other examples are within the scope of the following claims.

The invention claimed is:

1. A system comprising:
a first therapy module comprising a housing and a signal generator enclosed within the housing, wherein the signal generator is configured to generate and deliver electrical stimulation to a first tissue site within a patient via a first electrode electrically connected to the signal generator;
a second therapy module configured to deliver electrical stimulation to a second tissue site within the patient;
a second, nontherapeutic electrode that is not used by the second therapy module for the delivery of the electrical stimulation by the second therapy module; and
a clamping structure configured to electrically connect the second, nontherapeutic electrode to the housing of the first therapy module, wherein the clamping structure is configured to reduce a shunt-current introduced into the first therapy module via the first electrode, and wherein the shunt-current is generated by the delivery of electrical stimulation by the second therapy module.

2. The system of claim 1, wherein the clamping structure is configured to electrically connect the second, nontherapeutic electrode to the housing of the first therapy module when a voltage gradient generated by the electrical stimulation delivered by the second therapy module to the second tissue site is greater than or equal to a threshold voltage value, wherein the voltage gradient generates the shunt-current, and wherein the clamping structure is configured to provide a lower impedance electrical path for the shunt-current than an electrical path through the first electrode.

3. The system of claim 1, wherein the clamping structure comprises one or more of a diode, a Zener diode, a gas plasma arrestor, a varistor, or a combination thereof.

4. The system of claim 1, wherein the second, nontherapeutic electrode comprises a conductive surface area that is larger than a conductive surface area of the first electrode.

5. The system of claim 1, wherein the second, nontherapeutic electrode is configured to be implanted in one of a subcutaneous layer, a sub-muscular location, and intravenous location of the patient.

6. The system of claim 1, wherein the housing substantially encloses the first and second therapy modules.

7. The system of claim 1, wherein the housing comprises a first outer housing, wherein the system further comprises:
a first implantable medical device (IMD) comprising the first outer housing, the first outer housing enclosing the first therapy module; and
a second IMD comprising a second outer housing enclosing the second therapy module, wherein the first and second outer housings are physically separate from each other and are configured to be separately implanted within the patient.

8. The system of claim 1, wherein the first therapy module comprises an electrical stimulation module configured to deliver electrical stimulation via the signal generator to the first tissue site, wherein the first tissue site comprises at least one of a nonmyocardial tissue site or a nonvascular cardiac tissue site within the patient, and the second therapy module comprises a cardiac therapy module that is configured to deliver at least one of pacing, cardioversion or defibrillation therapy to the second tissue site, and wherein the second tissue site comprises a heart of the patient.

9. The system of claim 1, wherein the second therapy module comprises at least one of an automatic external defibrillator, an implantable defibrillator, and intravenous defibrillator.

10. The system of claim 1, wherein the first therapy module comprises a cardiac therapy module that is configured to deliver at least one of pacing, cardioversion or defibrillation therapy to a heart of the patient, and the second therapy module comprises an electrical stimulation module configured to deliver electrical stimulation to at least one of a nonmyocardial tissue site or a nonvascular cardiac tissue site within the patient.

11. The system of claim 1, further comprising a shunt-current mitigation circuitry coupled to the first electrode, wherein the shunt-current mitigation circuitry is configured to reduce the shunt-current that is introduced into the first therapy module via the first electrode.

12. The system of claim 11, wherein the shunt-current mitigation circuitry comprises:
a monitor electrically coupled to the first electrode via a wire, wherein the monitor is configured to monitor an electrical parameter value at the first electrode; and
a switch coupled to the monitor,
wherein the monitor is configured to open the switch when the electrical parameter value is greater than or equal to a threshold value.

13. The system of claim 12, further comprising a third electrode, wherein the electrical parameter value comprises at least one of a voltage at the first electrode, a current through the first electrode, or a voltage across at least the first and third electrodes.

14. The system of claim 12, wherein the monitor comprises a voltage monitor.

15. The system of claim 12, wherein the monitor comprises a current monitor.

16. The system of claim 12, wherein the wire comprises a resistive wire comprising a resistance of approximately 10 ohms to approximately 10 kiloohms.

17. The system of claim 12, wherein the switch comprises a relay.

18. The system of claim 11, wherein the shunt-mitigation circuitry comprises a resistor electrically connected to the first electrode.

19. The system of claim 18, wherein the shunt-mitigation circuitry further comprises a switch in parallel with the resistor, wherein the first therapy module is configured to toggle the switch closed during the delivery of the delivery of electrical stimulation by the first therapy module.

20. The system of claim 11, wherein the shunt-mitigation circuitry comprises a diode coupled to the first electrode.

21. The system of claim 11, wherein the shunt-mitigation circuitry comprises a current limiter coupled to the first electrode.

22. The system of claim 21, wherein the current limiter comprises at least one of a fuse, a resettable fuse, or a bimetallic circuit breaker.

23. The system of claim 11, further comprising an implantable medical lead that is electrically connected to the first therapy module and comprising the first electrode, wherein the shunt-current mitigation circuitry is located within at least one of the first therapy module, a connector that electrically connects the implantable medical lead to the first therapy module, or the implantable medical lead.

24. The system of claim 11, further comprising a processor within the first therapy module, wherein the shunt-current mitigation circuitry comprises:
a monitor electrically coupled to the first electrode via a wire, wherein the monitor is configured to monitor an electrical parameter value at the electrode; and
a switch coupled to the monitor, wherein the processor is configured to open the switch when the electrical parameter value is greater than or equal to a threshold value.

25. The system of claim 1, further comprising a switch located between the first electrode and the signal generator of the first therapy module, wherein the first therapy module comprises a processor, wherein the second therapy module is configured to transmit a communication signal to the processor that indicates prospective therapy delivery to the patient by the second therapy module, and wherein the processor is configured to open the switch in response to receiving the communication signal from the second therapy module.

26. The system of claim 1, wherein the first electrode is electrically coupled to the signal generator via an inductive wire.

27. The system of claim 1, wherein the clamping structure comprises a first clamping structure, the system further comprising a second clamping structure electrically connected to the first electrode, wherein a threshold voltage value that activates the second clamping structure is greater than a threshold voltage value that activates the first clamping structure, and wherein the second clamping structure is substantially similar to the first clamping structure.

28. A method comprising:
sensing a voltage gradient via a first, nontherapeutic electrode that is coupled to a housing of a first therapy module via a clamping structure, wherein the voltage gradient is generated by delivery of electrical stimulation by a second therapy module via one or more electrodes coupled to the second therapy module, and wherein the first, nontherapeutic electrode is not one of the electrodes used by the second therapy module for the delivery of the electrical stimulation by the second therapy module;
activating the clamping structure when the sensed voltage gradient is greater than a threshold voltage value; and
reducing a shunt-current that is introduced into the first therapy module via a second electrode that is coupled to a signal generator of the first therapy module,
wherein the shunt-current is generated by the delivery of electrical stimulation by the second therapy module, and wherein activating the clamping structure reduces the shunt-current introduced into the first therapy module via the second electrode.

29. The method of claim 28, wherein the first, nontherapeutic electrode and the activated clamping structure provide a lower impedance electrical path for the shunt-current than an electrical path through the second electrode.

30. The method of claim 28, wherein the clamping structure comprises one or more of a diode, a Zener diode, a gas plasma arrestor, a varistor, or a combination thereof.

31. The method of claim 28, wherein the first, nontherapeutic electrode comprises a conductive surface area that is larger than a conductive surface area of the second electrode.

32. The method of claim 28, wherein the first, nontherapeutic electrode is configured to be implanted in one of a subcutaneous layer, a sub-muscular location, and intravenous location of the patient.

33. The method of claim 28, further comprising:
monitoring an electrical parameter value at the second electrode;
determining whether the electrical parameter value is greater than or equal to a threshold value; and
opening a switch that electrically connects the second electrode and the first therapy module if the electrical parameter value is greater than or equal to the threshold value.

34. The method of claim 28, further comprising:
transmitting a communication signal from the second therapy module to the first therapy module, wherein the communication signal indicates prospective therapy delivery by the second therapy module; and
toggling open a switch located between the second electrode and the signal generator in response to the communication signal.

35. A system comprising:
means for sensing a voltage gradient, the means for sensing being coupled to a housing of a first therapy module via a clamping structure, wherein the voltage gradient is generated by delivery of electrical stimulation by a second therapy module via one or more electrodes coupled to the second therapy module, and wherein the means for sensing is not configured for the delivery of the electrical stimulation by the second therapy module; and means for activating the clamping structure when the sensed voltage gradient is greater than a threshold voltage value for reducing a shunt-current that is introduced into the first therapy module via an electrode that is coupled to a signal generator of the first therapy module, wherein the shunt-current is generated by the delivery of electrical stimulation by the second therapy module.

36. The system of claim 35, wherein the means for sensing comprises a first, nontherapeutic electrode, wherein the electrode comprises a second electrode, and wherein the first, nontherapeutic electrode and the activated clamping structure provide a lower impedance electrical path for the shunt-current than an electrical path through the second electrode.

37. The system of claim 35, wherein the clamping structure comprises one or more of a diode, a Zener diode, a gas plasma arrestor, a varistor, or a combination thereof.

38. The system of claim 35, wherein the means for sensing comprises a first, nontherapeutic electrode, wherein the electrode comprises a second electrode, and wherein the first, nontherapeutic electrode comprises a conductive surface area that is larger than a conductive surface area of the second electrode.

39. The system of claim 35, wherein the means for sensing comprises a nontherapeutic electrode, and wherein the nontherapeutic electrode is configured to be implanted in one of a subcutaneous layer, a sub-muscular location, and intravenous location of the patient.

40. The system of claim 35, further comprising:
means for monitoring an electrical parameter value at the electrode;
means for determining whether the electrical parameter value is greater than or equal to a threshold value; and
means for opening a switch that electrically connects the electrode and the first therapy module if the electrical parameter value is greater than or equal to the threshold value.

41. The system of claim 35, further comprising:
means for transmitting a communication signal from the second therapy module to the first therapy module, wherein the communication signal indicates prospective therapy delivery by the second therapy module; and
means for toggling open a switch located between the electrode and the signal generator in response to the communication signal.

* * * * *